US009610328B2

(12) United States Patent
Mooney et al.

(10) Patent No.: US 9,610,328 B2
(45) Date of Patent: Apr. 4, 2017

(54) ENHANCEMENT OF SKELETAL MUSCLE STEM CELL ENGRAFTMENT BY DUAL DELIVERY OF VEGF AND IGF-1

(75) Inventors: David J. Mooney, Sudbury, MA (US); Cristina Borselli, Naples (IT); Herman Vandenburgh, Providence, RI (US); Dimitry Shvartsman, Belmont, MA (US); Hannah Storrie, Chapel Hill, NC (US); Jeff Lichtman, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/582,900

(22) PCT Filed: Mar. 7, 2011

(86) PCT No.: PCT/US2011/027446
§ 371 (c)(1),
(2), (4) Date: Mar. 15, 2013

(87) PCT Pub. No.: WO2011/109834
PCT Pub. Date: Sep. 9, 2011

(65) Prior Publication Data
US 2013/0177536 A1 Jul. 11, 2013

Related U.S. Application Data

(60) Provisional application No. 61/339,526, filed on Mar. 5, 2010.

(51) Int. Cl.
*A01N 63/00* (2006.01)
*C12N 5/00* (2006.01)
*A61K 38/18* (2006.01)
*A61K 38/30* (2006.01)
*A61L 27/36* (2006.01)
*A61L 27/38* (2006.01)
*A61L 27/52* (2006.01)
*A61L 27/54* (2006.01)
*A61L 27/56* (2006.01)
*A61K 35/34* (2015.01)
*A61K 35/12* (2015.01)

(52) U.S. Cl.
CPC .......... *A61K 38/1866* (2013.01); *A61K 35/12* (2013.01); *A61K 35/34* (2013.01); *A61K 38/18* (2013.01); *A61K 38/30* (2013.01); *A61L 27/3612* (2013.01); *A61L 27/3826* (2013.01); *A61L 27/52* (2013.01); *A61L 27/54* (2013.01); *A61L 27/56* (2013.01); *A61L 2300/414* (2013.01); *A61L 2400/06* (2013.01); *A61L 2400/16* (2013.01); *C08L 2201/12* (2013.01)

(58) Field of Classification Search
CPC .................................. A01N 63/00; C12N 5/00
See application file for complete search history.

(56) References Cited

U.S. PATENT DOCUMENTS

| | | | |
|---|---|---|---|
| 3,773,919 A | 11/1973 | Boswell et al. |
| 4,522,811 A | 6/1985 | Eppstein et al. |
| 4,946,778 A | 8/1990 | Ladner et al. |
| 5,073,627 A | 12/1991 | Curtis et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 6,129,716 A | 10/2000 | Steer |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,403,374 B1 | 6/2002 | Tsien et al. |
| 6,429,199 B1 | 8/2002 | Krieg et al. |
| 6,511,650 B1 | 1/2003 | Eiselt et al. |
| 6,541,022 B1 | 4/2003 | Murphy et al. |
| 6,642,363 B1 | 11/2003 | Mooney et al. |
| 6,685,963 B1 | 2/2004 | Taupin et al. |
| 6,748,954 B2 | 6/2004 | Lee et al. |
| 6,767,928 B1 | 7/2004 | Murphy et al. |
| 6,783,712 B2 | 8/2004 | Slivka et al. |
| 6,790,840 B1 | 9/2004 | Lee et al. |
| 6,797,738 B2 | 9/2004 | Harris et al. |

(Continued)

FOREIGN PATENT DOCUMENTS

| | | |
|---|---|---|
| CN | 101655611 A | 2/2010 |
| EP | 0562862 A1 | 9/1993 |

(Continued)

OTHER PUBLICATIONS

Borselli et al. (Functional muscle regeneration with combined delivery of angiogenesis and myogenesis factors. PNAS Feb. 23, 2010 107(8) 3287-3292).*
Silva et al. (Spatiotemporal control of vascular endothelial growth factor delivery from injectable hydrogels enhances angiogenesis. Journal of Thrombosis and Haemostsis (2007) 5: 590-598).*
Cziorka et al. (Different Desensitization Patterns for Sensory and VascularTRPV1 Populations in the Rat: Expression, Localization and Functional Consequences. PLOS 8 (11): 1-8).*
Boontheekul et al. (Controlling alginate gel degradation utilizing partial oxidation and bimodal molecular weight distribution. Biomaterials 26 (2005) 2455-2465).*
Nakatsu et al. (VEGF121 and VEGF165 Regulate Blood Vessel Diameter Through Vascular Endothelial Growth Factor Receptor 2 in an In Vitro Angiogenesis Model. Laboratory Investigation. 2003: 83(12) 1873-1885).*

(Continued)

*Primary Examiner* — Scott Long
*Assistant Examiner* — Natalie Moss
(74) *Attorney, Agent, or Firm* — McCarter & English, LLP; Maria Lacocotripe Zacharakis

(57) ABSTRACT

An improved device and method for extended repair and regeneration of muscle tissue. An exemplary device comprises (a) a scaffold comprising an ECM component; (b) a combination of growth factors such as VEGF and IGF; and (c) a population of myogenic cells. Implantation of the device leads to muscle regeneration and repair over an extended period of time.

19 Claims, 26 Drawing Sheets

(56) References Cited

U.S. PATENT DOCUMENTS

| | | | |
|---|---|---|---|
| 6,800,733 B2 | 10/2004 | Tsien et al. | |
| 7,157,566 B2 | 1/2007 | Tsien et al. | |
| 7,186,413 B2 * | 3/2007 | Bouhadir et al. | 424/400 |
| 7,192,693 B2 | 3/2007 | Bryant et al. | |
| 7,427,602 B1 | 9/2008 | Shea et al. | |
| 7,575,759 B2 | 8/2009 | Murphy et al. | |
| 7,790,699 B2 | 9/2010 | Melvik et al. | |
| 8,067,237 B2 | 11/2011 | Mooney et al. | |
| 8,188,058 B2 | 5/2012 | Hackam et al. | |
| 8,273,373 B2 | 9/2012 | Alsberg et al. | |
| 8,932,583 B2 | 1/2015 | Mooney et al. | |
| 2002/0131853 A1 | 9/2002 | Nagasawa | |
| 2002/0150604 A1 | 10/2002 | Yi et al. | |
| 2003/0075822 A1 | 4/2003 | Slivka et al. | |
| 2003/0082806 A1 | 5/2003 | Berenson et al. | |
| 2003/0095994 A1 | 5/2003 | Geistlich et al. | |
| 2003/0100527 A1 | 5/2003 | Krieg et al. | |
| 2003/0232895 A1 | 12/2003 | Omidian et al. | |
| 2004/0058883 A1 | 3/2004 | Phillips et al. | |
| 2004/0063206 A1 | 4/2004 | Rowley et al. | |
| 2004/0136968 A1 | 7/2004 | Zheng et al. | |
| 2004/0151764 A1 | 8/2004 | Zamora | |
| 2004/0220111 A1 | 11/2004 | Kleinman et al. | |
| 2004/0242469 A1 | 12/2004 | Lee et al. | |
| 2004/0242482 A1 | 12/2004 | Gehring et al. | |
| 2005/0002915 A1 * | 1/2005 | Atala | A61K 35/44 424/93.21 |
| 2005/0053667 A1 | 3/2005 | Irvine et al. | |
| 2005/0079159 A1 | 4/2005 | Shastri et al. | |
| 2005/0090008 A1 | 4/2005 | Segura et al. | |
| 2005/0106211 A1 | 5/2005 | Nelson et al. | |
| 2005/0154376 A1 | 7/2005 | Riviere et al. | |
| 2005/0177249 A1 | 8/2005 | Kladakis et al. | |
| 2006/0083712 A1 | 4/2006 | Anversa | |
| 2006/0141018 A1 | 6/2006 | Cochrum et al. | |
| 2006/0264380 A1 | 11/2006 | Hellstrom et al. | |
| 2007/0003595 A1 | 1/2007 | Wang et al. | |
| 2007/0020232 A1 | 1/2007 | Rossignol et al. | |
| 2007/0026518 A1 | 2/2007 | Healy et al. | |
| 2007/0081972 A1 | 4/2007 | Sandler et al. | |
| 2007/0116680 A1 | 5/2007 | Stegemann et al. | |
| 2007/0178159 A1 | 8/2007 | Chen et al. | |
| 2007/0190646 A1 | 8/2007 | Engler et al. | |
| 2008/0044900 A1 | 2/2008 | Mooney et al. | |
| 2008/0044990 A1 | 2/2008 | Lee | |
| 2008/0138416 A1 | 6/2008 | Rauh et al. | |
| 2008/0206308 A1 | 8/2008 | Jabbari et al. | |
| 2008/0268052 A1 | 10/2008 | Voytik-Harbin et al. | |
| 2009/0017096 A1 | 1/2009 | Lowman et al. | |
| 2009/0192079 A1 | 7/2009 | Santos et al. | |
| 2009/0238853 A1 | 9/2009 | Liu et al. | |
| 2009/0297579 A1 | 12/2009 | Semino et al. | |
| 2009/0305983 A1 | 12/2009 | Ying et al. | |
| 2010/0015709 A1 | 1/2010 | Rehfeldt et al. | |
| 2010/0055186 A1 | 3/2010 | Dadsetan et al. | |
| 2010/0080816 A1 | 4/2010 | Hadeiba et al. | |
| 2010/0129422 A1 | 5/2010 | Han et al. | |
| 2010/0159008 A1 | 6/2010 | Barron et al. | |
| 2010/0189760 A1 | 7/2010 | Schaffer et al. | |
| 2010/0190741 A1 * | 7/2010 | Cohen et al. | 514/54 |
| 2010/0216739 A1 * | 8/2010 | Lifshitz | A61K 9/0024 514/54 |
| 2010/0272771 A1 | 10/2010 | Harlow et al. | |
| 2011/0020216 A1 | 1/2011 | Mooney et al. | |
| 2011/0117170 A1 | 5/2011 | Cao et al. | |
| 2012/0100182 A1 | 4/2012 | Mooney et al. | |
| 2012/0121539 A1 | 5/2012 | Sands et al. | |
| 2012/0122218 A1 | 5/2012 | Huebsch et al. | |
| 2012/0134967 A1 | 5/2012 | Mooney et al. | |
| 2012/0256336 A1 | 10/2012 | Yano et al. | |
| 2012/0264599 A1 | 10/2012 | Komatsu et al. | |
| 2013/0029030 A1 | 1/2013 | Larsen | |
| 2013/0177536 A1 | 7/2013 | Mooney et al. | |
| 2013/0202707 A1 | 8/2013 | Ali et al. | |
| 2013/0302396 A1 | 11/2013 | Mooney et al. | |
| 2013/0331343 A1 | 12/2013 | Cao et al. | |
| 2014/0227327 A1 | 8/2014 | Bencherif et al. | |
| 2014/0234423 A1 | 8/2014 | Sands et al. | |
| 2015/0024026 A1 | 1/2015 | Mooney et al. | |

FOREIGN PATENT DOCUMENTS

| | | | |
|---|---|---|---|
| EP | 1452191 A2 | 9/2004 | |
| EP | 1561481 A2 | 8/2005 | |
| JP | 2005170816 A | 6/2005 | |
| KR | WO 2007/064152 * | 6/2007 | A61K 47/48 |
| WO | WO-9616086 A1 | 5/1996 | |
| WO | WO-9812228 A1 | 3/1998 | |
| WO | WO-9951259 A2 | 10/1999 | |
| WO | WO-0135932 A2 | 5/2001 | |
| WO | WO-0216557 A2 | 2/2002 | |
| WO | WO-03020884 A2 | 3/2003 | |
| WO | WO-2004006990 A2 | 1/2004 | |
| WO | WO-2004030706 A2 | 4/2004 | |
| WO | WO-2004089413 A1 | 10/2004 | |
| WO | WO-2005026318 A2 | 3/2005 | |
| WO | WO-2005037190 A2 | 4/2005 | |
| WO | WO-2005037293 A1 | 4/2005 | |
| WO | WO-2005046748 A1 | 5/2005 | |
| WO | WO-2005072088 A2 | 8/2005 | |
| WO | WO-2006136905 A2 | 12/2006 | |
| WO | WO-2007030901 A1 | 3/2007 | |
| WO | WO-2007070660 A2 | 6/2007 | |
| WO | WO-2007078196 | 7/2007 | |
| WO | WO-2007107739 | 9/2007 | |
| WO | WO-2007150020 A1 | 12/2007 | |
| WO | WO-2008018707 A1 | 2/2008 | |
| WO | WO-2009002401 A2 | 12/2008 | |
| WO | WO-2009005769 A2 | 1/2009 | |
| WO | WO-2009074341 A1 | 6/2009 | |
| WO | WO-2009102465 A2 | 8/2009 | |
| WO | WO-2009146456 A1 | 12/2009 | |
| WO | WO-2009155583 A1 | 12/2009 | |
| WO | WO-2010120749 A2 | 10/2010 | |
| WO | WO-2011014871 A1 | 2/2011 | |
| WO | WO-2011063336 A2 | 5/2011 | |
| WO | WO-2011130753 A2 | 10/2011 | |
| WO | WO-2011150240 A1 | 12/2011 | |
| WO | WO-2011151431 A1 | 12/2011 | |
| WO | WO-2011163669 A2 | 12/2011 | |
| WO | WO-2012009611 A2 | 1/2012 | |
| WO | WO-2012019049 A1 | 2/2012 | |
| WO | WO-2012048165 A2 | 4/2012 | |
| WO | WO-2012064697 A2 | 5/2012 | |
| WO | WO-2012148684 A1 | 11/2012 | |
| WO | WO-2012149358 A1 | 11/2012 | |
| WO | WO-2012167230 A1 | 12/2012 | |
| WO | WO-2013106852 A1 | 7/2013 | |
| WO | WO-2013158673 A1 | 10/2013 | |

OTHER PUBLICATIONS

Borselli, C. et al. "Functional muscle regeneration with combined delivery of angiogenesis and myogenesis factors" PNAS, Feb. 23, 2010. vol. 107, No. 8. pp. 3287-3292.

Bates. "Improved Muscle Regeneration by Combining VEGF With IGF1." *Regen. Med.* 5.6(2010):853-854.

Blumenthal et al. "Polyurethane Scaffolds Seeded with Genetically Engineered Skeletal Myoblasts: A Promising Tool to Regenerate Myocardial Function." *Artificial Organs.* 34.2(2010):E46-E54.

Conconi et al. "In vitro and in vivo Evaluation of Acellular Diaphragmatic Matrices Seeded with Muscle Precursors Cells and Coated with VEGF Silica Gel to Repair Muscle Defect of the Diaphragm." *J. Biomed. Mater. Res.* 89A.2(2009):304-316.

Kim et al. "The Effect of VEGF on the Myogenic Differentiation of Adipose Tissue Derived Stem Cells Within Thermosensitive Hydrogel Matrices." *Biomaterials.* 31.6(2010):1213-1218.

Rhoads et al. "Satellite Cell-Mediated Angiogenesis in vitro Coincides with a Functional Hypoxia-Inducible Factor Pathway." *Am. J. Physiol. Cell Physiol.* 296.6(2009):C1321-C1328.

(56) References Cited

OTHER PUBLICATIONS

"Antigens and Receptors." *Immunology*. Doan et al., eds. Philadelphia: Wolters Kluwer/Lippincott Williams & Wilsons. (2008):11-23.
Abrahams et al. "Expression and Secretion of Antiviral Factors by Trophoblast Cells Following Stimulation by the TLF-3 Agonist, Poly (I:C)." *Hum. Reprod.* 21.9(2006):2432-2439.
Agrawal et al. "Cutting Edge: Different Toll-Like Receptor Agonists Instruct Dendritic Cells to Induce Distinct Th Responses via Differential Modulation of Extracellular Signal-Regulated Kinase-Mitogen-Activated Protein Kinase and c-Fos." *J. Immunol.* 171.10(2003):4984-4989.
Akira et al. "Pathogen Recognition and Innate Immunity." *Cell.* 124.4(2006):783-801.
Akira et al. "Toll-Like Receptors: Critical Proteins Linking Innate and Acquired Immunity." *Nat. Immunol.* 2.8(2001):675-680.
Aldhous. "Print Me a Heart and a Set of Arteries." *New Scientist.* 2547(2006):19.
Ali et al. "Controlled Local Delivery of GM-CSF From Polymer-Based Vaccines Enhances Anti-Tumor Immune Responses by Priming Host Dendritic Cells." *2007 AACR Annual Meeting.* 48(2007):652. (Abstract #2736).
Ali et al. "Converging Cell Therapy with Biomaterials." *Cell Transplantation from Laboratory to Clinic*. Burlington, MA: Elsevier, Inc. (2006):591-609.
Ali et al. "In situ Regulation of DC Subsets and T Cells Mediates Tumor Regression in Mice." *Sci. Transl. Med.* 1.8(2009):8-19.
Ali et al. "Infection-Mimicking Materials to Program Dendritic Cells in situ." *Nat. Mater.* 8.2(2009):151-158.
Ali et al. "Sustained GM-CSF and PEI Condensed pDNA Presentation Increases the Level and Duration of Gene Expression in Dendritic Cells." *J. Control. Release.* 132.3(2008):273-278.
Allen et al. "Regulation of Satellite Cells During Skeletal Muscle Growth and Development." *Proc. Soc. Exp. Biol. Med.* 194.2(1990):81-86.
Allen et al. "Regulation of Skeletal Muscle Satellite Cell Proliferation by Bovine Pituitary Fibroblast Growth Factor." *Exp. Cell Res.* 152.1(1984):154-160.
Almarza et al. "Evaluation of Three Growth Factors in Combination of Two for Temporomandibular Joint Disc Tissue Engineering." *Arch. Oral Biol.* 51.3(2006):215-221.
Alsberg et al. "Cell-Interactive Alginate Hydrogels for Bone Tissue Engineering." *J. Dent. Res.* 80.11(2001):2025-2029.
Alsberg et al. "Engineering Growing Tissues." *PNAS.* 99.18(2002):12025-12030.
Anderson et al. "The NOD Mouse: A Model of Immune Dysregulation." *Annu. Rev. Immunol.* 23(2005):447-485.
Anderson. "A Role for Nitric OxIde in Muscle Repair: Nitric Oxide-Mediated Activation of Muscle Satellite Cells." *Mol. Biol. Cell.* 11(2000):1859-1874.
Arany et al. "At the Edge of Translation—Materials to Program Cells for Directed Differentiation." *Oral Dis.* 17.3(2011):241-251.
Atala et al. "Endoscopic Treatment of Vesicoureteral Reflux with a Chondrocyte-Alginate Suspension." *J. Urol.* 152(1994):641-643.
Bachelder et al. "Acid-Degradable Polyurethane Particles for Protein-Based Vaccines: Biological Evaluation and in Vitro Analysis of Particle Degradation Products." *Mol. Pharm.* 5.5(2008):876-884.
Badovinac et al. "Regulation of CD8 T+ Cells Undergoing Primary and Secondary Responses to Infection in the Same Host." *J. Immunol.* 170(2003):4933-4942.
Bakri et al. "Pharmacokinetics of Intravitreal Bevacizumab (Avastin)." *Ophthalmology.* 114.5(2007):855-859.
Banchereau et al. "Dendritic Cells and the Control of Immunity." *Nature.* 392.6673(1998):245-252.
Bar-Or et al. "Induction of Antigen-Specific Tolerance in Multiple Sclerosis after Immunization with DNA Encoding Myelin Basic Protein in a Randomized, Placebo-Controlled Phase 1/2 Trial." *Arch. Neurol.* 64.10(2007):1407-1415.
Barbero et al. "Growth Factor Supplemented Matrigel Improves Ectopic Skeletal Muscle Formation—A Cell Therapy Approach." *J. Cell. Physiol.* 186(2001):183-192.
Barrio et al. "A Two-Dimensional Numerical Study of Spatial Pattern Formation in Interacting Turing Systems." *Bull. Math Biol.* 61.3(1999):483-505.
Beauchamp et al. "Dynamics of Myoblast Transplantation Reveal a Discrete Minority of Precursors with Stem Cell-Like Properties as the Myogenic Source." *J. Cell Biol.* 144.6(1999):1113-1122.
Bischoff. "Proliferation of Muscle Satellite Cells on Intact Myofibers in Culture." *Dev. Biol.* 115.1(1986):129-139.
Blanas et al. "Induction of Autoimmune Diabetes by Oral Administration of Autoantigen." *Science.* 274.5293(1996):1707-1709.
Bohl et al. "Role of Synthetic Extracellular Matrix in Development of Engineered Dental Pulp." *J. Biomater. Sci. Polym. Ed.* 9.7(1998):749-764.
Bonauer et al. "MicroRNA-92a Controls Angiogenesis and Functional Recovery of Ischemic Tissues in Mice." *Science.* 324.5935(2009):1710-1713.
Boontheekul et al. "Regulating Myoblast Phenotype Through Controlled Gel Stiffness and Degradation." *Tissue Engin.* 13.7(2007):1431-1442.
Bouhadir et al. "Synthesis of Cross-Linked Poly(aldehyde guluronate) Hydrogels." *Polymer.* 40(1999):3575-3584.
Bowne et al. "Injection of DNA Encoding Granulocyte-Macrophage Colony-Stimulating Factor Recruits Dendritic Cells for Immune Adjuvant Effects." *Cytokines Cell Mol. Ther.* 5.4(1999):217-225.
Brinkman et al. "Photo-Cross Linking of Type 1 Collagen Gels in the Presence of Smooth Muscle Cells: Mechanical Properties, Cell Viability, and Function." *Biomacromolecules.* 4.4(2003):890-895.
Brouwers et al. "Can the Growth Factors PTHrP, Ihh and VEGF, Together Regulate the Development of a Long Bone?" *J. Biomech.* 39.15(2006):2774-2782.
Burdick et al. "Stimulation of Neurite Outgrowth by Neurotrophins Delivered From Degradable Hydrogels." *Biomater.* 27.3(2006):452-459.
Cao et al. "Promoting Angiogenesis via Manipulation of VEGF Responsiveness with Notch Signaling." *Biomater.* 30.25(2009):4085-4093.
Carlson et al. "Notch Signaling Pathway and Tissue Engineering." *Front. Biosci.* 12(2007):5143-5156.
Carmeliet et al. "Angiogenesis in Cancer and Other Diseases." *Nature.* 407.6801(2000):249-257.
Carmeliet. "Mechanisms of Angiogenesis and Arteriogenesis." *Nat. Med.* 6.3(2000):389-395.
Chan et al. "Antifibrotic Effects of Suramin in Injured Skeletal Muscle After Laceration." *J. Appl. Physiol.* 95(2003):771-780.
Chan et al. "Helix Induction in Antimicrobial Peptides by Alginate in Biofilms." *J. Biol. Chem.* 279.37(2004):38749-38754.
Chen et al. "Integrated Approach to Designing Growth Factor Delivery Systems." *FASEB J.* 21.14(2007):3896-3903.
Chen et al. "Polymeric Growth Factor Delivery Strategies for Tissue Engineering." *Pharm. Res.* 20.8(2003):1103-1112.
Chen et al. "Skeletal Muscle Stem Cells." *Reprod. Biol. Endocrinol.* 1(2003):101.
Chen et al. "Spatio-Temporal VEGF and PDGF Delivery Patterns Blood Vessel Formation and Maturation." *Pharm. Res.* 24.2(2007):258-264.
Choi. "Replacement Organs, Hot Off the Press." *New Scientist.* 177.2379(2003):16.
Chromiak et al. "Bioreactor Perfusion System for the Long-Term Maintenance of Tissue-Engineered Skeletal Muscle Organoids." *In Vitro Cell Dev. Biol. Anim.* 34.9(1998):694-703.
Clauss et al. "Interstitial Transport of Rabbit and Sheep Antibodies in Normal and Neoplastic Tissues." *Cancer Res.* 50.12(1990):3487-3492.
Cohen et al. "Controlled Delivery Systems for Proteins Based on Poly(Lactic/Glycolic Acid) Microspheres." *Pharm. Res.* 8.6(1991):713-720.
Conboy et al. "The Regulation of Notch Signaling Controls Satellite Cell Activation and Cell Fate Determination in Postnatal Myogenesis." *Dev. Cell.* 3.3(2002):397-409.

(56) References Cited

OTHER PUBLICATIONS

Conn et al. "Purification of a Glycoprotein Vascular Endothelial Cell Mitogen from a Rat Glioma-Derived Cell Line." *PNAS*. 87.4(1990):1323-1327.
Cooper et al. "Extended Amplification In Vitro and Replicative Senescence: Key Factors Implicated in the Success of Human Myoblast Transplantation." *Hum. Gene Ther*. 14(2003):1169-1179.
Cornelison et al. "Single-Cell Analysis of Regulatory Gene Expression in Quiescent and Activated Mouse Skeletal Muscle Satellite Cells." *Dev. Biol*. 191.2(1997):270-283.
Cornelison et al. "Syndecan-3 and Syndecan-4 Specifically Mark Skeletal Muscle Satellite Cells and Are Implicated in Satellite Cell Maintenance and Muscle Regeneration." *Dev. Biol*. 239.1(2001):79-94.
Cullen et al. "Investigation of Vascular Endothelial Growth Factor Effects on Pulmonary Endothelial Monolayer Permeability and Neutrophil Transmigration." *Gen. Pharmacol*. 35.3(2000):149-157.
Curiel et al. "Tumor Immunotherapy: Inching Toward the Finish Line." *J. Clin. Invest*. 109.3(2002):311-312.
D'Amico et al. "The Early Progenitors of Mouse Dendritic Cells and Plasmacytoid Predendritic Cells are within the Bone Marrow Hemopoietic Precursors Expressing Flt3." *J. Exp. Med*. 198.2(2003):293-303.
Daro et al. "Polyethylene Glycomodified GM-CSF Expands CD11bhighCD11chigh but not CD11blowCD11chigh Murine Dendritic Cells In Vivo: A Comparative Analysis with Flt3 Ligand." *J. Immunol*. 165.1(2000):49-58.
De Temmerman et al. "Particulate Vaccines: On the Quest for Optimal Delivery and Immune Response." *Drug Disc. Today*. 16.13/14(2011):569-582.
den Haan et al. "CD8+ by not CD8–Dendritic Cells Cross-Prime Cytotoxic T Cells In Vivo." *J. Exp. Med*. 192.12(2000):1685-1696.
Dennis et al. "Excitability and Contractility of Skeletal Muscle Engineered From Primary Cultures and Cell Lines." *Am. J. Physiol. Cell Physiol*. 280(2001):C288-C295.
Dennis et al. "Excitability and Isometric Contractile Properties of Mammalian Skeletal Muscle Constructs Engineered in vitro." *In Vitro Cell Dev. Biol. Anim*. 36.5(2000):327-335.
Dieu et al. "Selective Recruitment of Immature and Mature Dendritic Cells by Distinct Chemokines Expressed in Different Anatomic Sites." *J. Exp. Med*. 188.2(1988):373-386.
Dor et al. "Making Vascular Networks in the Adult: Branching Morphogenesis Without a Roadmap." *Trends Cell Biol*. 13.3(2003):131-136.
Dranoff et al. "Vaccination with Irradiated Tumor Cells Engineered to Secrete Murine Granulocyte-Macrophage Colony-Stimulating Factor Stimulates Potent, Specific and Long-Lasting Anti-Tumor Immunity." *PNAS*. 90.8(1993):3539-3543.
Dranoff. "Cyotkines in Cancer Pathogenesis and Cancer Therapy." *Nat. Rev. Cancer*. 4.1(2004):11-22.
Dudley et al. "Adoptive Cell Transfer Therapy Following Non-Myeloablative by Lymphodepleting Chemotherapy for the Treatment of Patients with Refractory Metastatic Melanoma." *J. Clin. Oncol*. 23.10(2005):2346-2357.
Ehrbar et al. "Endothelial Cell Proliferation and Progenitor Maturation by Fibrin-Bound VEGF Variants with Differential Susceptibilities to Local Cellular Activity." *J. Control. Release*. 101(2004):93-109.
Eiselt et al. "Porous Carriers for Biomedical Applications Based on Alginate Hydrogels." *Biomat*. 21.19(2000):1921-1927.
El-Backly et al. "Regeneration of Dentine/Pulp-Like Tissue Using a Dental Pulp Stem Cell/Poly(Lactic-Co-Glycolic) Acid Scaffold Construct in New Zealand White Rabbits." *Aust. Endod. J*. 34.2(2008):52-67.
Eldar et al. "Elucidating Mechanisms Underlying Robustness of Morphogen Gradients." *Curr. Opin. Genet. Dev*. 14.4(2004):435-439.
Eldar et al. "Robustness of the BMP Morphogen Gradient in *Drosophila* Embryonic Patterning." *Nature*. 419.6904(2002):304-308.
Eldar et al. "Self-Enhanced Ligand Degradation Underlies Robustness of Morphogen Gradients." *Dev. Cell*. 5.4(2003):635-646.
Engler et al. "Matrix Elasticity Directs Stem Cell Lingeage Specification." *Cell*. 126.4(2006):677-689.
Ennett et al. "Temporally Regulated Delivery of VEGF in vitro and in vivo." *J. Biomed. Mater. Res. A*. 79.1(2006):176-184.
Faissner et al. "Boundaries and Inhibitory Molecules in Developing Neural Tissues." *Glia*. 13.4(1995):233-254.
Farrar et al. "T Helper Subset Development: Roles of Instruction, Selection, and Transcription." *J. Clin. Invest*. 109.4(2002):431-435.
Ferrara et al. "Angiogenesis as a Therapeutic Target." *Nature*. 438.7070(2005):967-974.
Ferrara et al. "Discovery and Development of Bevacizumab, an Anti-VEGF Antibody for Treating Cancer." *Nat. Rev. Drug Discov*. 3.5(2004):391-400.
Folkman. "Angiogenesis." *Annu. Rev. Med*. 57(2006):1-18.
Fonseca et al. "Capitalizing on the Immunogenicity of Dying Tumor Cells." *Clin. Cancer Res*. 14.16(2008):1603-1608.
Fontaine et al. "Surgical Treatment of Peripheral Circulation Disorders." *Helv. Chir. Acta*. 21.56(1954):499-533. (German Original, No English Translation Available).
Friedrich et al. "Promoter Traps in Embryonic Stem Cells: A Genetic Screen to Identify and Mutate Developmental Genes in Mice." *Genes Dev*. 5(1991):1513-1523.
Fukushima et al. "The Use of an Antifibrosis Agent to Improve Muscle Recovery After Laceration." *Am. J. Sports Med*. 29.4(2001):394-402.
Gamvrellis et al. "Vaccines that Facilitate Antigen Entry into Dendritic Cells." *Immunol. Cell Biol*. 82(2004):506-516.
GenBank Accession No. A32848.1, Jul. 5, 2002.
GenBank Accession No. AAA35789.1, Apr. 27, 1993.
GenBank Accession No. AAA56738.1, Dec. 7, 1994.
GenBank Accession No. AAA60552.1, Nov. 24, 2003.
GenBank Accession No. AAA64297.1, Mar. 24, 1995.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. ABC86910, Jan. 3, 2011.
GenBank Accession No. CAA01954.1, Jun. 15, 1995.
GenBank Accession No. CAA40093.1, Oct. 7, 2008.
GenBank Accession No. CAA62632.1, Sep. 15, 1995.
GenBank Accession No. CAG46721.1, Jun. 29, 2004.
GenBank Accession No. CBI71013.1, Feb. 2, 2010.
GenBank Accession No. EU826563.1, Jul. 23, 2008.
GenBank Accession No. NM_000230.2, Dec. 17, 2012.
GenBank Accession No. NM_000514.3, Aug. 19, 2012.
GenBank Accession No. NM_000601.4, Nov. 25, 2012.
GenBank Accession No. NM_000614.3, Sep. 9, 2012.
GenBank Accession No. NM_000660.4, Dec. 9, 2012.
GenBank Accession No. NM_000800.3, Mar. 4, 2012.
GenBank Accession No. NM_001102654.1, Dec. 16, 2012.
GenBank Accession No. NM_001111283.1, Dec. 9, 2012.
GenBank Accession No. NM_001171630.1, Dec. 9, 2012.
GenBank Accession No. NM_001202.3, Nov. 18, 2012.
GenBank Accession No. NM_002506.2, Dec. 9, 2012.
GenBank Accession No. NM_002632.4, May 4, 2011.
GenBank Accession No. NM_003236.2, Aug. 21, 2011.
GenBank Accession No. NM_003263.3, Jan. 5, 2013.
GenBank Accession No. NM_003264.3, Jan. 6, 2013.
GenBank Accession No. NM_003268.5, Nov. 25, 2012.
GenBank Accession No. NM_006068.4, Oct. 28, 2012.
GenBank Accession No. NM_016562.3, Jan. 6, 2013.
GenBank Accession No. NM_030956.3, Oct. 28, 2012.
GenBank Accession No. NM_033023.4, Nov. 18, 2012.
GenBank Accession No. NM_138554.4, Dec. 29, 2012.
GenBank Accession No. NM_138636.4, Dec. 23, 2012.
GenBank Accession No. NM_170731.4, Dec. 9, 2012.
GenBank Accession No. NM_205819.3, Dec. 6, 2012.

(56) References Cited

OTHER PUBLICATIONS

GenBank Accession No. NM_205820.1, Jan. 5, 2013.
GenBank Accession No. NM_205823.2, Jan. 6, 2013.
GenBank Accession No. NP_001096124.1, Dec. 16, 2012.
GenBank Accession No. NP_002010.2, Dec. 9, 2012.
GenBank Accession No. NP_003254.2, Jan. 5, 2013.
GenBank Accession No. NP_003255.2, Jan. 6, 2013.
GenBank Accession No. NP_003259.2, Nov. 25, 2012.
GenBank Accession No. NP_006059.2, Oct. 28, 2012.
GenBank Accession No. NP_057646.1, Jan. 6, 2013.
GenBank Accession No. NP_112218.2, Oct. 28, 2012.
GenBank Accession No. NP_570912.2, Nov. 18, 2012.
GenBank Accession No. NP_612564.1, Dec. 29, 2012.
GenBank Accession No. NP_619542.1, Dec. 23, 2012.
GenBank Accession No. NP_991388.2, Dec. 6, 2012.
GenBank Accession No. NP_991389.1, Jan. 5, 2013.
GenBank Accession No. NP_991392.1, Jan. 6, 2013.
GenBank Accession No. P49771.1, Jan. 9, 2013.
Gerhardt et al. "VEGF Guides Angiogenic Sprouting Utilizing Endothelial Tip Cell Filopodia." *J. Cell Biol.* 161.6(2003):1163-1177.
Gilboa. "Dendritic-Cell Based Cancer Vaccines." *J. Clin. Invest.* 117.5(2007):1195-1203.
Gnjatic et al. "Toll-Like Receptor Agonists: Are They Good Adjuvants?" *Cancer J.* 16.4(2010):382-391.
Godbey et al. "Size Matters: Molecular Weight Affects the Efficiency of Poly(ethylenimine) as a Gene Delivery Vehicle." *J. Biomed. Mater. Res.* 45.3(1999):268-275.
Godbey et al. "Tracking the Intracellular Path of Poly(ethylenimine)/DNA Complexes for Gene Delivery." *PNAS.* 96.9(1999):5177-5181.
Gospodarowicz et al. "Effect of Fibroblast Growth Factor on the Division and Fusion of Bovine Myoblasts." *J. Cell Biol.* 70.2(1976):395-405.
Griffith et al. "Tissue Engineering—Current Challenges and Expanding Opportunities." *Science.* 295(2002):1009-1014.
Grimmer et al. "Tracheal Reconstruction Using Tissue-Engineered Cartilage." *Arch. Otolaryngol. Head Neck Surg.* 130.10(2004):1191-1196.
Gros et al. "A Common Somitic Origin for Embryonic Muscle Progenitors and Satellite Cells." *Nature.* 435(2005):954-958.
Gullberg et al. "Extracellular Matrix and Its Receptors During Development." *Int. J. Dev. Biol.* 39(1995):845-854.
Gussoni et al. "Dystophin Expression and in the *mdx* Mouse Restored by Stem Cell Transplantation." *Nature.* 401(1999):390-394.
Hamby et al. "Small Molecule Inhibitors of Tumor-Promoted Angiogenesis, Including Protein Tyrosine Kinase Inhibitors." *Pharmacol. Ther.* 82.2-3(1999):169-193.
Hamdy et al. "Targeting Dendritic Cells with Nano-Particulate PLGA Cancer Vaccine Formulations." *Adv. Drug Deliv. Rev.* 63.10(2011):943-955.
Hamilton et al. "GM-CSF Biology." *Growth Factors.* 22.4(2004):225-231.
Hamilton. "GM-CSF in Inflammation and Autoimmunity." *Trends Immunol.* 23.8(2002):403-408.
Hanada. "Efficacy of Rehabilitative Therapy in Regional Musculoskeletal Conditions." *Best Pract. Res. Clin. Rheumatol.* 17.1(2003):151-166.
Hansen et al. "Comparison of Clinical Grade Type 1 Polarized and Standard Matured Dendritic Cells for Cancer Immunotherapy." *Vaccine.* 31.4(2013):639-646.
Hansen et al. "Integrin Binding and Cell Spreading on Extracellular Matrix Act at Different Points in the Cell Cycle to Promote Hepatocyte Growth." *Mol. Biol. Cell.* 5(1994):967-975.
Harris et al. "Open Pore Biodegradable Matrices Formed with Gas Foaming." *J. Biomed. Mater. Res.* 42.3(1998):396-402.
Harrison. "What is the Status of Reaction-Diffusion Theory Thirty-Four Years After Turing?" *J. Theor. Biol.* 125.4(1987):369-384.
Hartgerink et al. "Peptide-Amphiphile Nanofibers: A Versatile Scaffold for the Preparation of Self-Assembling Materials." *PNAS.* 99.8(2002):5133-5138.
Hartmann et al. "CpG DNA: A Potent Signal for Growth, Activation, and Maturation of Human Dendritic Cells." *PNAS.* 96(1999):9305-9310.
Hashimoto et al. "Development of Alginate Wound Dressings Linked with Hybrid Peptides Derived from Laminin and Elastin." *Biomaterials.* 25.7-8(2004):1407-1414.
Hawke et al. "Myogenic Satellite Cells: Physiology to Molecular Biology." *J. Appl. Physiol.* 91(2001):534-551.
Helm et al. "Synergy Between Interstitial Flow and VEGF Directs Capillary Morphogenesis in vitro Through a Gradient Amplification Mechanism." *PNAS.* 102.44(2005)15779-15784.
Henry et al. "The VIVA Trial: Vascular Endothelial Growth Factor in Ischemia for Vascular Angiogenesis." *Circulation.* 107.10(2003):1359-1365.
Hermanson. *Bioconjugate Techniques.* New York: Academic Press. (1996):152-185.
Heslop et al. "Transplanted Primary Neonatal Myoblasts can Give Rise to Functional Satellite Cells as Identified Using the Myf5nlacZl+ Mouse." *Gene Ther.* 8(2001):778-783.
Hildner et al. "Batf3 Deficiency Reveals a Critical Role for CD8α+ Dendritic Cells in Cytotoxic T Cell Immunity." *Science.* 322.5904(2008):1097-1100.
Hill et al. "Designing Scaffolds to Enhance Transplanted Myoblast Survival and Migration." *Tissue Engin.* 12.5(2006):1295-1304.
Hill et al. "Muscle Satellite (Stem) Cell Activation During Local Tissue Injury and Repair." *J. Anat.* 203.1(2003):89-99.
Hill. "Macroporous Scaffold Architecture, Peptide, HGF/FGF and Myoblast Incorporation Enhance Myogenesis." *IADR/AADR/CADR 83rd General Session.* (Mar. 9-12, 2005). Poster #2829.
Hirano et al. "Peptide and Protein Presenting Materials for Tissue Engineering." *Adv. Mat.* 16.1(2004):17-25.
Hodge-Dufour et al. "Inhibition of Interferon γ Induced Interleukin 12 Production: A Potential Mechanism for the Anti-Inflammatory Activities of Tumor Necrosis Factor." *PNAS.* 95.23(1998):13806-13811.
Hodi et al. "Immunologic and Clinical Effects of Antibody Blockade of Cytotoxic T Lymphocyte-Associated Antigen 4 in Previously Vaccinated Cancer Patients." *PNAS.* 105.8(2008):3005-3010.
Horsley et al. "IL-4 Acts as a Myoblast Recruitment Factor During Mammalian Muscle Growth." *Cell.* 113.4(2003):483-494.
Hsiong et al. "Differentiation Stage Alters Matrix Control of Stem Cells." *J. Biomed. Mater. Res. Part A.* 8(2007):145-156.
Huang et al. "Fabrication and in vitro Testing of Polymeric Delivery Systems for Condensed DNA." *J. Biomed. Mater. Res.* 67(2003):1384-1392.
Huang et al. "Long-Term In Vivo Gene Expression via Delivery of PEI-DNA Condensates From Porous Polymer Scaffolds." *Hum. Gene Ther.* 16.5(2005):609-617.
Hubbell et al. "Materials Engineering for Immunomodulation." *Nature.* 462(2009):449-460.
Hubbell. "Biomaterials in Tissue Engineering." *Bio/Tech.* 13(1995):565-576.
Huebsch et al. "Harnessing Traction-Mediated Manipulation of the Cell/Matrix Interface to Control Stem-Cell Fate." *Nat. Mater.* 9.6(2010):518-526.
Ishihara et al. "Roles of Bradykinin in Vascular Permeability and Angiogenesis in Solid Tumor." *Int. Immunopharmacol.* 2.4(2002):499-509.
Jain. "Molecular Regulation of Vessel Maturation." *Nat. Med.* 9.6(2003):685-693.
Jain. "The Manufacturing Techniques of Various Drug Loaded Biodegradable Poly(lactide-co-glycolide) (PLGA) Devices." *Biomater.* 21.23(2000):2475-2490.
Jankovic et al. "In the Absence of IL-12, CD4+ T Cell Responses to Intracellular Pathogens Fail to Default to a Th2 Pattern and are Host Protective in an IL-10-/- Setting." *Immunity.* 16.3(2002):429-439.
Jego et al. "Plasmacytoid Dendritic Cells Induce Plasma Cell Differenetiation Through Type I Interferon and Interleukin 6." *Immunity.* 19.2(2003):225-234.

(56) References Cited

OTHER PUBLICATIONS

Jiang et al. "Self-Organization of Periodic Patterns by Dissociated Feather Mesenchymal Cells and the Regulation of Size, Number and Spacing of Primorida." *Development.* 126.22(1999):4997-5009.
Jinushi et al. "Enhancing the Clinical Activity of Granulocyte-Macrophage Colony-Stimulating Factor-Secreting Tumor Cell Vaccines." *Immunol. Rev.* 222(2008):287-298.
Jinushi et al. "MFG-E8-Mediated Uptake of Apoptotic Cells by APCs Links the Pro- and Antiinflammatory Activities of GM-CSF." *J. Clin. Invest.* 117.7(2007):1902-1913.
Johnson et al. "Activation of Skeletal Muscle Satellite Cells and the Role of Fibroblast Growth Factor Receptors." *Exp. Cell Res.* 219.2(1995):449-453.
Kanzler et al. "Therapeutic Targeting of Innate Immunity with Toll-Like Receptor Agaonists and Antagonists." *Nat. Med.* 13.5(2007):552-559.
Kawai et al. "Innate Immune Recognition of Viral Infection." *Nat. Immunol.* 7.2(2006):131-137.
Kawashima et al. "Pulmonary Delivery of Insulin With Nebulized DL-Lactide/Glycolide Copolymer (PLGA) Nanospheres to Prolong Hypoglycemic Effect." *J. Control. Release.* 62.1-2(1999):279-287.
Kim et al. "An Overview of Cartilage Tissue Engineering." *Yonsei Med. J.* 41.6(2000):766-773.
Kinoshita et al. "Successive Injections in MDX Mice of Myoblasts Grown with bFGF." *Neuromusc. Disord.* 6.3(1996):187-193.
Kisak et al. "The Vesosome—A Multicompartment Drug Delivery Vehicle." *Curr. Med. Chem.* 11.2(2004):199-219.
Klebanoff et al. "CD8+ T-Cell Memory in Tumor Immunology and Immunotherapy." *Immunol. Rev.* 211(2006):214-224.
Klinman. "Immunotherapeutic Uses of CpG Oligodeoxynucleotides." *Nat. Rev. Immunol.* 4.4(2004):249-258.
Kondo et al. "A Reaction-Diffusion Wave on the Skin of the Marine Angelfish *Pomacanthus.*" *Nature.* 376(2002):765-768.
Kong et al. "Controlling Rigidity and Degradation of Alginate Hydrogels via Molecular Weight Distribution." *Biomacromolec.* 5.5(2004):1720-1727.
Kong et al. "Designing Alginate Hydrogels to Maintain Viability of Immobilized Cells." *Biomat.* 24.22(2003):4023-4029.
Kong et al. "Non-Viral Gene Delivery Regulated by Stiffness of Cell Adhesion Substrates." *Nat. Mater.* 4(2005):406-410.
Krieg. "Development of TLR9 Agonists for Cancer Therapy." *J. Clin. Invest.* 117.5(2007):1184-1194.
Krishnamachari et al. "PLGA Microparticles that Co-Deliver Antigen and Toll Like Receptor Ligand Adjuvants for Applications in Cancer Immunotherapy." *AAPS Pharmaceutica.* Nov. 11, 2009. Web. Mar. 1, 2013. http://abstracts.aapspharmaceutica.com/ExpoAAPS09/CC/forms/attendee/index.aspx?content=sessionInfo&sessionId=2716.
Kumamoto et al. "Induction of Tumor-Specific Protective Immunity by in situ Langerhans Cell Vaccine." *Nat. BioTechnol.* 20.1(2002):64-69.
Kumar et al. "Toll-Like Receptors and Innate Immunity." *Biochem. Biophys. Res. Commun.* 388.4(2009):621-625.
Kurts et al. "CD8 T Cell Ignorance or Tolerance to Islet Antigens Depends on Antigen Dose." *PNAS.* 96.22(1999):12703-12707.
Kwon et al. "In vivo Targeting Dendritic Cells for Activation of Cellular Immunity Using Vaccine Carriers Based on pH-Responsive Microparticles." *PNAS.* 102.51(2005):18264-18268.
Langer et al. "Tissue Engineering." *Science.* 260(1993):920-926.
Lanzavecchia et al. "Regulation of T Cell Immunity by Dendritic Cells." *Cell.* 106.3(2001):263-266.
Leach et al. "Coating of VEGF-Releasing Scaffolds with Bioactive Glass for Angiogenesis and Bone Regeneration." *Biomater.* 27.17(2006):3249-3255.
Lee et al. "Hydrogel Formation via Vell Crosslinking." *Adv. Mat.* 15.21(2003):1828-1832.
Lee et al. "Hydrogels for Tissue Engineering." *Chem. Rev.* 101.7(2001):1869-1879.

Lefaucheur et al. "The Cellular Events of Injured Muscle Regeneration Depend on the Nature of the Injury." *Neuromusc. Disorders.* 5.6(1995):501-509.
Lensch et al. "Scientific and Clinical Opportunities for Modeling Blood Disorders With Embyronic Stem Cells." *Blood.* 107.7(2006):2605-2612.
Leshem et al. "Hepatocyte Growth Factor (HGF) Inhibits Skeletal Muscle Cell Differentiation: A Role for the bHLH Protein Twist and the cdk Inhibitor p27." *J. Cell. Physiol.* 184(2000):101-109.
Li et al. "Effect of Growth Factors and Extracellular Matrix Materials on the Proliferation and Differentiation of Microencapsulated Myoblasts." *J. Biomater. Sci. Polym. Ed.* 14.6(2003):533-549.
Li et al. "Effects of Three-Dimensional Scaffolds on Cell Organization and Tissue Development." *Biotech. Bioprocess Eng.* 6.5(2001):311-325.
Li. "TNF-α is a Mitogen is Skeletal Muscle." *Am. J. Physiol. Cell Physiol.* 285(2003):C370-C376.
Lipton et al. "Developmental Fate of Skeletal Satellite Cells." *Science.* 205(1979):1292-1294.
Liu. "Dendritic Cell Subsets and Lineages, and Their Functions in Innate and Adaptive Immunity." *Cell.* 106.3(2001):259-262.
Lu et al. "Muscle-Derived Stem Cells Seeded Into Acellular Scaffolds Develop Calcium-Dependent Contractile Activity That is Modulated by Nicotinic Receptors." *Urology.* 61.6(2003):1285-1291.
Lubeck. "The Costs of Musculoskeletal Disease: Health Needs Assessment and Health Economics." *Best Pract. Res. Clin. Rheumatol.* 17.3(2003):529-539.
Lumelsky et al. "Differentiation of Embryonic Stem Cells to Insulin-Secreting Structures Similar to Pancreatic Islets." *Science.* 292.5520(2001):1389-1394.
Mach et al. "Differences in Dendritic Cells Stimulated in Vivo by Tumors Engineered to Secrete Granulocyte-Macrophage Colony-Stimulating Factor or Flt3-Ligand." *Cancer Res.* 60.12(2000):3239-3246.
Magram et al. "IL-12-Deficient Mice are Defective but not Devoid of Type 1 Cytokine Responses." *Ann. N.Y. Acad. Sci.* 795(1996):60-70.
Maini. "Spatial and Spatio-Temporal Patterns in a Cell-Haptotaxis Model."*J. Math. Biol.* 27.5(1989):507-522.
Maley et al. "Extracellular Matrix, Growth Factors, Genetics: Their Influence on Cell Proliferation and Myotube Formation in Primary Cultures of Adult Mouse Skeletal Muscle." *Exp. Cell Res.* 219.1(1995):169-179.
Martinsen et al. "Alginate as Immobilization Material." *Biotech. Bioeng.* 33.1(1989):79-89.
Massia et al. "An RGD Spacing of 440 nm is Sufficient for Integrin αvβ3-Mediated Fibroblast Spreading and 140 nm for Focal Contact and Stress Fiber Formation." *J. Cell Biol.* 114.5(1991):1089-1100.
Matthew et al. "Subperiosteal Behaviour of Alginate and Cellulose Wound Dressing Materials." *Biomaterials.* 16.4(1995):275-278.
McKinney-Freeman et al. "Muscle-Derived Hematopoietic Stem Cells are Hematopoietic in Origin." *PNAS.* 99.3(2002):1341-1346.
McPherron et al. "Regulation of Skeletal Muscle Mass in Mice by a New TGF-β Superfamily Member." *Nature.* 387(1997):83-90.
Melero-Martin et al. "Engineering Robust and Functional Vascular Networks In Vivo With Human Adult and Cord Blood-Derived Progenitor Cells." *Circ. Res.* 103.2(2008):194-202.
Mellman et al. "Dendritic Cells: Specialized and Regulated Antigen Processing Machines." *Cell.* 106.3(2001):255-258.
Menetrey et al. "Suturing Versus Immobilization of a Muscle Laceration: A Morphological and Functional Study in a Mouse Model." *Am. J. Sports Med.* 27.2(1999):222-229.
Meyer et al. "Clinical Investigations of Toll-Like Receptor Agonists." *Expert Opin. Investig. Drugs.* 17.7(2008):1051-1065.
Meylan et al. "Intracellular Pattern Recognition Receptors in the Host Response." *Nature.* 442.7098(2006):39-44.
Miller et al. "Hepatocyte Growth Factor Affects Satellite Cell Activation and Differentiation in Regenerating Skeletal Muscle." *Am. J. Physiol. Cell Physiol.* 278(2000):C174-C181.

(56) References Cited

OTHER PUBLICATIONS

Mitchell et al. "The Exogenous Administration of Basic Fibroblast Growth Factor to Regenerating Skeletal Muscle in Mice Does Not Enhance the Process of Regeneration." *Growth Factors.* 13.1-2(1996):37-55.
Moioli et al. "Matrices and Scaffolds for Drug Delivery in Dental, Oral and Craniofacial Tissue Engineering." *Adv. Drug Deliv. Rev.* 59.4-5(2007):308-324.
Mooney et al. "Switching From Differentiation to Growth in Hepatocytes: Control by Extracellular Matrix." *J. Cell. Phys.* 151.3(1992):497-505.
Moser et al. "Dendritic Cell Regulation of TH1-TH2 Regulation." *Nat. Immunol.* 1.3(2000):199-205.
Naik et al. "Development of Plasmacytoid and Conventional Dendritic Cell Subtypes From Single Precursor Cells Derived in vitro and in vivo." *Nat. Immunol.* 8.11(2007):1217-1226.
Nair et al. "Polymers as Biomaterials for Tissue Engineering and Controlled Drug Delivery." *Adv. Biochem. Eng. Biotechnol.* 102(2006):47-90.
NCBI Accession No. NM_000758, Apr. 1, 2012.
NCBI Accession No. NM_003265, Dec. 30, 2012.
NCBI Accession No. NM_017442, Apr. 14, 2012.
NCBI Accession No. NP_000749.2, Apr. 1, 2012.
NCBI Accession No. NP_001020537, Jan. 30, 2011.
NCBI Accession No. NP_001020538, Jan. 30, 2011.
NCBI Accession No. NP_001020539, Jan. 30, 2011.
NCBI Accession No. NP_001020540, Jan. 30, 2011.
NCBI Accession No. NP_001028928, Jan. 30, 2011.
NCBI Accession No. NP_003367, Jan. 30, 2011.
NCBI Accession No. NP_059138, Apr. 14, 2012.
Nehls et al. "A Novel, Microcarrier-Based in Vitro Assay for Rapid and Reliable Quantification of Three-Dimensional Cell Migration and Angiogenesis." *Microvasc. Res.* 50.3(1995):311-322.
Noguera-Troise et al. "Blockade of Dll4 Inhibits Tumour Growth by Promoting Non-Productive Angiogenesis." *Nature.* 444.7122(2006):1032-1037.
O'Garra et al. "Are Dendritic Cells Afraid of Commitment?" *Nat. Immunol.* 5.12(2004):1206-1208.
O'Shea et al. "Type 1 IFNs and Regulation of TH1 Responses: Enigmas Both Resolved and Emerge." *Nat. Immunol.* 1.1(2000):17-19.
Ohlstein et al. "The Stem Cell Niche: Theme and Variations." *Curr. Opin. Cell Biol.* 16.6(2004):693-699.
Oldenburg et al. "TLR13 Recognizes Bacterial 23S rRNA Devoid of Erythromycin Resistance-Forming Modification." *Science.* 337.6098(2012):1111-1115.
Oldenhove et al. "Decrease of Foxp3+ Treg Cell Number and Acquisition of Effector Cell Phenotype During Lethal Infection." *Immunity.* 31.5(2009):772-786.
Ota et al. "Percutaneous Subxiphoid Access to the Epicardium Using a Miniature Crawling Robotic Device." *Innovations.* 1.5(2006):227-231.
Overwijk et al. "Tumor Regression and Autoimmunity After Reversal of a Functionally Tolerant State of Self-Reactive CD8+ T Cells." *J. Exp. Med.* 198.4(2003):569-580.
Ozawa et al. "Microenvironmental VEGF Concentration, Not Total Dose, Determines a Threshold Between Normal and Aberrant Angiogenesis." *J. Clin. Invest.* 113.4(2004):516-527.
Padilla et al. "Insufficient TLR Activation Contributes to the Slow Development of CD8+ T Cell Responses in *Trypanosoma cruzi* Infection." *J. Immunol.* 183(2009):1245-1252.
Palacio et al. "Interleukin 10 and Tumor Necrosis Factor α Gene Expression in Respiratory and Peripheral Muscles." *Arch. Bronconeumol.* 38.7(2002):311-316. (Spanish Original and English Abstract).
Partridge et al. "Conversion of mdx Myofibres From Dystrophin-Negative to -Positive by Injection of Normal Myoblasts." *Nature.* 337(1989):176-179.
Pelinkovic et al. "Tissue Engineering and Gene Therapy of the Muscoskeletal System with Muscle Cells." *Z. Orthop. Ihre Grenzgeb.* 138.5(2000):402-406. (German Original and English Abstract).
Peters et al. "Engineering Vascular Networks in Porous Polymer Matrices." *J. Biomed. Mater. Res.* 60.4(2002):668-678.
Phillippi. "Patterning of Multiple Cell Lineages from a Single Stem Cell Population." *Annual Meeting of the American Society for Cell Biology.* (Dec. 10, 2006).
Pluen et al. "Role of Tumor-Host Interactions in Interstitial Diffusion of Macromolecules: Cranial vs. Subcutaneous Tumors." *PNAS.* 98.8(2001):4628-4633.
Pooyan et al. "Conjugates Beating Multiple Formyl-Methionyl Peptides Display Enhanced Binding to, but not Activation of Phagocytic Cells." *Bioconjugate Chem.* 13.2(2002):216-223.
Pope et al. "Organ-Specific Regulation of the CD8 T Cell Response to *Listeria monocytogenes* Infection." *J. Immunol.* 166(2001):3402-3409.
Pouzet et al. "Factors Affecting Functional Outcome After Autologous Skeletal Myoblast Transplantation." *Ann. Thorac. Surg.* 71(2001):844-851.
Pulendran et al. "Flt3-Ligand and Granulocyte Colony-Stimulating Factor Mobilize Distinct Human Dendritic Cell Subsets In Vivo." *J. Immunol.* 165(2000):566-572.
Qu et al. "Development of Approaches to Improve Cell Survival in Myoblast Transfer Therapy." *J. Cell Biol.* 142.5(1998):1257-1267.
Qu-Petersen et al. "Identification of a Novel Population of Muscle Stem Cells in Mice: Potential for Muscle Regeneration." *J. Cell Biol.* 157.5(2002):851-864.
Quezada et al. "CTLA4 Blockade and GM-CSF Combination Immunotherapy Alters the Intratumor Balance of Effector and Regulatory T Cells." *J. Clin. Invest.* 116.7(2006):1935-1945.
Rajagopalan et al. "Regional Angiogenesis With Vascular Endothelial Growth Factor in Peripheral Arterial Disease: A Phase II Randomized, Double-Blind, Controlled Study of Adenoviral Delivery of Vascular Endothelial Growth Factor 121 in Patients With Disabling Intermittent Claudication." *Circulation.* 108.16(2003):1933-1938.
Randolph et al. "Migration of Dendritic Cell Subsets and Their Precursors." *Annu. Rev. Immunol.* 26(2008):293-316.
Rappolee et al. "Macrophage-Derived Growth Factors." *Curr. Top. Microbiol. Immunol.* 181(1992):87-140.
Rapraeger. "Syndecan-Regulated Receptor Signaling." *J. Cell. Biol.* 149.5(2000):995-998.
Reddy et al. "Exploiting Lymphatic Transport and Complement Activation in Nanoparticle Vaccines." *Nat. Biotechnol.* 25.10(2007):1159-1164.
Reimann et al. "Satellite Cells in Normal and Regenerated Soleus Muscles of mdx and Control Mice." *Eur. J. Neurosci.*10(1998):366. (Abstract #153.07).
Richards Grayson et al. "Multi-Pulse Drug Delivery From a Resorbable Polymeric Microchip Device." *Nat. Mater.* 2.11(2003):767-772.
Richardson et al. "Polymeric System for Dual Growth Factor Delivery." *Nat. Biotech.* 19.11(2001):1029-1034.
Riddle et al. "Role of Poly(lactide-co-glycolide) Particle Size on Gas-Foamed Scaffolds." *J. Biomater. Sci. Polym. Ed.* 15.12(2004):1561-1570.
Ridgway et al. "Inhibition of Dll4 Signalling Inhibits Tumour Growth by Deregulating Angiogenesis." *Nature.* 444.7122(2006):1083-1087.
Rinderknecht et al. "The Amino Acid Sequence of Human Insulin-Like Growth Factor I and its Structural Homology with Proinsulin." *J. Biol. Chem.* 253.8(1978):2769-2776.
Rosenberg et al. "Cancer Immunotherapy: Moving Beyond Current Vaccines." *Nat. Med.* 10.9(2004):909-915.
Roth et al. "SC68896, a Novel Small Molecule Proteasome Inhibitor, Exerts Antiglioma Activity In vitro and In vivo." *Clin. Cancer Res.*15.21(2009):6609-6618.
Rowlands et al. "Directing Osteogenic and Myogenic Differentiation of MSCs: Interplay of Stiffness and Adhesive Ligand Presentation." *Am. J. Physiol Cell Physiol.* 295(2008):1037-1044.

(56) References Cited

OTHER PUBLICATIONS

Rowley et al. "Alginate Type and RGD Density Control Myoblast Phenotype." *J. Biomed. Mater. Res.* 60.2(2002):217-233.
Rowley et al. "Biomaterials to Spatially Regulate Cell Fate." *Adv. Mater.* 14.12(2002):886-889.
Rowley. "Alginate Hydrogels as Synthetic Extracellular Matrix Materials." *Biomaterials.* 20.1(1999):45-53.
Rubin et al. "Dissociation of Heparan Sulfate and Receptor Binding Domains of Hepatocyte Growth Factor Reveals That Heparan Sulfate-c-Met Interaction Factilitates Signaling." *J. Biol. Chem.* 276.35(2001):32977-32983.
Ryten et al. "ATP Regulates the Differentiation of Mammalian Skeletal Muscle by Activation of a P2X5 Receptor on Satellite Cells." *J. Cell. Biol.* 158.2(2002):345-355.
Ryu et al. "The Construction of Three-Dimensional Micro-Fluidic Scaffolds of Biodegradable Polymers by Solvent Vapor Based Bonding of Micro-Molded Layers." *Biomaterials.* 28.6(2007):1174-1184.
Salvador et al. "Combination of Immune Stimulating Adjuvants With Poly(lactide-co-glycolide) Microspheres Enhances the Immune Response of Vaccines." *Vaccine.* 30.3(2011):589-596.
Sano et al. "Swift Development of Protective Effector Functions in Naive CD8+ T Cells Against Malaria Liver Stages." *J. Exp. Med.* 194.2(2001):173-179.
Sansonetti. "The Innate Signaling of Dangers and the Dangers of Innate Signaling." *Nat. Immunol.* 7.12(2006):1237-1242.
Saxena et al. "Skeletal Muscle Tissue Engineering Using Isolated Myoblasts on Synthetic Biodegradable Polymers: Preliminary Studies." *Tissue Eng.* 5.6(1999):525-532.
Schaefer et al. Innate mmunity in the Human Female Reproductive Tract: Antiviral Response of Uterine Epithelial Cells to TLR3 Agonist Poly(I:C). *J. Immunol.* 174(2005):992-1002.
Schijns et al. "Mice Lacking IL-12 Develop Polarized Th1 Cells During Viral Infection." *J. Immunol.* 160(1998):3958-3964.
Schnorrer et al. "The Dominant Role of CD8+ Dendritic Cells in Cross-Presentation is not Dictated by Antigen Capture." *PNAS.* 103.28(2006):10729-10734.
Schuler et al. "The Use of Dendritic Cells in Cancer Immunotherapy." *Curr. Opin. Immunol.* 15.2(2003):138-147.
Seale et al. "Pax7 Is Required for the Specification of Myogenic Satellite Cells." *Cell.* 102.6(2000):777-786.
Shakweh et al. "Design and Characterisation of Poly(lactide-co-glycolide) Small Particulate Systems for the Delivery of Immunostimulant CpG Oligonucleotide." *J. Nanosci. Nanotechnol.* 6.9-10(2006):2811-2820.
Shansky et al. "Letter to the Editor: A Simplified Method for Tissue Engineering Skeletal Muscle Organoids In Vitro." *In Vitro Cell. Dev. Biol.* 33(1997):659-661.
Sheehan et al. "Skeletal Muscle Satellite Cell Proliferation in Response to Members of the Fibroblast Growth Factor Family and Hepatocyte Growth Factor." *J. Cell. Physiol.* 181.3(1999):499-506.
Sheridan et al. "Bioabsorbable Polymer Scaffolds for Tissue Engineering Capable of Sustained Growth Factor Delivery." *J. Control. Release.* 64.1-3(2000):91-102.
Shi et al. "A Novel Toll-Like Receptor that Recognizes Vascular Stomatitis Virus." *J. Biol. Chem.* 286.6(2011):4517-4524.
Shortman et al. "Steady-State and Inflammatory Dendritic-Cell Development." *Nat. Rev. Immunol.* 7(2007):19-30.
Sick et al. "WNT and DKK Determine Hair Follicle Spacing Through a Reaction-Diffusion Mechanism." *Science.* 314.5804(2006):1447-1450.
Silva et al. "Spatiotemporal Control of Vascular Endothelial Growth Factor Delivery From Injectable Hydrogels Enhances Angiogenesis." *J. Thromb. Haemost.* 5.3(2007):590-598.
Skokos et al. "CD8-DCs Induce IL-12-Independent Th1 Differentiation Through Delta 4 Notch-Like Ligand in Response to Bacterial LPS." *J. Exp. Med.* 204.7(2007):1525-1531.
Skuk et al. "Efficacy of Myoblast Transplantation in Nonhuman Primates Following Simple Intramuscular Cell Injections: Toward Defining Strategies Applicable to Humans." *Exp. Neurol.* 175.1(2002):112-126.
Skuk et al. "Myoblast Transplantation: The Current Status of a Potential Therapeutic Tool for Myopathies." *J. Musc. Res. Cell. Motil.* 24.4-6(2003):285-300.
Smidsrød et al. "Alginate as Immobilization Matrix for Cells." *Trends Biotechnol.* 8.3(1990):71-78.
Sohier et al. "Critical Factors in the Design of Growth Factor Releasing Scaffolds for Cartilage Tissue Engineering." *Exp. Opin. Drug Deliv.* 5.5(2008):543-566.
Steinman et al. "Taking Dendritic Cells into Medicine." *Nature.* 449.7161(2007):419-426.
Storrie et al. "Sustained Delivery of Plasmid DNA From Polymeric Scaffolds for Tissue Engineering." *Adv. Drug Deliv. Rev.* 58.4(2006):500-514.
Straub et al. "Animal Models for Muscular Dystrophy Show Different Patterns of Sarcolemmal Distruption." *J. Cell Biol.* 139.2(1997):375-385.
Sun et al. "Sustained Vascular Endothelial Growth Factor Delivery Enhances Angiogenesis and Perfusion in Ischemic Hind Limb." *Pharm. Res.* 22.7(2005):1110-1116.
Takeshita et al. "Therapeutic Angiogenesis." *J. Clin. Invest.* 93.2(1994):662-670.
Tamura et al. "Immunotherapy of Tumors with Autologous Tumor-Derived Heat Shock Protein Preparations." *Science.* 278.3(1997):117-120.
Tatsumi et al. "HGF/SF Is Present in Normal Adult Skeletal Muscle and Is Capable of Activating Satellite Cells." *Dev. Biol.* 194.1(1998):114-128.
Thurston et al. "The Delta Paradox: DLL4 Blockade Leads to More Tumour Vessels but Less Tumour Growth." *Nat. Rev. Cancer.* 7.5(2007):327-331.
Tidball. "Inflammatory Cell Response to Acute Muscle Injury." *Med. Sci. Sports Exerc.* 27.7(1995):1022-1032.
Turing. "Discussion: Turing's Theory of Morphogenesis—It's Influence on Modelling Biological Pattern and Form." *Bull. Math. Biol.* 52.1-2(1990):119-159.
Turing. "The Chemical Basis of Morphogenesis." *Philosophical Transactions of the Royal Society of London. Series B.* 237.641(1952):37-72.
Uchida et al. "Immunization by Particle Bombardment of Antigen-Loaded poly-(DL-lactide-co-glycolide) Microspheres in Mice." *Vaccine.* 12(2006):2120-2130.
Urbanek et al. "Stem Cell Niches in the Adult Mouse Heart." *PNAS.* 103.24(2006):9226-9231.
van Duin et al. "Triggering TLR Signaling in Vaccination." *Trends Immunol.* 27.1(2006):49-55.
Vandenburgh et al. "Tissue-Engineered Skeletal Muscle Organoids for Reversible Gene Therapy." *Hum. Gene Ther.* 17(1996):2195-2200.
Vieira et al. "The Bulk of Endogenously Produced IgG2a is Eliminated From the Serum of Adult C57BL/6 Mice With a Half-Life of 6-8 Days." *Eur. J. Immunol.* 16.7(1986):871-874.
Vieira et al. "The Half-Lives of Serum Immunoglobulins in Adult Mice." *Eur. J. Immunol.* 18.2(1988):313-316.
Villadangos et al. "Intrinsic and Cooperative Antigen-Presenting Functions of Dendritic-Cell Subsets in vivo." *Nat. Rev. Immunol.* 7.7(2007):543-555.
Villadangos. "Presentation of Antigens by MHC Class II Molecules: Getting the Most Out of Them." *Molec. Immunol.* 38.5(2001):329-346.
von Dassow et al. "The Segment Polarity Network is a Robust Developmental Module." *Nature.* 406.6792(2000):188-192.
Wakim et al. "Dendritic Cell-Induced Memory T Cell Activation in Nonlymphoid Tissues." *Science.* 319(2008):198-202.
Waldron-Lynch et al. "Advances in Type 1 Diabetes Therapeutics: Immunomodulation and β-Cell Savage." *Endocrinol. Metab. Clin. North Am.* 38.2(2009):303-317.
Wan et al. "Peritoneal Macrophage Uptake, Pharmacokinetics and Biodistribution of Macrophage-Targeted PEG-fMLF (N-Formyl-

(56) References Cited

OTHER PUBLICATIONS

Methionyl-Leucyl-Phenylalanine) Nanocarriers for Improving HIV Drug Delivery." *Pharm. Res.* 24.11(2007):2110-2119.
Wang et al. "Biological Activity of Bevacizumab, a Humanized Anti-VEGF Antibody in vitro." *Angiogenesis.* 7.4(2004):335-345.
Wei et al. "Global Mapping of H3K4me3 and H3K27me3 Reveals Specificity in Plasticity in Lineage Fate Determination of Differentiating CD4+ T Cells." *Immunity.* 30.1(2009):155-167.
Wernig et al. "Function of Skeletal Muscle Tissue Formed After Myoblast Transplantation into Irradiated Mouse Muscles." *J. Physiol.* 522.2(2000):333-345.
White et al. "Leukemia Inhibitory Factor Enhances Regeneration in Skeletal Muscles After Myoblast Transplantation." *Musc. Nerve.* 24.5(2001):695-697.
World Health Organization. "Global Burden of Musculoskeletal Disease Revealed in new WHO Report." *Bull. World Health Organ.* 81.11(2003):853-854.
World Health Organization. "The World Health Report 2004: Changing History." *The World Health Report.* (2004):1-169.
Wright et al. "Muscle-Based Gene Therapy and Tissue Engineering for the Musculoskeletal System." *Drug Disc. Today.* 6.14(2001):728-733.
Yancopoulos et al. "Vascular-Specific Growth Factors and Blood Vessel Formation." *Nature.* 407.6801(2000):242-248.
Yuen et al. "Mimicking Nature by Codelivery of Stimulant and Inhibitor to Create Temporally Stable and Spatially Restricted Angiogenic Zones." *PNAS.* 107.42(2010):17933-17938.
Zammit et al. "Kinetics of Myoblast Proliferation Show That Resident Satellite Cells are Competent to Fully Regenerate Skeletal Muscle Fibers." *Exp. Cell Res.* 281.1(2002):39-49.
Zammit et al. "Muscle Satellite Cells Adopt Divergent Fates: A Mechanism for Self-Renewal?" *J. Cell Biol.* 166.3(2004):347-357.
Zeltinger et al. "Effect of Pore Size and Void Fraction on Cellular Adhesion, Proliferation, and Matrix Deposition." *Tissue Eng.* 7.5(2001):557-572.
Zhang et al. "A Comparative Study of the Antigen-Specific Immune Response Induced by Co-Delivery of CpG OGN and Antigen Using Fusion Molecules or Biodegradable Microparticles." *J. Pharma. Sci.* 98.12(2007):3283-3292.
Zhao et al. "Active Scaffolds for On-Demand Drug and Cell Delivery." *PNAS.* 108.1(2011):67-72.
Zhao et al. "Directed Cell Migration via Chemoattractants Released from Degradable Microspheres." *Biomat.* 26(2005):5048-5063.
Zhou et al. "Microstructure and Mechanical Properties of Poly(L-lactide) Scaffolds Fabricated by Gelatin Particle Leaching Method." *J. Appl. Polymer Sci.* 98(2005):1373-1379.
"Wound Management: Past, Present, and Future." *Clinicians' Pocket Guide to Chronic Wound Repair.* Mulder et al., eds. Springhouse, PA: Springhouse Corporation. (1998):85-90.
Alsberg et al. "Regulating Bone Formation via Controlled Scaffold Design." *J. Dent. Res.* 82.11(2003):903-908.
Anderson et al. "Biomaterial Microarrays: Rapid, Microscale Screening of Polymer-Cell Interaction." *Biomaterials.* 26.23(2005):4892-4897.
Anderson et al. "Nanoliter-Scale Synthesis of Arrayed Biomaterials and Application to Human Embryonic Stem Cells." *Nat. Biotechnol.* 22.7(2004):863-866.
Augst et al. "Alginate Hydrogels as Biomaterials." *Macromol. Biosci.* 6(2006):623-633.
Bachem et al. "Superior Antigen Cross-Presentation and XCR1 Expression Define Human CD11c+CD141+ Cells as Homologues of Mouse CD8+ Dendritic Cells." *J. Exp. Med.* 207.6(2010):1273-1281.
Balakrishna et al. "Structural Correlates of Antibacterial and Membrane-Permeabilizing Activities in Acylpolyamines." *Antimicrob. Agents Chemother.* 50.3(2006):852-861.
Bar-Cohen et al. "Electroactive Polymer Actuators and Sensors." *MRS Bullet.* 33.3(2008):173-181.

Beaucage et al. "The Functionalization of Oligonucleotides Via Phosphoramidite Derivatives." *Tetrahedron.* 49.10(1993):1925-1963.
Beebe et al. "Functional Hydrogel Structures for Autonomous Flow Control Inside Microfluidic Channels." *Nature.* 404(2000):588-590.
Bekiari et al. "Study of Poly(N,N-dimethylacrylamide)/CdS Nanocomposite Organic/Inorganic Gels." *Langmuir.* 20.19(2004):7972-7975.
Bergstraesser et al. "Stimulation and Inhibition of Human Mammary Epithelial Cell Duct Morphogenesis in vitro." *Proc. Assoc. Am. Physicians.* 108.2(1996):140-154.
Bouhadir et al. "Degradation of Partially Oxidized Alginate and its Potential Application for Tissue Engineering." *Biotechnol. Prog.* 17.5(2001):945-950.
Brinkmann et al. "Neutrophil Extracellular Traps Kill Bacteria." *Science.* 303.5663(2004):1532-1535.
Bryant et al. "Photo-Patterning of Porous Hydrogels for Tissue Engineering." *Biomater.* 28.19(2007):2978-2986.
Bürger et al. "Effect of VEGF and its Receptor Antagonist SU-5416, an Inhibitor of Angiogenesis, on Processing of the β-amyloid Precursor Protein in Primary Neuronal Cells Derived From Brain Tissue of Tg2576 Mice." *Int. J. Dev. Neurosci.* 28.7(2010):597-604.
Calvert. "Electroactive Polymer Gels." *Electroactive Polymer (EAP) Acutators as Artificial Muscle: Reality, Potential, and Challenges.* Bar-Cohen, ed. Bellingham, WA: Spie Press. (2004):151-170.
Calvert. "Gel Sensors and Actuators." *MRS Bullet.* 33.3(2008):207-212.
Chang. "Mouse Models for Studies of Retinal Degeneration and Diseases." *Methods Mol. Biol.* 935(2013):27-39.
Coulson et al. "Flow of Fluids through Granular Beds and Packed Columns." *Chemical Engineering.* New York: Pergamon Press. 2(1978):125-171.
Crameri et al. "Improved Green Fluorescent Protein by Molecular Evolution Using DNA Shuffling." *Nat. Biotechnol.* 14.3(1996):315-319.
Dar et al. "Optimization of Cardiac Cell Seeding and Distribution in 3D Porous Alginate Scaffolds." *Biotechnol. Bioeng.* 80(2002):305-312.
Doan et al. "Subcellular Localization of a Sporulation Membrane Protein is Achieved Through a Network of Interactions Along and Across the Septum." *Mol. Microbiol.* 55.6(2005):1767-1781.
Egholm et al. "Peptide Nucleic Acids (PNA). Oligonucleotide Analogues with an Achiral Peptide Backbone." *J. Am. Chem. Soc.* 114.5(1992):1895-1897.
Egholm et al. "PNA Hybridizes to Complementary Oligonucleotides Obeying the Watson-Crick Hydrogen-Bonding Rules." *Nature.* 365.6446(1993):566-568.
Falsey et al. "Peptide and Small Molecule Microarray for High Throughput Cell Adhesion and Functional Assays." *Bioconjug. Chem.* 12.3(2001):346-353.
Fischer et al. "A Brilliant Monomeric Red Fluorescent Protein to Visualize Cytoskeleton Dynamics in *Dictyostelium.*" *FEBS Lett.* 577.1-2(2004):227-232.
Fischer et al. "Visualizing Cytoskeleton Dynamics in Mammalian Cells Using a Humanized Variant of Monomeric Red Fluorescent Protein." *FEBS Lett.* 580.10(2006):2495-2502.
Fox. "Management of Worsening Multiple Sclerosis with Mitoxantrone: A Review." *Clin. Ther.* 28.4(2006):461-474.
GenBank Accession No. AAI44040, Mar. 18, 2009.
GenBank Accession No. CAG29322.1, Oct. 16, 2008.
GenBank Accession No. CAG33149.1, Oct. 21, 2008.
GenBank Accession No. EF064765.1, Nov. 13, 2006.
Glasbey et al. "Image Analysis and Three-Dimensional Modelling of Pores in Soil Aggregates." *Eur. J. Soil Sci.* 42.2(1991):479-486.
Gupta et al. "Magnetically Controlled Targeted Micro-Carrier Systems." *Life Sci.* 44.3(1989):175-186.
Heath. "Cells for Tissue Engineering." *Trends Biotechnol.* 18.1(2006):17-19.
Iwamoto et al. "Preparation of an Ionic Polymer Gel Microactuator and Measurement of its Periodic Motions." *Nippon Kagaku Kaishi.* 9(1997):609-614. (Japanese Original and English Abstract).

(56) References Cited

OTHER PUBLICATIONS

Jugdutt et al. "Aging and Defective Healing, Adverse Remodeling, and Blunted Post-Conditioning in the Reperfused Wounded Heart." *J. Am. Coll. Cardiol.* 51.14(2008):1399-1403.
Juntanon et al. "Electrically Controlled Release of Sulfosalicylic Acid from Crosslinked Poly(Vinyl Alcohol) Hydrogel." *Int. J. Pharm.* 356(2008):1-11.
Khownium et al. "Novel Endotoxin-Compounds with Terephthalaldehyde-bis-guanyllhydrazone Scaffolds." *Bioorg. Med. Chem. Lett.* 16(2006):1305-1308.
Kong et al. "Controlling Degradation of Hydrogels via the Size of Crosslinked Junctions." *Adv. Mater.* 16.21(2004):1917-1921.
Kong et al. "Decoupling the Dependence of Rheological/Mechanical Properties of Hydrogels from Solids Concentration." *Polymer.* 43(2002):6239-6246.
Kong et al. "Design of Biodegradable Hydrogel for the Local and Sustained Delivery of Angiogenic Plasmid DNA." *Pharma. Res.* 25.5(2008):1230-1238.
Kwon et al. "Electrically Erodible Polymer Gel for Controlled Release of Drugs." *Nature.* 354(1991):291-293.
Langenkamp et al. "Kinetics of Dendritic Cell Activation: Impact on Priming of TH1, TH2 and Nonpolarized T Cells." *Nat. Immunol.* 1.4(2000):311-316.
Lao et al. "Magnetic and Hydrogel Composite Materials for Hyperthermia Applications." *J. Mater. Sci. Mater. Med.* 15.10(2004):1061-1064.
Lauterbach et al. "Mouse CD8α+ DCs and Human BDCA3+ DCs are Major Producers of IFN-λ in Response to Poly IC." *J. Exp. Med.* 207.12(2010):2703-2717.
Leor et al. "Cells, Scaffolds, and Molecules for Myocardial Tissue Engineering." *Pharmacol. Therapeutics.* 105(2005):151-163.
Letsinger et al. "Phosphoramidate Analogs of Oligonucleotides." *J. Org. Chem.* 35.11(1970):3800-3803.
Liu et al. "Nanostructured Materials Designed for Cell Binding and Transduction." *Biomacromolecules.* 2.2(2001):362-368.
Lutolf et al. "Repair of Bone Defects Using Synthetic Mimetics of Collagenous Extracellular Matrices." *Nat. Biotechnol.* 21.5(2003):513-518.
López et al. "Magnetic Applications of Polymer Gels." *Macromol. Symp.* 166.1(2001):173-178.
Marui et al. "Simultaneous Application of Basic Fibroblast Growth Factor and Hepatocyte Growth Factor to Enhance the Blood Vessels Formation." *J. Vasc. Surg.* 41.1(2005):82-90.
Meier et al. "Peptide Nucleic Acids (PNAs)—Unusual Properties of Noionic Oligonucleotide Analogues." *Angew. Chem. Int. Ed.* 31.8(1992):1008-1010.
Melief et al. "Immunotherapy of Established (Pre)Malignant Disease by Synthetic Long Peptide Vaccines." *Nat. Rev. Cancer.* 8(2008):351-360.
Meraz et al. "Mesoporous Silicon Particles for the Presentation of Tumor Antigens and Adjuvant for Anti-Cancer Immunity." *Cancer Res.* 71.S24(2011):159s-160s. (Abstract #P1-01-12).
Miller et al. "Lipopolysaccharide Sequestrants: Structural Correlates of Activity and Toxicity in Novel Acylhomospermines." *J. Med. Chem.* 48(2005):2589-2599.
Miyata et al. "Biomolecule-Sensitive Hydrogels." *Adv. Drug Deliv. Rev.* 54.1(2002):79-98.
Mohan et al. "Novel Porous, Polysaccharide Scaffolds for Tissue Engineering Applications." *Trends Biomater. Artif. Organs.* 18.2(2005):219-224.
Murdan. "Electro-Responsive Drug Delivery from Hydrogels." *J. Control. Release.* 92(2003):1-17.
Nagai et al. "A Variant of Yellow Fluorescent Protein with Fast and Efficient Maturation for Cell-Biological Applications." *Nat. Biotechnol.* 20.1(2002):87-90.
NCBI Accession No. NM_004119, Apr. 14, 2013.
NCBI Accession No. NM_006274.2, Mar. 31, 2013.
Niamlang et al. "Electrically Controlled Release of Salicylic Acid from poly(p-phenylene vinylene) Polyacrylamide Hydrogels." *Int. J. Pharm.* 371(2009):126-133.
Orner et al. "Arrays for the Combinatorial Exploration of Cell Adhesion." *J. Am. Chem. Soc.* 126.35(2004):10808-10809.
Paradee et al. "Effects of Crosslinking Ratio, Model Drugs, and Electric Field Strength on Electrically Controlled Release for Alginate-Based Hydrogels." *J. Mater. Sci. Mater. Med.* 23(2012):999-1010.
Parker et al. "Effect of Mitoxantrone on Outcome of Children with First Relapse of Acute Lymphoblastic Leukemia (ALL R3): An Open-Label Radomised Trial." *Lancet.* 376(2010):2009-2017.
Pedersen et al. "Induction of Regulatory Dendritic Cells by Desamethasone and 1α,25-Dihydroxyvitamin D3." *Immunol. Lett.* 91(2004):63-69.
Pena et al. "Effects of TGF-β and TGF-β Neutralizing Antibodies on Fibroblast-Induced Collagen Gel Contraction: Implications for Proliferative Vitroretinpathy." *Invest. Ophthalmol. Vis. Sci.* 35.6(1994):2804-2808.
Porter et al. "Separation of Natural Populations of Coliform Bacteria from Freshwater and Sewage by Magnetic-Bead Cell Sorting." *J. Microbiol. Meth.* 33.3(1998):221-226.
Qui et al. "Environment-Sensitive Hydrogels for Drug Delivery." *Adv. Drug Deliv. Rev.* 53.3(2001):321-339.
Reis e Sousa. "Activation of Dendritic Cells: Translating Innate into Adaptive Immunity." *Curr. Opin. Immunol.* 16.1(3005):21-25.
Rizzo et al. "An Improved Cyan Fluorescent Protein Variant Useful for FRET." *Nat. Biotechnol.* 22.4(2004):445-449.
Salvay et al. "Inductive Tissue Engineering with Protein and DNA-Releasing Scaffolds." *Mol. Biosyst.* 2.1(2006):36-48.
Shaner et al. "Improved Monomeric Red, Orange and Yellow Fluorescent Proteins Derived from *Discosoma* sp. Red Fluorescent Protein." *Nat. Biotechnol.* 22.12(2004):1567-1572.
Silva et al. "Effects of VEGF Temporal and Spatial Presentation on Angiogenesis." *Biomaterials.* 31.6(2010):1235-1241.
Silva et al. "Material-Based Deployment Enhances Efficacy of Endothelial Progenitor Cells." *PNAS.* 105.38(2008):14347-14352.
Takahashi et al. "Induction of Pluripotent Stem Cells from Adult Human Fibroblasts by Defined Factors." *Cell.* 131.5(2007):861-872.
Tanaka et al. "Collapse of Gels in an Electric Field." *Science.* 218(1982):467-469.
ten Dijke et al. "Growth Factors for Wound Healing." *Nat. Biotechnol.* 7(1989):793-798.
Tomer et al. "Electrically Controlled Release of Macromolecules from Cross-Linked Hyaluronic Acid Hydrogels." *J. Control. Release.* 33.3(1995):405-413.
Tourniaire et al. "Polymer Microarrays for Cellular Adhesion." *Chem. Commun.* 20(2006):2118-2120.
Tsien. "The Green Fluorescent Protein." *Annu. Rev. Biochem.* 67(1998):509-544.
Wang et al. "Evolution of New Nonantibody Proteins via Iterative Somatic Hypermutation." *PNAS.* 101.48(2004):16745-16749.
Xie et al. "Preparation and Application of Surface-Coated Superparamagnetic Nanobeads in the Isolation of Genomic DNA." *J. Magn. Magnetic Mater.* 277.1(2004):16-23.
Yu et al. "Induced Pluripotent Stem Cell Lines Derived from Human Somatic Cells." *Science.* 318.5858(2007):1917-1920.
Yuk et al. "Electric Current-Sensitive Drug Delivery System Using Sodium Alginate/Polyacrylic Acid Composites." *Pharm. Res.* 9.7(1992):955-957.
Yang, Fan et al., "The effect of incorporating RGD adhesive peptide in polyethylene glycol diacrylate hydrogel on osteogenesis of bone marrow stromal cells," *Biomaterials,* vol. 26(2005):5991-5998.
De Jong et al. "Regulation of Notch Signaling Genes During BMP2-Induced Differentiation of Osteoblast Precursor Cells." *Biochem. Biophys. Res. Commun.*320(2004):100-107.
Liu et al. "Heterobifunctional Poly(Ethylene Glycol)-Tethered Bone Morphogenetic Protein-2-Stimulated Bone Marrow Mesenchymal Stromal Cell Differentiation and Osteogenesis." *Tissue Eng.* 13.5(2007):1113-1124.
Miljkovic et al. "Chondrogenesis, Bone Morphogenetic Protein-4 and Mesenchymal Stem Cells." *Osteoarthritis Cartilage.* 16(2008):1121-1130.
NCBI Accession No. NP_001193, May 3, 2014.

(56) References Cited

OTHER PUBLICATIONS

Holland et al. "Transforming Growth Factor-β1 Release from Oligo(poly(ethylene glycol)Fumarate) Hydrogels in Conditions that Model the Cartilage Wound Healing Environment." *J. Control. Release.* 94(2004):101-114.
"Collagen: The Fibrous Proteins of the Matrix." *Molecular Cell Biology.* Lodish et al., eds. New York: W.H. Freeman. Section 22.3(2000):979-985.
"Transient." Merriam-Webster Dictionary. Web. Jul. 18, 2014. www.merriam-webster.com/dictionary/transient.
Agache et al."Mechanical Properties and Young's Modulus of Human Skin in Vivo." *Arch. Dermatol. Res.* 269.3(1980):221-232.
Aguado et al. "Improving Viability of Stem Cells During Syringe Needle Flow Through the Design of Hydrogel Cell Carriers." *Tissue Eng. Part A.* 18.7-8(2012):806-815.
Akpalo et al. "Fibrin-Polyethylene Oxide Interpenetrating Polymer Networks: New Self-Supported Biomaterials Combining the Properties of Both Protein Gel and Synthetic Polymer." *Acta Biomater.* 7.6(2011):2418-2427.
American Diabetes Association. "Standards of Medical Care in Diabetes—2013." *Diabetes Care.* 36.S1(2013):S11-S66.
Annaidh et al. "Characterization of the Anistropic Mechanical Properties of Excised Human Skin." *J. Mech. Behav. Biomed. Mater.* 5.1(2012):139-148.
Aschner et al. "Metabolic Memory for Vascular Disease in Diabetes." *Diabetes Technol. Ther.* 14.S1(2012):S68-S74.
Aubin et al. "Directed 3D Cell Alignment and Elongation in Microengineered Hydrogels." *Biomater.* 31.27(2010):6941-6951.
Babensee et al. "Host Response to Tissue Engineered Device." *Adv. Drug Deli. Rev.* 33.1-2(1998):111-139.
Becker et al. "Cytological Demonstration of the Clonal Nature of Spleen Colonies Derived from Transplanted Mouse Marrow Cells." *Nature.* 197(1963):452-454.
Bell. "Models for the Specific Adhesion of Cells to Cells." *Science.* 200.4342(1978):618-627.
Bencherif et al. "Influence of Cross-Linker Chemistry on Release Kinetics of PEG-co-PGA Hydrogels." *J. Biomed. Mater. Res. A.* 90.1(2009):142-153.
Bencherif et al. "End-Group Effects on the Properties of PEG-co-PGA Hydrogels." *Acta Biomater.* 5.6(2009):1872-1883.
Bencherif et al. "Influence of the Degree of Methacrylation of Hyaluronic Acid Hydrogels Properties." *Biomater.* 29.12(2008):1739-1749.
Bencherif et al. "Injectable Preformed Scaffolds with Shape-Memory Properties." *PNAS.* 109.48(2012):19590-19595.
Bencherif et al. "Nanostructured Hybrid Hydrogels Prepared by a Combination of Atom Transfer Radical Polymerization and Free Radical Polymerization." *Biomater.* 30.29(2009):5270-5278.
Bencherif et al. "Synthesis by AFET ATRP of Degradable Nanogel Precursors for in situ Formation of Nanostructured Hyaluronic Acid Hydrogel." *Biomacromol.* 10.9(2009):2499-2507.
Benton et al. "Photocrosslinking of Gelatin Macromers to Synthesize Porous Hydrogels that Promote Valvular Interstitial Cell Function." *Tissue Eng. Part A.* 15.11(2009):3221-3230.
Berg et al. "IL-10 is a Central Regulator of Cyclooxygenase-2 Expression and Prostaglandin Production." *J. Immunol.* 166.4(2001):2674-2680.
Bianco et al. "The Meaning, the Sense and the Significance: Translating the Science of Mesenchymal Stem Cells into Medicine." *Nat. Med.* 19.1(2013):35-42.
Bilodeau et al. "Regular Pyramid Punch Problem." *J. Appl. Mech.* 59.3(1992):519-523.
Boateng et al. "Wound Healing Dressings and Drug Delivery Systems: A Review." *J. Pharm. Sci.* 97.8(2008):2892-2923.
Boerckel et al. "Mechanical Regulation of Vascular Growth and Tissue Regeneration in vivo." *PNAS.* 108.37(2011):E674-E680.
Boontheekul et al. "Controlling Alginate Gel Degradation Utilizing Partial Oxidation and Bimodal Molecular Weight Distribution." *Biomaterials.* 26.15(2005):2455-2465.

Brignone et al. "A Phase I Phamacokinetic and Biological Correlative Study of IMP321, a Novel MHC Class II Agonist, in Patients with Advanced Renal Cell Carcinoma." *Clin. Cancer Res.* 15.19(2009):6225-6231.
Broxmeyer et al. "Insights into the Biology of Cord Blood Stem/Progenitor Cells." *Cell Prolif.* 44.S1(2011):55-59.
Buckwalter et al. "Form of Antigen Dictates Immunity: Irradiated Cell vs. Whole Cell Lysate Vaccination." *J. Immunol.* 178(2007).
Bullard et al. "Fetal Wound Healing: Current Biology." *World J. Surg.* 27.1(2003):54-61.
Buonaguro et al. "Translating Tumor Antigens into Cancer Vaccines." *Clin. Vaccine Immunol.* 18.1(2011):23-34.
Burdick et al. "Controlled Degradation and Mechanical Behavior of Photopolymerized Hyaluronic Acid Networks." *Biomacromol.* 6.1(2005):386-391.
Burdick et al. "Photoencapsulation of Osteoblasts in Injectable RGD-Modified PEG Hydrogels for Bone Tissue Engineering." *Biomater.* 23.22(2002):4315-4323.
Bégué et al. "Vaccination Against Human Papillomavirus. Implementation and Efficacy Against Cervical Cancer Control." *Bull. Acad. Natl. Med.* 191.9(2007):1805-1816. (French original and English abstract).
Cameron et al. "The Influence of Substrate Creep on Mesenchymal Stem Cell Behaviour and Phenotype." *Biomater.* 32.26(2011):5979-5993.
Caulfield et al. "Regulation of Major Histocompatibility Complex Class II Antigens on Human Alveolar Macrophages by Granulocyte-Macrophage Colony-Stimulating Factor in the Presence of Glucocorticoids." *Immunol.* 98.1(1999):104-110.
Ceriello et al. "The 'Metabolic Meory': Is more than just Tight Glucose Control Necessary to Prevent Diabetic Complications?" *J. Clin. Endocrinol. Metab.* 94.2(2009):410-415.
Ceriello et al. "The Emerging Challenge in Diabetes: The 'Metabolic Memory.'" *Vascular Pharmacol.* 57.5-6(2012):133-138.
Chan et al. "Traction Dynamics of Filopodia on Compliant Substrates." *Science.* 322.5908(2008):1687-1691.
Chen et al. "Adipogenic Differentiation of Adipose Tissue-Derived Human Mesenchymal Stem Cells: Effects of Gastric Bypass Surgery." *Surg. Endosc.* 26(2012):3449-3456.
Chen et al. "Functional Human Vascular Network Generated in Photocrosslinkable Gelatin Methacrylate Hydrogels." *Adv. Fund. Mater.* 22.10(2012):2027-2039.
Chiang et al. "Whole Tumor Antigen Vaccines." *Semin. Immunol.* 22.3(2010):132-143.
Choi et al. "In Vitro Mineralization by Preosteoblasts in Poly(DL-lactide-co-glycolide) Inverse Opal Scaffolds Reinforced with Hydrozyapatite Nanoparticles." *Langmuir.* 26.14(2010):12126-12131.
Choi et al. "Three-Dimentional Scaffolds for Tissue Engineering: The Importance of Uniformity in Pore Size and Structure." *Langmuir.* 26.24(2010):19001-19006.
Chou et al. "Characterization of Photocross Linked Alginate Hydrogels for Nucleus Pulposus Cell Encapsulation." *J. Biomed. Mater. Res. A.* 91A.1(2009):187-194.
Clark et al. "Myosin II and Mechanotransduction: A Balancing Act." *Trends Cell Biol.* 17.4(2007):178-186.
Comisar et al. "Engineering RGD Nanopatterned Hydrogels to Control Preosteoblast Behavior: A Combined Computational and Experimental Approach." *Biomaterials.* 28(2007):4409-4417.
Cook et al. "A Sialomucopeptide Liberated by Trypsin from the Human Erythrocyte." *Nature.* 188(1960):1011-1012.
Cooper. "Metabolic Memory: Implications for Diabetic Vascular Complications." *Pediatr. Diabetes.* 10.5(2009):343-346.
Cuda et al. "In Vitro Actin Filament Sliding Velocities Produced by Mixtures of Different Types of Myosin." *Biophys. J.* 72.4(1997):1767-1779.
Cukierman et al. "Taking Cell-Matrix Adhesions to the Third Dimension." *Science.* 294.5547(2001):1708-1712.
David et al. "The in vitro Desensitization of Sensitive Cells by Trypsin." *J. Exp. Med.* 120(1964):1189-1200.
Davies et al. "Antibody-Antigen Complexes." *Annu. Rev. Biochem.* 59(1990):439-473.

(56) References Cited

OTHER PUBLICATIONS

Dembo et al. "Stresses at the Cell-to-Substrate Interface During Locomotion of Fibroblasts." *Biophys. J.* 76.4(1999):2307-2316.
Dexter et al. "Conditions Controlling the Proliferation of Haemopoietic Stem Cells In Vitro." *J. Cell. Physiol.* 91.3(1977):335-344.
Di Nicola et al. "Human Bone Marrow Stromal Cells Suppress T-Lymphocyte Proliferation Induced by Cellular or Nonspecific Mitogenic Stimuli." *Blood.* 99.10(2002):3838-3843.
Diduch et al. "Two Cell Lines from Bone Marrow tht Differ in Terms of Collagen Synthesis, Osteogenic Characteristics, and Matrix Mineralization." *J. Bone Joint Surg. Am.* 75.1(1993):92-105.
Diridollou et al. "Skin Ageing: Changes of Physical Properties of Human Skin in vivo." *J. Cosmet. Sci.* 23.6(2001):353-362.
Discher et al. "Tissue Cells Feel and Respond to the Stiffness of their Substrate." *Science.* 310.5751(2005):1139-1143.
Disis et al. "Granulocyte-Macrophage Colony-Stimulating Factor: An Effective Adjuvant for Protein and Peptide-Based Vaccines." *Blood.* 88.1(1996):202-210.
Donati et al. "New Hypothesis on the Role of Alternating Sequences in Calcium-Alginate Gels." *Biomacromol.* 6.2(2005):1031-1040.
Douay et al. "Ex vivo Production of Human Red Blood Cells from Hematopoietic Stem Cells: What is the Future in Transfusion?" *Transfus. Med. Rev.* 21.2(2007):91-100.
Dranoff. "GM-CSF-Based Cancer Vaccines." *Immunol. Rev.* 188(2002):147-154.
DuFort et al. "Balancing Forces: Architectural Control of Mechanotransduction." *Nat. Rev. Mol. Cell Biol.* 12.5(2011):308-319.
Dupont et al. "Role of YAP/TAZ in Mechanotransduction." *Nature.* 474.7350(2011):179-183.
Edwards et al. "Evaluation of Biomechanical Properties of Human Skin." *Clin. Dermatol.* 13.4(1995):375-380.
Eming et al. "Inflammation in Wound Repair: Molecular and Cellular Mechanisms." *J. Invest. Dermatol.* 127.3(2007):514-525.
Engler et al. "Microtissue Elasticity: Measurements by Atomic Force Microscopy and its Influence on Cell Differentiation." *Methods Cell. Biol.* 83(2007):521-545.
Engler et al. "Substrate Compliance Versus Ligand Density in Cell on Gel Response." *Biophys. J.* 86.1Pt1(2004):617-628.
Exposito et al. "The Fibrallar Collagen Family." *Int. J. Mol. Sci.* 11.2(2010):407-426.
Falanga. "Wound Healing and its Impairment in the Diabetic Foot." *Lancet.* 366.9498(2005):1736-1743.
Fauquemberque et al. "HLA-A0201-Restricted CEA-Derived Peptide CAP1 is not a Suitable Target for T-Cell-Based Immunotherapy." *J. Immunother.* 33.4(2010):402-413.
Fisher et al. "The Study of Protein Mechanics with the Atomic Force Microscope." *Trends Biochem. Sci.* 24.10(1999):379-384.
Friedenstein et al. "Fibroblast Precursors in Normal and Irradiated Mouse Hematopoietic Organs." *Exp. Hematol.* 4.5(1976):267-274.
Gardel et al. "Traction Stress in Focal Adhesions Correlates Biphasically with Actin Retrograde Flow Speed." *J. Cell Biol.* 183.6(2008):999-1005.
Gasic et al. "Removal and Regeneration of the Cell Coating in Tumour Cells." *Nature.* 196(1962):170.
Gauthier et al. "Temporary Increase in Plasma Membrane Tension Coordinates the Activation of Exocytosis and Contraction During Cell Spreading." *PNAS.* 108.35(2011):14467-14472.
Geerligs et al. "Linear Viscoelastic Behavior of Subcutaneous Adipose Tissue." *Biorheol.* 45.6(2008):677-688.
GenBank Accession No. AAA36738.1, Aug. 3, 1993.
GenBank Accession No. AAA60022.1, Jan. 7, 1995.
GenBank Accession No. AAA64239.1, Mar. 23, 1995.
GenBank Accession No. AAB18786.3, Jul. 12, 1999.
GenBank Accession No. AAH94877.1, May 20, 2005.
GenBank Accession No. AEO22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01955.1, Nov. 14, 2006.
GenBank Accession No. DQ103757.1, Jul. 25, 2005.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. NM_000091.4, May 10, 2014.
GenBank Accession No. NM_000572.2, May 18, 2014.
GenBank Accession No. NM_000638.3, May 4, 2014.
GenBank Accession No. NM_000758.3, May 4, 2014.
GenBank Accession No. NM_000885.4, Apr. 13, 2014.
GenBank Accession No. NM_000963.3, Jun. 13, 2014.
GenBank Accession No. NM_001001522.1, May 18, 2014.
GenBank Accession No. NM_001845.4, May 3, 2014.
GenBank Accession No. NM_001901.2, May 18, 2014.
GenBank Accession No. NM_002421.3_May 11, 2014.
GenBank Accession No. NM_002982.3, May 3, 2014.
GenBank Accession No. NM_003377.4, May 5, 2014.
GenBank Accession No. NM_003392.4, May 5, 2014.
GenBank Accession No. NM_004469.4, May 25, 2014.
GenBank Accession No. NM_005429.3, Mar. 31, 2014.
GenBank Accession No. NM_015719.3, Feb. 26, 2014.
GenBank Accession No. NP_000082.2, May 10, 2014.
GenBank Accession No. NP_000629.3, May 4, 2014.
GenBank Accession No. NP_000749.2, May 4, 2014.
GenBank Accession No. NP_000876.3, Apr. 13, 2014.
GenBank Accession No. NP_000954.1, Jun. 13, 2014.
GenBank Accession No. NP_001001522.1, May 18, 2014.
GenBank Accession No. NP_001836.2, May 3, 2014.
GenBank Accession No. NP_001892.1, May 18, 2014.
GenBank Accession No. NP_002973.1, May 3, 2014.
GenBank Accession No. NP_003239.2, Feb. 18, 2014.
GenBank Accession No. NP_003368.1, May 5, 2014.
GenBank Accession No. NP_003383.2, May 5, 2014.
GenBank Accession No. NP_004460.1, May 25, 2014.
GenBank Accession No. NP_005420.1, May 11, 2014.
GenBank Accession No. NP_056534.2, Feb. 26, 2014.
GenBank Accession No. U76381.2, Jul. 12, 1999.
Genes et al. "Effect of Substrate Mechanics on Chondrocyte Adhesion to Modified Alginate Surfaces." *Arch. Biochem. Biophys.* 422.2(2004):161-167.
Graessley. "Entangled Linear, Branched and Network Polymer Systems—Molecular Theories." *Adv. Poly. Sci.* 47(1982):67-117.
Guillaume et al. "Two Abundant Proteasome Subtypes that Uniquely Process Some Antigens Presented by HLA Class I Molecules." *PNAS.* 107.43(2010):18599-18604.
Guo et al. "Droplet Microfluidics for High-Throughput Biological Assays." *Lab Chip.* 12.12(2012):2146-2155.
Gurkan et al. "The Mechanical Environment of Bone Marrow: A Review." *Ann. Biomed. Eng.* 36.12(2008):1978-1991.
Halim et al. "Biologic and Synthetic Skin Substitutes: An Overview." *Indian J. Plast. Surg.* 43(2010):S23-S28.
Harris. "Classification, Diagnostic Criteria, and Screening for Diabetes." *Diabetes in America.* NIH Publication No. 95-1468. Chapter 2. (1995):15-36.
Humphries et al. "Integrin Ligands at a Glance." *J. Cell. Sci.* 119.Pt19(2006):3901-3903.
Huston et al. "Protein Engineering of Antibody Binding Sites: Recovery of Specific Activity in an Anti-Digoxin Single-Chain Fv Analogue Produced in *Escherichia coli.*" *PNAS.* 85.16(1988):5879-5883.
Hutson et al. "Synthesis and Characterization of Tunable Poly(ethylene Glycol): Gelatin Methacrylate Composite Hydrogels." *Tissue Eng. Part A.* 17.13-14(2011):1713-1723.
Hwang et al. "Fabrication of Three-Dimensional Porous Cell-Laden Hydrogel for Tissue Engineering." *Biofabrication.* 2.3(2010):035003.
Ihnat et al. "Hypothesis: The 'Metabolic Memory', the New Challenge of Diabetes." *Diabet. Med.* 24.6(2007)582-586.

(56) References Cited

OTHER PUBLICATIONS

Isern et al. "Self-Renewing Human Bone Marrow Mesenspheres Promote Hematopoietic Stem Cell Expansion." *Cell Rep.* 3.5(2013):1714-1724.
Janmey et al. "From Tissue Mechanics to Transcription Factors." *Differentiation.* 86.3(2013):112-120.
Jiang et al. "Two-Piconewton Slip Bond Between Fibronectin and the Cytoskeleton Depends on Talin." *Nature.* 424.6946(2003):334-337.
Jokinen et al. "Integrin-Mediated Cell Adhesion to Type I Collagen Fibrils." *J. Biol. Chem.* 279.30(2004):31956-31963.
Kang et al. "Effect of Porous Structure on the Degradation of Freeze-Dried Gelatin Hydrogels." *J. Bioact. Compat. Poly.* 14.4(1999):331-343.
Katayama et al. "Integrated Analysis of the Genome and the Transcriptome by FANTOM." *Brief Bioinform.* 5.3(2004):249-258.
Kearney et al. "Macroscale Delivery Systems for Molecular and Cellular Payloads." *Nat. Mater.* 12.11(2013):1004-10017.
Kennedy et al. "Rapid and Extensive Collapse from Electrically Responsive Macroporous Hydrogels." *Adv. Healthc. Mater.* 3.4(2014):500-507.
Khetan et al. "Degradation-Mediated Cellular Traction Directs Stem Cell Fate in Covalently Crosslinked Three-Dimensional Hydrogels." *Nat. Mater.* 12.5(2013):458-465.
Kim et al. "Multifunctional Capsule-in-Capsules for Immunoprotection and Trimodal Imaging." *Angew. Chem. Int. Ed.* 50.10(2011):2317-2321.
Klein et al. "Cell-Cycle Control by Physiological Matrix Elasticity and In Viivo Tissue Stiffening." *Curr. Biol.* 19.18(2009):1511-1518.
Kohane. "Microparticles and Nanoparticles for Drug Delivery." *Biotechnol. Bioeng.* 96.2(2007):203-209.
Kong et al. "FRET Measurements of Cell-Traction Forces and Nano-Scale Clustering of Adhesion Ligands Varied by Substrate Stiffness." *PNAS.* 102.12(2005):4300-4305.
Kratky et al. "Direct Activation of Antigen-Presenting Cells is Required for CD8+ T-Cell Priming and Tumor Vaccination." *PNAS.* 108.42(2011):17414-17419.
Kuwahara et al. "Cell Delivery Using an Injectable and Adhesive Transglutaminase-Gelatin Gel." *Tissue Eng. Part C Methods.* 16.4(2010):609-618.
Lee et al. "Intravenous hMSCs Improve Myocardial Infarction in Mice because Cells Embolized in Lung are Activated to Secrete the Anti-Inflammatory Protein TSG-6." *Cell Stem Cell.* 5.1(2009):54-63.
Lee et al. "Engineering Liver Tissue Spheroids with Inverted Colloidal Crystal Scaffolds." *Biomater.* 30.27(2009):4687-4694.
Lele et al. "Investigating Complexity of Protein-Protein Interactions in Focal Adhesions." *Biochem. Biophys. Res. Commun.* 369.3(2008):929-934.
Levental et al. "Soft Biological Materials and their Impact on Cell Function." *Soft Matter.* 3(2007):299-306.
Li et al. "A Novel Cyclohexene Derivate, Ethyl (6R)-6-[N-(2-Chloro-4-fluorophenyl)sulfamoyl]cyclohex-1-ene-1-carboxylate (TAK-242), Selectively Inhibits Toll-Like Receptor 4-Mediated Cytokine Production Through Suppression of Intracellular Signaling." *Mol. Pharmacol.* 69.4(2006):1288-1295.
Li et al. "Purified Hybrid Cells from Dendritic Cell and Tumor Cell Fusions are Superior Activators of Antitumor Immunity." *Cancer Immunol. Immunother.* 50.9(2001):456-462.
Lin et al. "Transdermal Regulation of Vascular Network Bioengineering Using a Photopolymerizable Methacrylated Gelatin Hydrogel." *Biomater.* 34.28(2013):6785-6796.
Liu et al. "On the Viscoelastic Character of Liver Tissue: Experiments and Modelling of the Linear Behaviour." *Biorheol.* 37.3(2000):191-201.
Lo et al. "Cell Movement is Guided by the Rigidity of the Substrate." *Biophys. J.* 79.1(2000):144-152.
Ludewig et al. "Immunotherapy with Dendritic Cells Directed Against Tumor Antigens Shared with Normal Host Cells Results in Severe Autoimmune Disease." *J. Exp. Med.* 191.5(2000):795-804.

Majeti et al. "Identification of a Hierarchy of Multipotent Hematopoietic Progenitors in Human Cord Blood." *Cell Stem Cell.* 1.6(2007):635-645.
Malmqvist. "Biospecific Interaction Analysis Using Biosensor Technology." *Nature.* 361.6408(1993):186-187.
Mammoto et al. "Mechanical Control of Tissue and Organ Development." *Development.* 137.9(2010):1407-1420.
Manavski et al. "Vascular Niche Controls Organ Regeneration." *Circ. Res.* 114.17(2014):1077-1079.
Mansoor et al. "Engineering T Cells for Cancer Therapy." *Br. J. Cancer.* 93.10(2005):1085-1091.
Masedunskas et al. "Role for the Actomyosin Complex in Regulated Exocytosis Revealed by Intravital Microscopy." *PNAS.* 108.33(2011):13552-13557.
McDonald et al. "Early Fracture Callus Displays a Smooth Muscle-Like Viscoelastic Properties Ex Viivo: Implications for Fracture Healing." *J. Orthop. Res.* 27.11(2009):1508-1513.
McKinnon et al. "Biophysically Defined and Cytocompatible Covalently Adaptable Networks as Viscoelastic 3D Cell Culture Systems." *Adv. Mater.* 26.6(2014):865-872.
McWhorter et al. "Modulation of Macrophage Phenotype by Cell Shape." *PNAS.* 110.43(2013):17253-17258.
Merkel et al. "Using Mechanobiological Mimicry of Red Blood Cells to Extend Circulation Times of Hydrogel Microparticles." *PNAS.* 108.2(2011):586-591.
Metters et al. "Fundamental Studies of Biodegradable Hydrogels as Cartilage Replacement Materials." *Biomed. Sci. Instrum.* 35(1999):33-38.
Miller et al. "Melanoma." *N. Engl. J. Med.* 355.1(2006):51-65.
Miralles et al. "Actin Dynamics Control SRF Activity by Regulation of its Coactivator MAL." *Cell.* 113.3(2003):329-342.
Molinari et al. "Modification of Surface Membrane Antigens by Trypsin." *Proc. Soc. Exp. Biol. Med.* 148.4(1975):991-994.
Molloy et al. "Movement and Force Produced by a Single Myosin Head." *Nature.* 378.6553(1995):209-212.
Mooney et al. "Cytoskeletal Filament Assembly and the Control of Cell Spreading and Function by Extracellular Matrix." *J. Cell Sci.* 108(1995):2311-2320.
Muralidharan-Chari et al. "ARF6-Regulated Shedding of Tumor Cell-Derived Plasma Membrane Microvesicles." *Curr. Biol.* 19.22(2009):1875-1885.
NCBI Accession No. NM_001561.5, Mar. 16, 2014.
NCBI Accession No. NM_004448.3, Apr. 23, 2014.
NCBI Accession No. NM_005018.2, Apr. 27, 2014.
NCBI Accession No. NM_181780.3, Jan. 27, 2014.
NCBI Accession No. NP_001552.2, Mar. 16, 2014.
NCBI Accession No. NP_003237.2, May 25, 2014.
NCBI Accession No. NP_003318.1, May 4, 2014.
NCBI Accession No. NP_003327.3, May 4, 2014.
NCBI Accession No. NP_005009.2, Apr. 27, 2014.
NCBI Accession No. NP_861445.3, Jan. 27, 2014.
Nichol et al. "Cell-Laden Microengineered Gelatin Methacrylate Hydrogels." *Biomater.* 31.21(2010):5536-5544.
Nicodemus et al. "Cell Encapsulation in Biodegradable Hydrogels for Tissue Engineering Applications." *Tissue Eng. Part B Rev.* 14.2(2008):149-165.
Niessen et al. "The α6β4 Integrin is a Receptor for Both Lamin and Kalinin." *Exp. Cell Res.* 211.2(1994):360-367.
Osunkoya et al. "Synthesis and Fate of Immunological Surface Receptors on Cultured Burkitt Lymphoma Cells." *Int. J. Cancer.* 4.2(1969):159-165.
Page-McCaw et al. "Matrix Metalloproteinases and the Regulation of Tissue Remodelling." *Nat. Rev. Mol. Cell Biol.* 8.3(2007):221-233.
Pailler-Mattei et al. "In vivo Measurements of the Elastic Mechanical Properties of Human Skin by Indentation Tests." *Med. Eng. Phys.* 30.5(2008):599-606.
Pardoll. "The Blockade of Immune Checkpoints in Cancer Immunotherapy." *Nat. Rev. Cancer.* 12.4(2012):252-264.
Parekh et al. "Modulus-Driven Differentiation of Marrow Stromal Cells in 3D Scaffolds that is Independent of Myosin-Based Cytoskeletal Tension." *Biomater.* 32.9(2011):2256-2264.

(56) References Cited

OTHER PUBLICATIONS

Parekkadan et al. "Mesenchymal Stem Cell-Derived Molecules Reverse Fulminant Hepatic Failure." *PLoS One.* 2.9(2007):e941.
Park et al. "Photopolymerized Hyaluronic Acid-Based Hydrogels and Interpenetrating Networks." *Biomater.* 24.6(2003):893-900.
Pawlaczyk et al. "Age-Dependent Biomechanical Properties of the Skin." *Postepy. Dermatol. Alergol.* 30.5(2013):302-306.
Pek et al. "The Effect of Matrix Stiffness on Mesenchymal Stem Cell Differentiation in a 3D Thixotropic Gel." *Biomater.* 31.3(2010):385-391.
Peyton et al. "The Use of Poly(ethylene glycol) Hydrogels to Investigate the Impact of ECM Chemistry and Mechanics on Smooth Muscle Cells." *Biomater.* 27.28(2006):4881-4893.
Pinho et al. "PDGFRα and CD51 Mark Human Nestin+ Sphere-Forming Mesenchymal Stem Cells Capable of Hematopoietic Progenitor Cell Expansion." *J. Exp. Med.* 210.7(2013):1351-1367.
Qi et al. "Patterned Differentiation of Individual Embryoid Bodies in Spatially Organized 3D Hybrid Microgels." *Adv. Mater.* 22.46(2010):5276-5281.
Qin et al. "Soft Lithography for Micro- and Nanoscale Patterning." *Nat. Protoc.* 5.3(2010):491-502.
Raeber et al. "Molecularly Engineered PEG Hydrogels: A Novel Model System for Proteolyrically Mediated Cell Migration." *Biophys. J.* 89.2(2005):1374-1388.
Ramón-Azcón et al. "Gelatin Methacrylate as a Promising Hydrogel for 3D Microscale Organization and Proliferation of Dielectroretically Patterned Cells." *Lab on a Chip.* 12.16(2012):2959-2969.
Ranganath et al. "Harnessing the Mesenchymal Stem Cell Secretome for the Treatment of Cardiovascular Disease." *Cell Stem Cell.* 10.3(2012):244-258.
Raposo et al. "Extracellular Vesicles: Exosomes, Microvesicles, and Friends." *J. Cell. Biol.* 200.4(2013):373-383.
Roccaro et al. "BM Mesenchymal Stromal Cell-Derived Exosomes Facilitate Multiple Myeloma Progression." *J. Clin. Invest.* 123.4(2013):1542-1555.
Rodriguez et al. "Minimal 'Self' Peptides that Inhibit Phagocytic Clearance and Enhance Delivery of Nanoparticles." *Science.* 339.6122(2013):971-975.
Sacchetti et al. "Self-Renewing Osteoprogenitors in Bone Marrow Sinusoids can Organize a Hematopoietic Microenvironment." *Cell.* 131.2(2007):324-336.
Sakai et al. "An Injectable, in situ Enzymatically Gellable, Gelatin Derivative for Drug Delivery and Tissue Engineering." *Biomater.* 30.20(2009):3371-3377.
Salem et al. "Defining the Antigen-Specific T-Cell Response to Vaccination and Poly(I:C)/TLR3 Signaling." *J. Immunother.* 28.3(2005):220-228.
Sarkar et al. "Condensation of Oligonucleotides Assembled into Nicked and Gapped Duplexes: Potential Structures for Oligonucleotide Delivery." *Nucleic Acids Res.* 33.1(2005):143-151.
Scheel et al. "Toll-Like Receptor-Dependent Activation of Several Human Blood Cell Types by Protamine Condensed mRNA." *Eur. J. Immunol.* 35(2005):1557-1566.
Schofield. "The Relationship Between the Spleen Colony-Forming Cell and the Haemopoietic Stem Cell." *Blood. Cells.* 4.1-2(1978):7-25.
Schwartz. "Integrins and Extracellular Matrix in Mechanotransduction." *Cold Spring Harb. Perspect. Biol.* 2.12(2010):a005066.
Sensi et al. "Unique Tumor Antigens: Evidence for Immune Control of Genome Integrity and Immunogenic Targets for T Cell-Mediated Patient-Specific Immunotherapy." *Clin. Cancer Res.* 12.17(2006):5023-5032.
Shi et al. "Granulocyte-Macrophage Colony-Stimulating Factor (GM-CSF) and T-Cell Responses: What we do and don't know." *Cell Res.* 16.2(2006):126-133.
Shin et al. "Contractile Forces Sustain and Polarize Hematopoiesis from Stem and Progenitor Cells." *Cell Stem Cell.* 14.1(2014):81-93.
Shin et al. "Lamins Regulate Cell Trafficking and Lineage Maturation of Adult Human Hematopoetic Cells." *PNAS.* 110.47(2013):18892-18897.
Shin et al. "Myonsin-II Inhibition and Soft 2D Matrix Maximize Multinucleation and Cellular Projections Typical of Platelet-Producing Megakaryocytes." *PNAS.* 108.28(2011):11458-11463.
Siegwart et al. "Synthesis, Characterization, and in vitro Cell Culture Viability of Degradable Poly(N-isopropylacrylamide-co-5,6-benzo-2-methylene-1,3-dioxepane)-Based Polymers and Cross-linked Gels." *J. Biomed. Mater. Res. A.* 87.2(2008):345-358.
Singer et al. "Cutaneous Wound Healing." *N. Engl. J. Med.* 341.10(1999):738-746.
Solon et al. "Fibroblast Adaptation and Stiffness Matching to Soft Elastic Substrates." *Biophys. J.* 93.12(2007):4453-4461.
Stachowiak et al. "Inverse Opal Hydrogel-Collagen Composite Scaffolds as a Supportive Microenvironment for Immune Cell Migration." *J. Biomed. Mater. Res.* 85A(2008):815-828.
Sun et al. "Biomimetic Interpenetrating Polymer Network Hydrogels Based on Methacrylated Alginate and Collagen for 3D Pre-Osteoblast Spreading and Osteogenic Differentiation." *Soft Matter.* 8(2012):2398-2404.
Sun et al. "Highly Stretchable and Tough Hydrogels." *Nature.* 489.7414(2012):133-136.
Suri et al. "Photopatterned Collagen-Hyaluronic Acid Interpenetrating Polymer Network Hydrogels." *Acta Biomater.* 5.7(2009):2385-2397.
Swift et al. "Nuclear Lamin-A Scales with Tissue Stiffness and Enhances Matrix-Directed Differentiation." *Science.* 341.6149(2013):1240104.
Syed et al. "Stem Cell Therapy Market." *Nat. Rev. Drug Discov.* 12.3(2013):185-186.
Tabata et al. "Enhanced Vascularization and Tissue Granulation by Basic Fibroblast Growth Factor Impregnated in Gelatin Hydrogels." *J. Control. Release.* 31.2(1994):189-199.
Tannous. "*Gaussia* Luciferase Reporter Assay for Monitoring Biological Processes in Culture and in vivo." *Nat. Protoc.* 4.4(2009):582-591.
Thomas et al. "Intravenous Infusion of Bone Marrow in Patients Receiving Radiation and Chemotherapy." *N. Engl. J. Med.* 257.11(1957):491-496.
Thurner et al. "Vaccination with Mage-3A1 Peptide-Pulsed Mature, Monocyte-Derived Dendritic Cells Expands Specific Cytotoxic T Cells Induces Regression of Some Metastases in Advanced Stage IV Melanoma." *J. Exp. Med.* 190.11(1999):1669-1678.
Tong et al. "Engineering Interpenetrating Network Hydrogels as Biomimetic Cell Niche with Independently Tunable Biochemical and Mechanical Properties." *Biomater.* 35.6(2014):1807-1815.
Trappmann et al. "Extracelluar-Matrix Tethering Regulates Stem-Cell Fate." *Nat. Mater.* 11.7(2012):642-649.
Trappmann et al. "How Cells Sense Extracellular Matrix Stiffness: A Material's Perspective." *Curr. Opin. Biotechnol.* 24.5(2013):948-953.
Ugarte et al. "Notch Signaling Enhances Osteogenic Differentiation While Inhibiting Adipogenesis in Primary Human Bone Marrow Stromal Cells." *Exp. Hematol.* 37(2009):867-875.
Uhlenbruck. "Action of Proteolytic Enzymes on the Human Erythrocyte Surface." *Nature.* 190(1961):181.
Ulrich et al. "Probing Cellular Mechanobiology in Three-Dimensional Culture with Collagen-Agarose Matrices." *Biomater.* 31.7(2010):1875-1884.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.

(56) References Cited

OTHER PUBLICATIONS

UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
van der Bruggen et al. "T Cell-Defined Tumor Antigens." *Cancer Immunity*. (2013). Http:www.cancerimmunity.org/peptide.
Venturoni et al. "Investigations into the Polymorphism of Rat Tail Tendon Fibrils Using Atomic Force Microscopy." *Biochem. Biophys. Res. Commun*. 303.2(2003):508-513.
Vincent et al. "Stem Cell Differentiation: Post-Degradation Forces Kick in." *Nat. Mater*. 12.5(2013):384-386.
Vogel et al. "Local Force and Geometry Sensing Regulate Cell Functions." *Nat. Rev. Mol. Cell Biol*. 7.4(2006):265-275.
Wang et al. "Mechanotransduction at a Distance: Mechanically Coupling the Extracellular Matric with the Nucleus." *Nat. Rev. Mol. Cell. Biol*. 10.1(2009):75-82.
Wang-Gillam et al. "A Phase I Study of IMP321 and Gemcitabine as the Front-Line Therapy in Patients with Advanced Pancreatic Adenocarcinoma." *Invest. New Drugs*. 31.3(2013):707-713.
Warner et al. "Cyclooxygenases: New Forms, New Inhibitors, and Lessons from the Clinic." *FASEB J*. 18.7(2004):790-804.
Weisenberger et al. "Comprehensive DNA Methylation Analysis on the Illumina® Infinium® Assay Platform." Illumina, Inc. Mar. 25, 2008. Web.
Weiss et al. "The Demonstration of Rupture of Cell Surfaces by an Immunological Technique." *Exp. Cell Res*. 30(1963):331-338.
Wen et al. "Mechanically Robust Gelatin-Alginate IPN Hydrogels by a Combination of Enzymatic and Ionic Crosslinking Approaches." *Macromol. Mater. Eng*. 299(2013):504-513.
Wieland et al. "Engineering Molecular Circuits Using Synthetic Biology in Mammalian Cells." *Annu. Rev. Chem. Biomol. Eng*. 3(2012):209-234.
Wipff et al. "Myofibroblast Contraction Activates Latent TGF-$\beta$1 from the Extracellular Matrix." *J. Cell Biol*. 179.6(2007):1311-1323.
Wong et al. "Focal Adhesion Kinase Links Mechanical Force to Skin Fibrosis via Inflammatory Signaling." *Nat. Med*. 18.1(2011):148-152.
Wong et al. "Mechanical Force Prolongs Acute Inflammation via T-Cell-Dependent Pathways During Scar Formation." *FASEB. J*. 25.12(2011):4498-4510.
Wong et al. "Pushing Back: Wound Mechanotransduction in Repair and Regeneration." *J. Invest. Dermatol*. 131.11(2011):2186-2196.
Wozniak et al. "Mechanotransduction in Development: A Growing Role for Contractility." *Nat. Rev. Mol. Cell Biol*. 10.1(2009):34-43.
Yeung et al. "Effects of Substrate Stiffness on Cell Morphology, Cytoskeletal Structure, and Adhesion." *Cell Motil. Cytoskeleton*. 60.1(2005):24-34.
Yoo et al. "Bio-Inspired, Bioengineered and Biomimetic Drug Delivery Carriers." *Nat. Rev. Drug Discov*. 10.7(2011):521-535.
Yoon. "Hidden Markov Models and their Applications in Biological Sequene Analysis." *Curr. Genomics*. 10.6(2009):402-415.
Young et al. "Gelatin as a Delivery Vehicle for the Controlled Release of Bioactive Molecules." *J. Control. Release*. 109.1-3(2005):256-274.
Zemel et al. "Optimal Matrix Rigidity for Stress Fibre Polarization in Stem Cells." *Nat. Phys*. 6.6(2010):468-473.
Zhang et al. "A Tension-Induced Mechanostransduction Pathway Promotes Epithelial Morphogenesis." *Nature*. 471.7336(2011):99-103.
Zhang et al. "Talin Depletion Reveals Independence of Initial Cell Spreading from Integrin Activation and Traction." *Nat. Cell Biol*. 10.9(2008):1062-1068.
Zhao et al. "Stress-Relaxation Behavior in Gels with Ionic and Covalent Crosslinks." *J. Appl. Phys*. 107.6(2010):63509.

\* cited by examiner

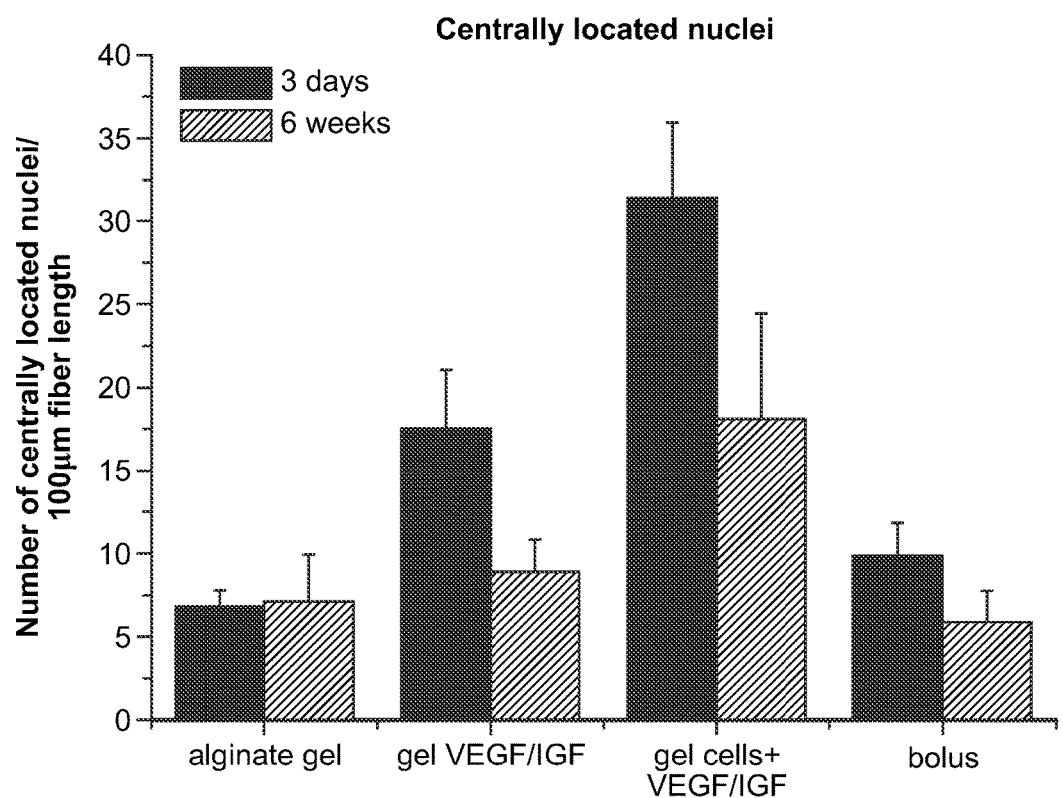
FIG. 4-A

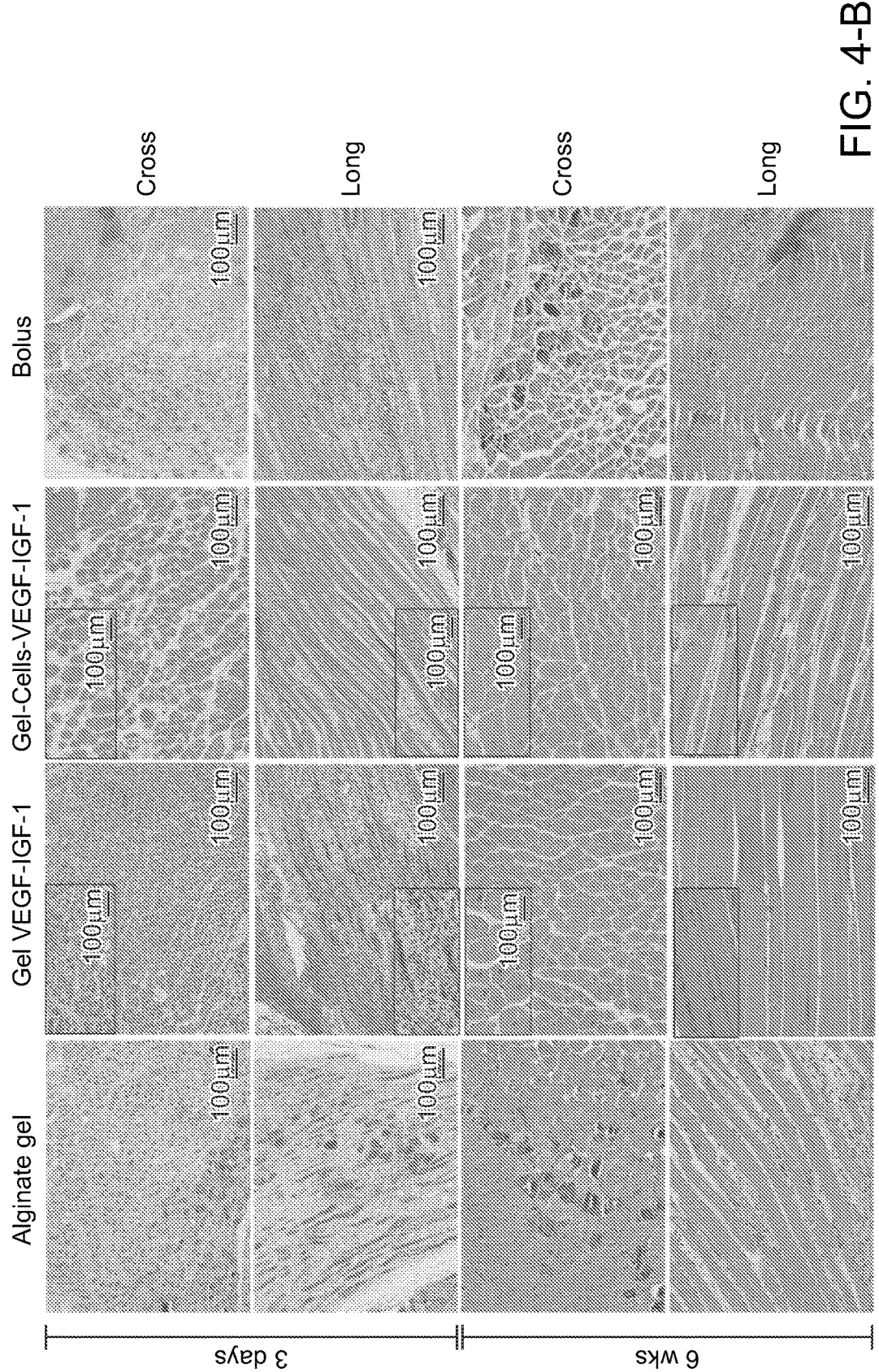
FIG. 4-B

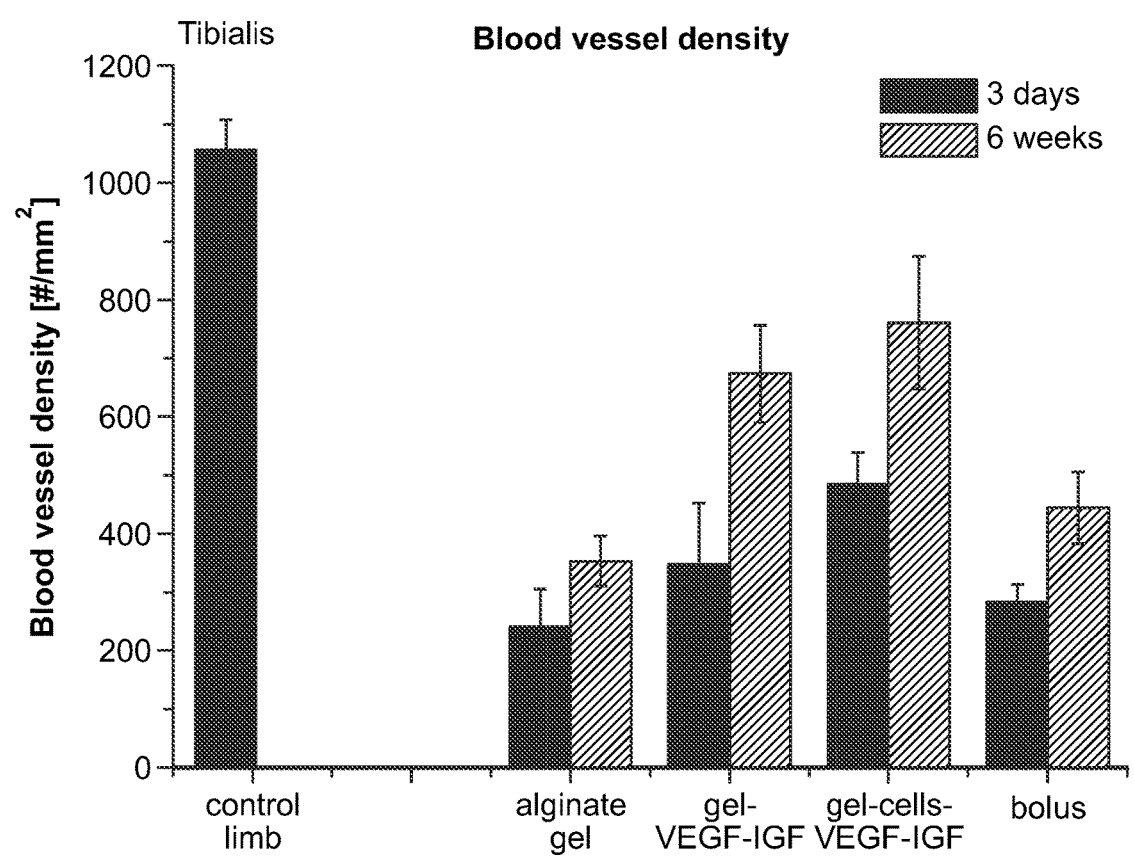
FIG. 5-A

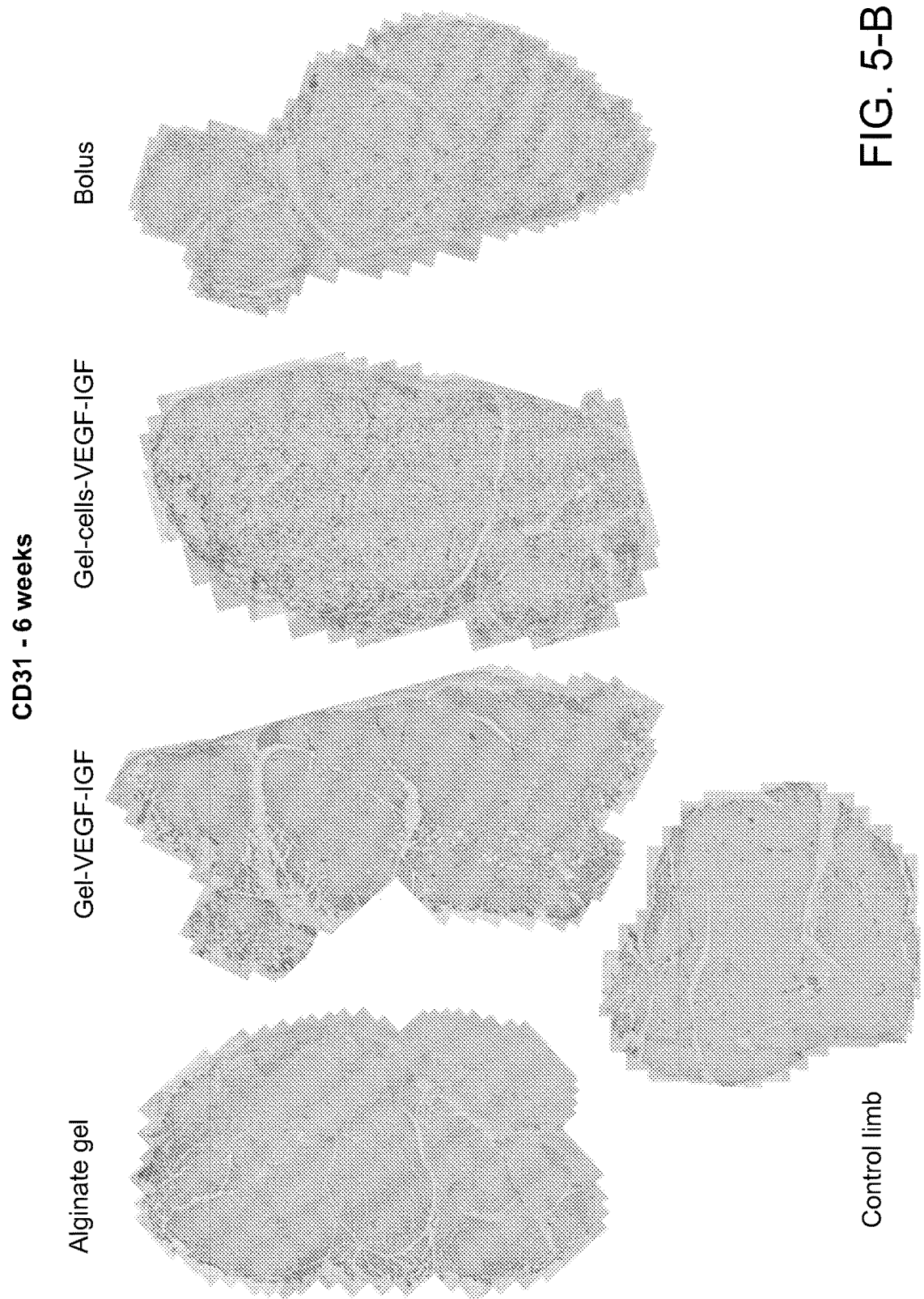
FIG. 5-B

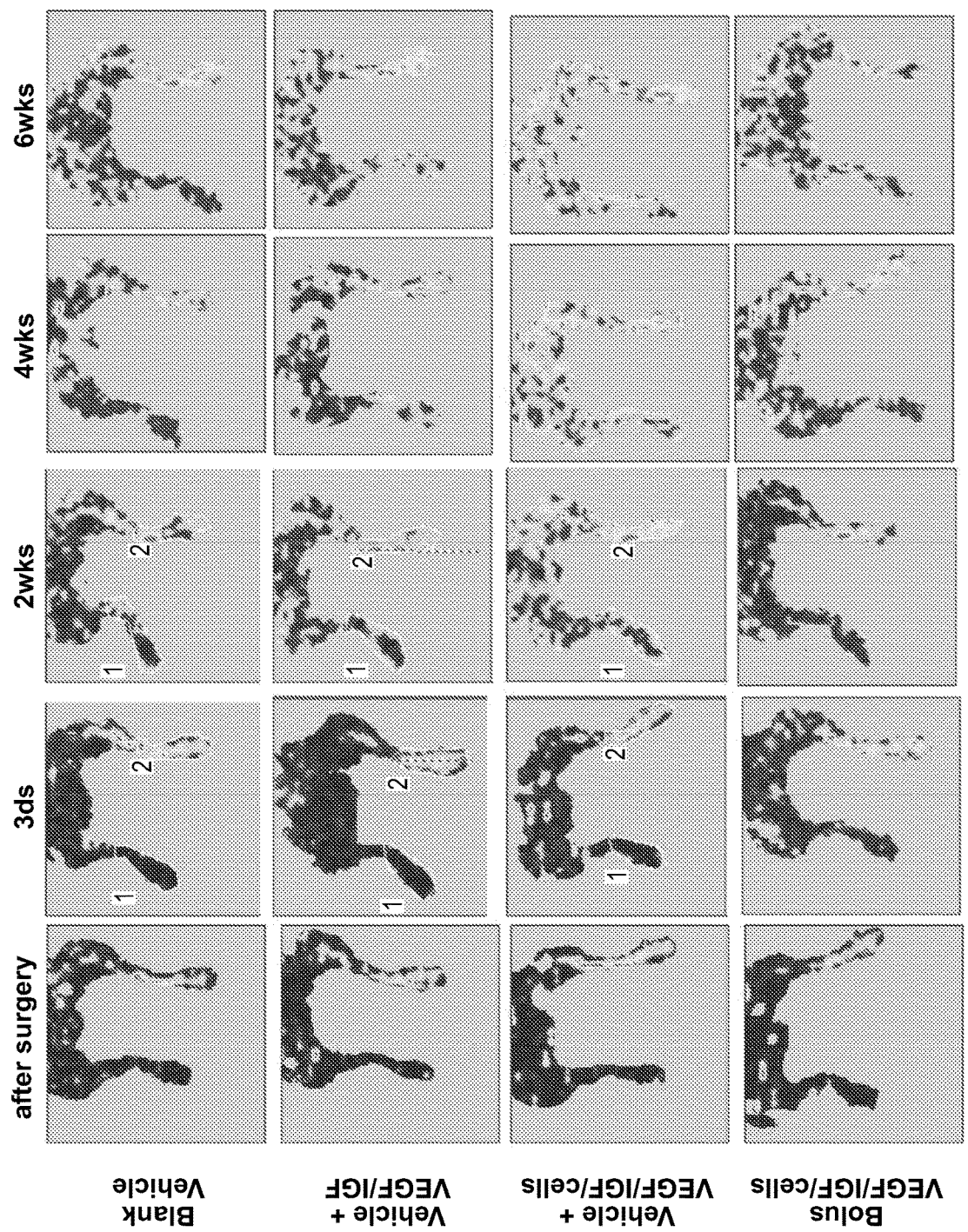
FIG. 6-A

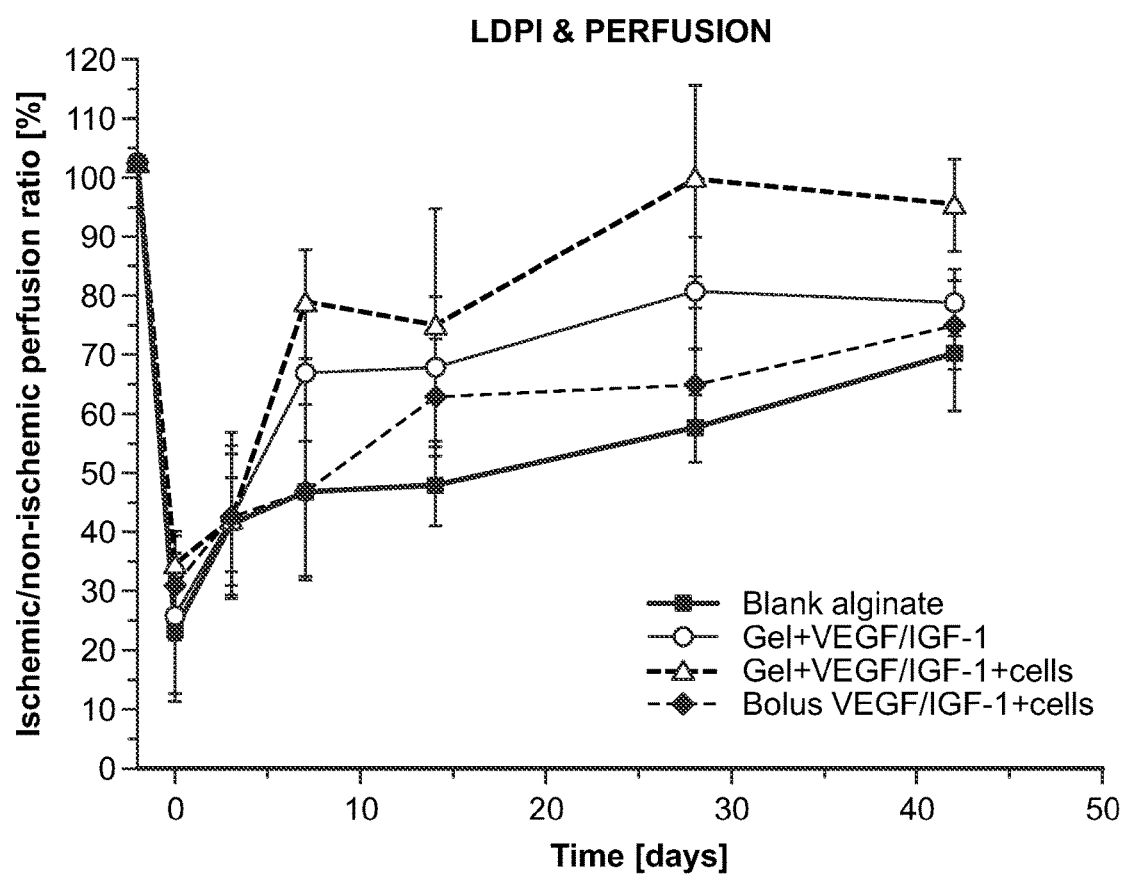
FIG. 6-B

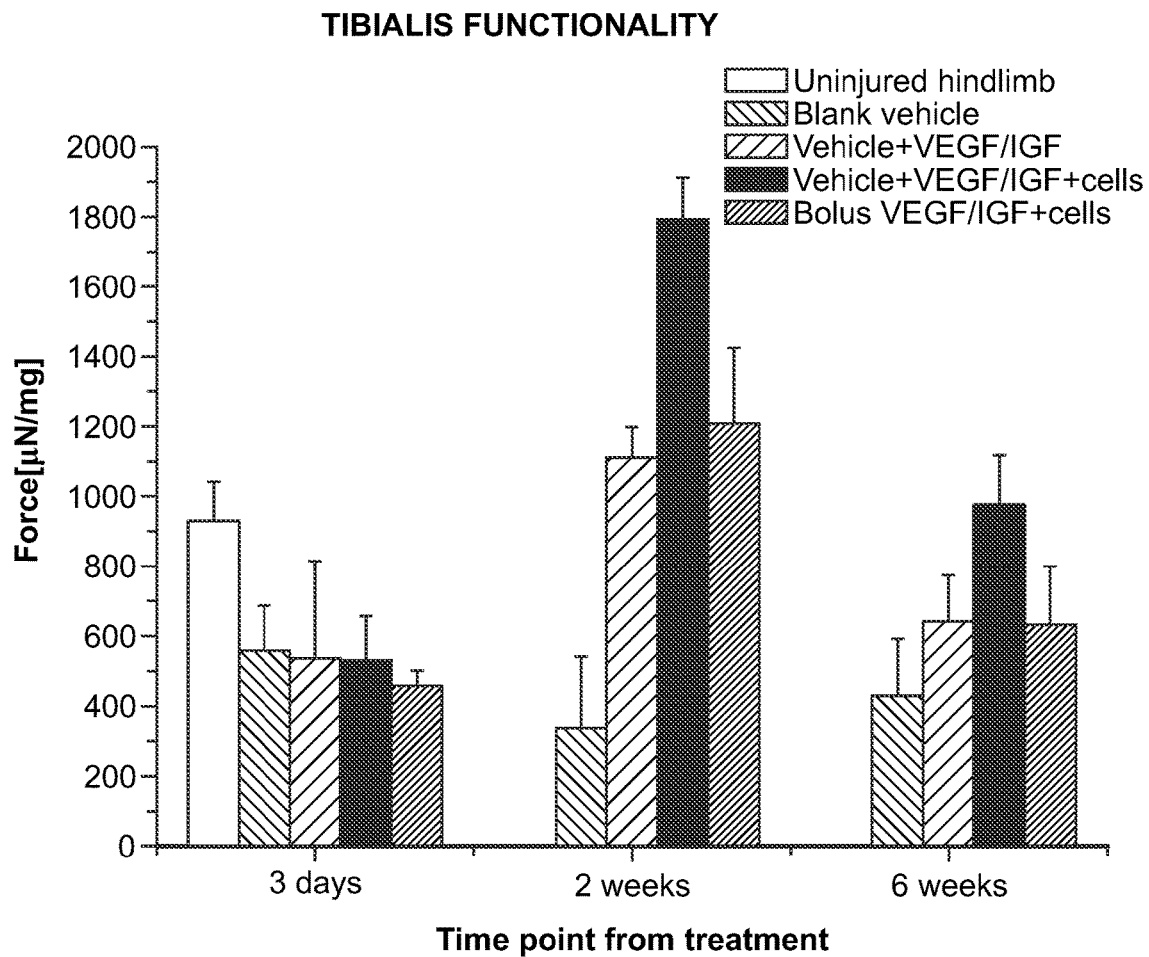
FIG. 7-A

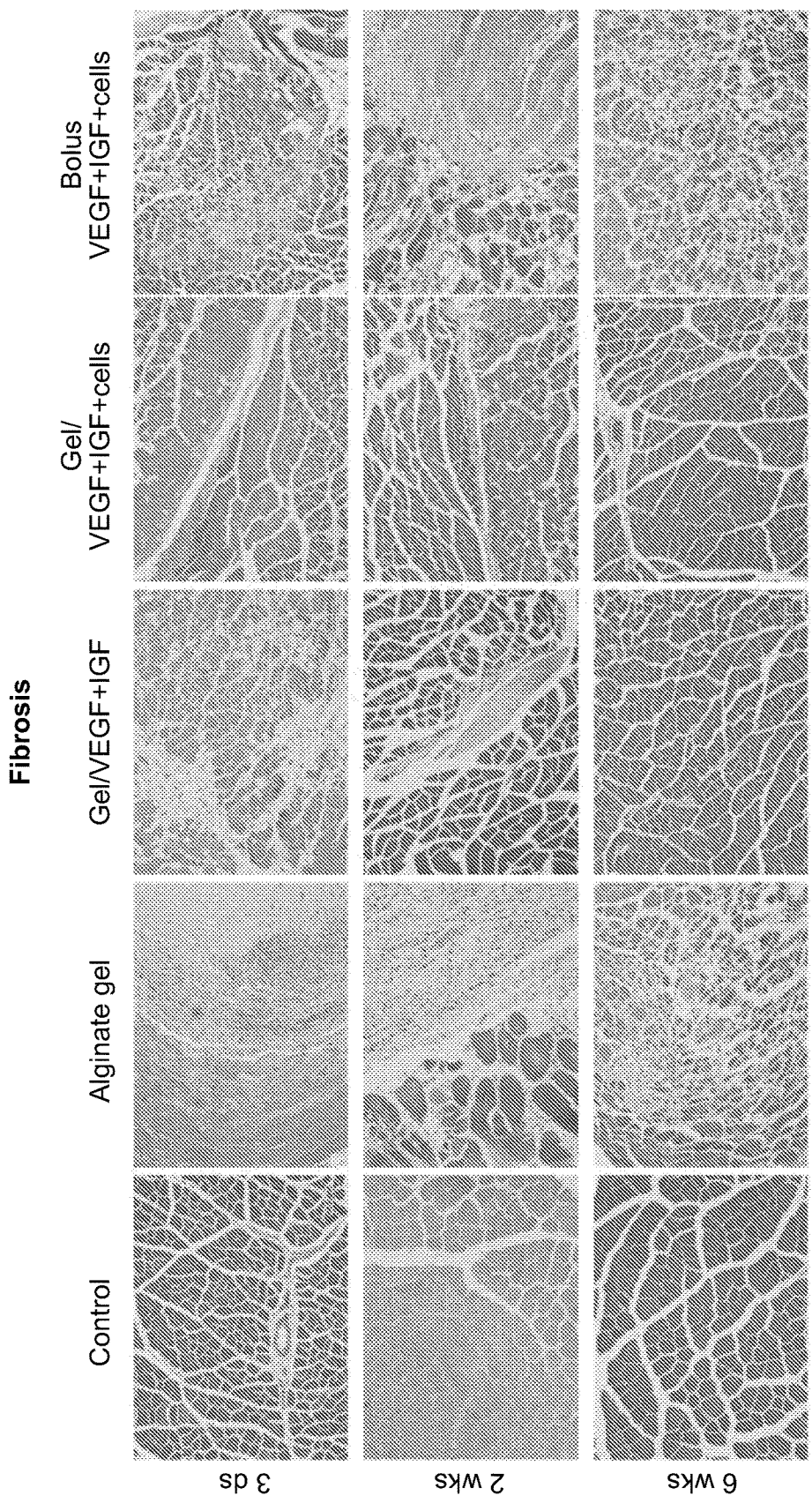
FIG. 7-B 18 h 24 h 4 h     12 h     24 h

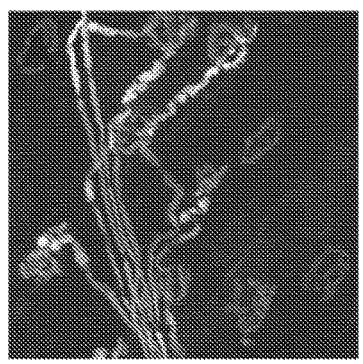 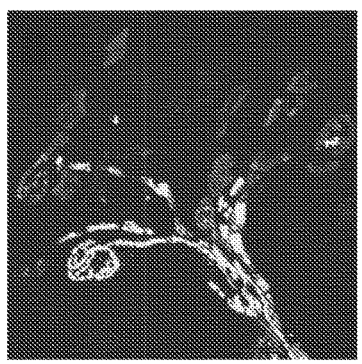 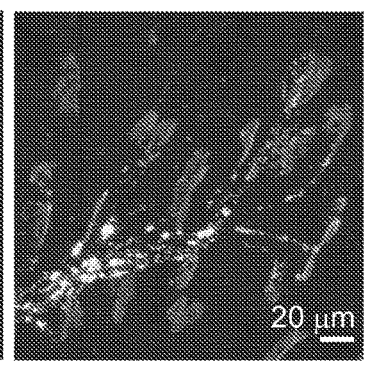
FIG. 13A  FIG. 13B  FIG. 13C
3 μg  0.3 μg  0.03 μg
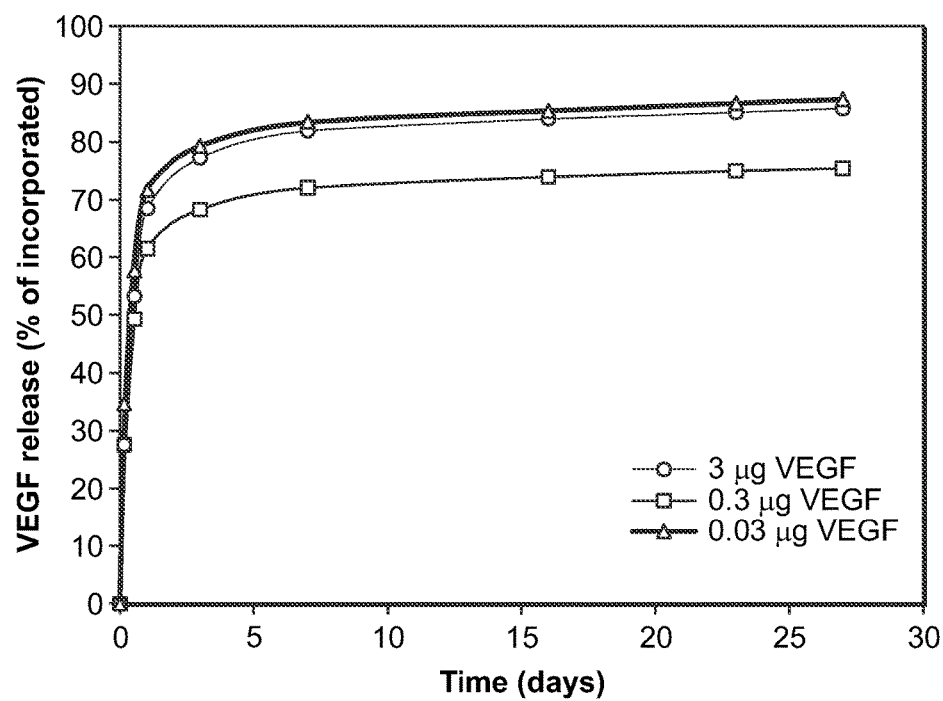
FIG. 13D FIG. 14A    FIG. 14C
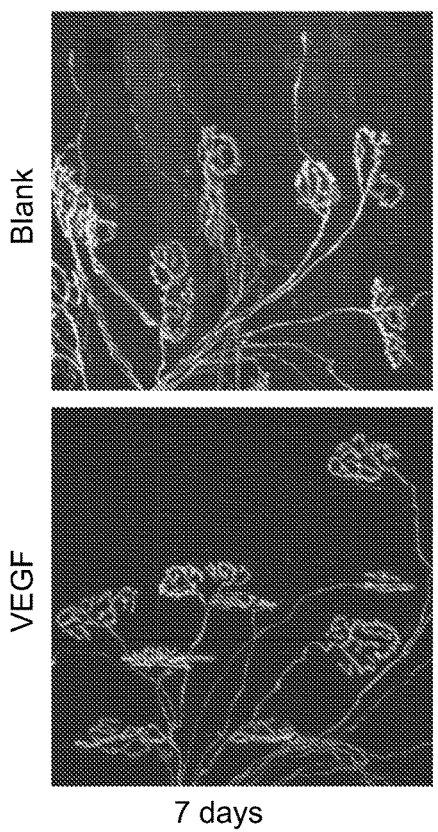
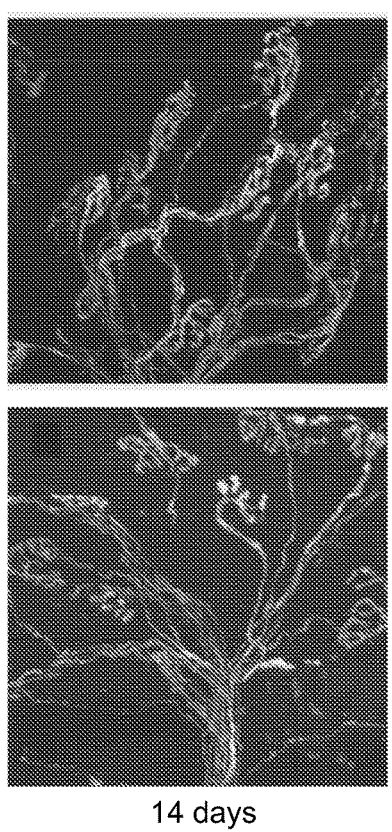
7 days          14 days
FIG. 14B    FIG. 14D
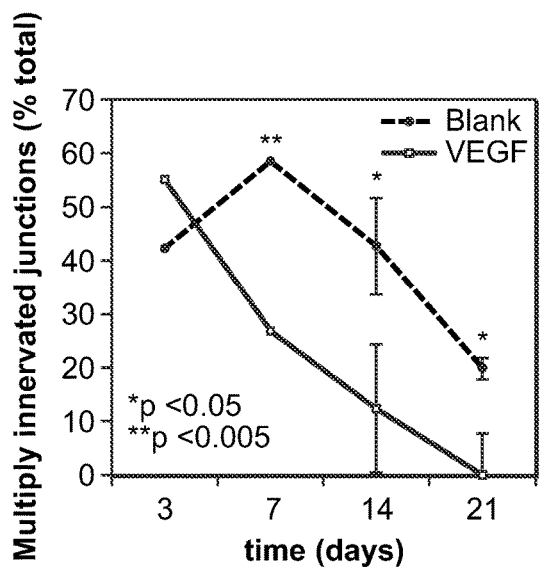
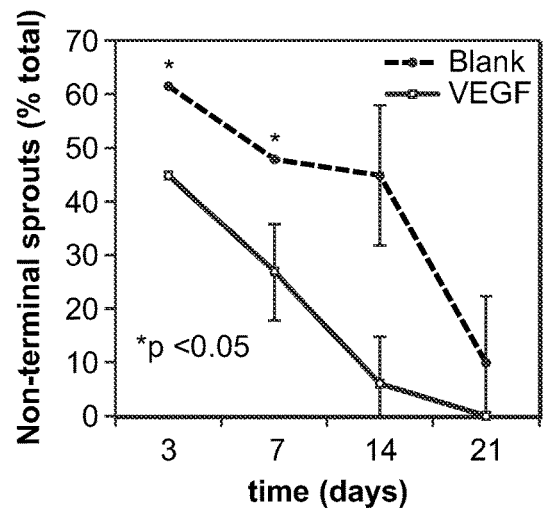
FIG. 14E    FIG. 14F FIG. 18A  Uncompressed scaffold
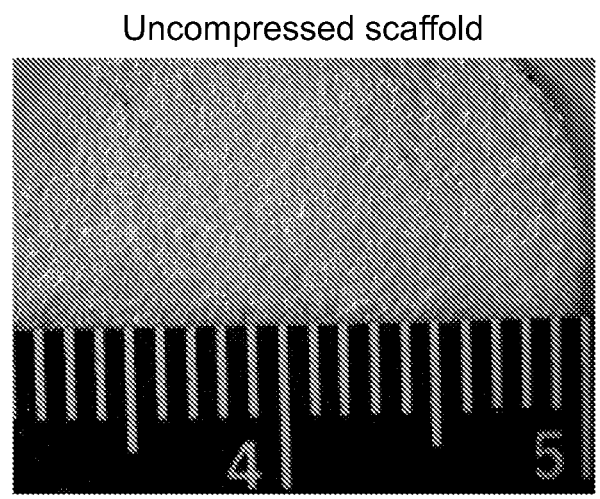
FIG. 18B  Uncompressed scaffold
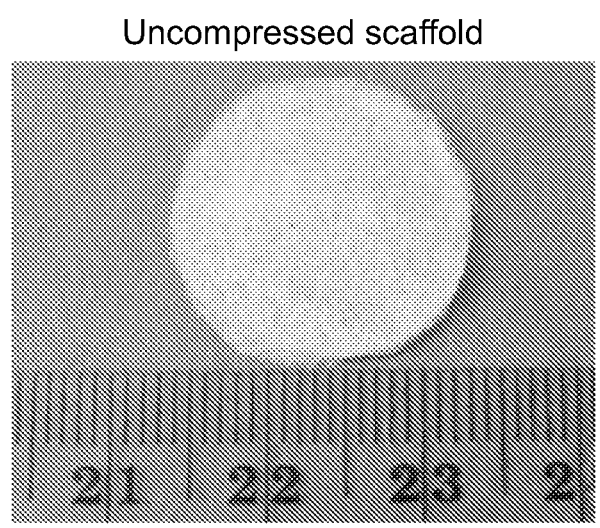
FIG. 18C  Uncompressed scaffold side view
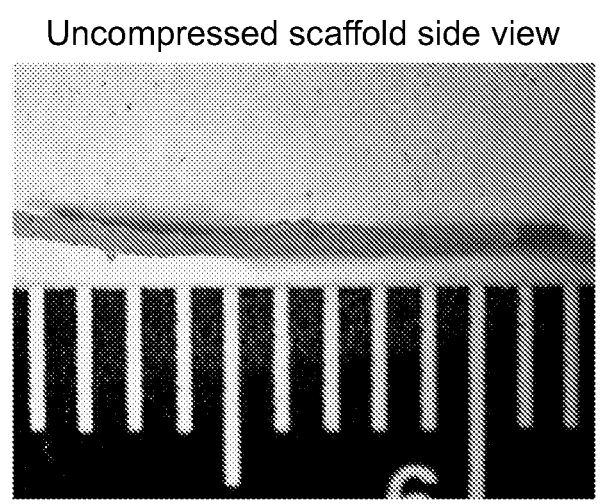

FIG. 18D  Compressed and cut to desired size for implantation to tibialis anterior muscle
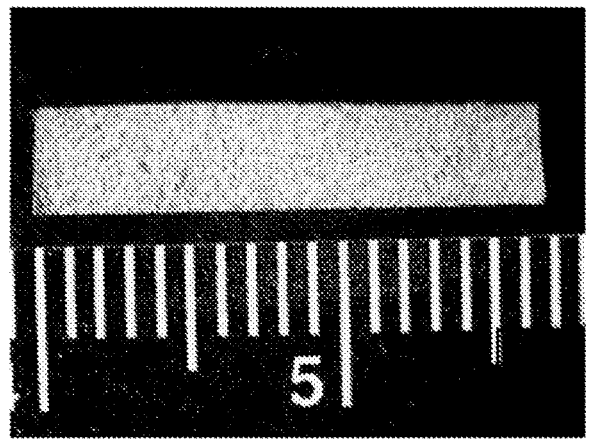
FIG. 18E  Rolled up on a 10 G syringe
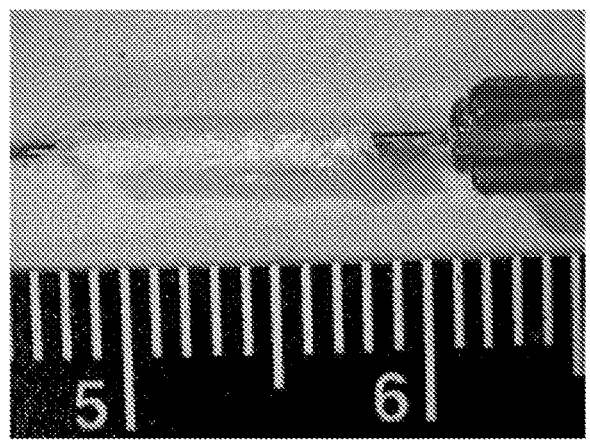
FIG. 18F  Fitted into an 14 G angiocath I.D: 1.8mm
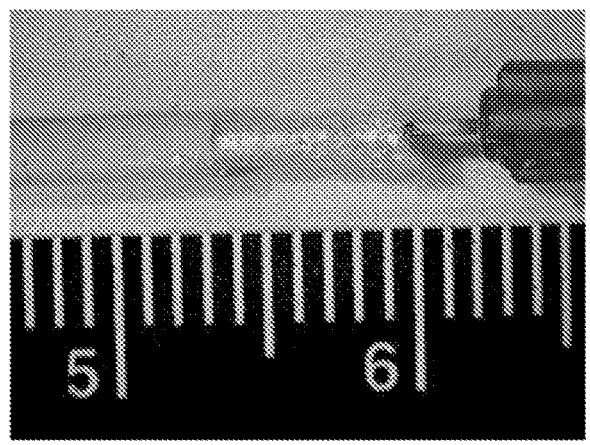

FIG. 18G  Dehydrated Scaffold pushed out of the catheter
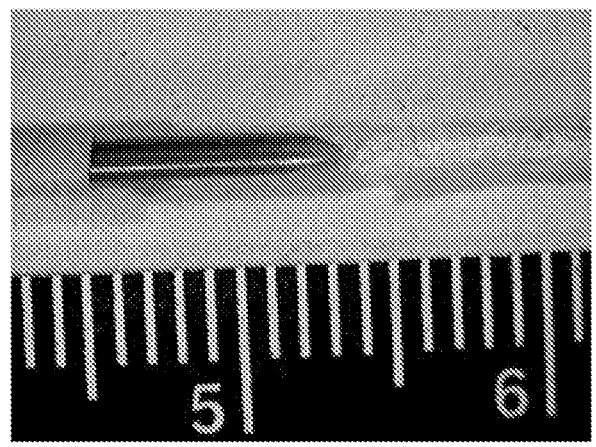
FIG. 18H  Rehydrated scaffold
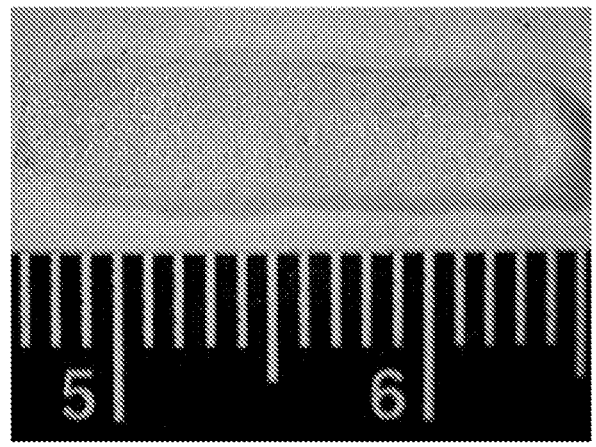

ENHANCEMENT OF SKELETAL MUSCLE STEM CELL ENGRAFTMENT BY DUAL DELIVERY OF VEGF AND IGF-1

RELATED APPLICATIONS

This application is a national stage application, filed under 35 U.S.C. §371, of International Application No. PCT/US2011/027446, filed Mar. 7, 2011, which claims the benefit of U.S. Provisional Application No. 61/339,526, filed Mar. 5, 2010, the contents of which are incorporated by references in their entireties.

STATEMENT AS TO FEDERALLY SPONSORED RESEARCH

This invention was made with government support under DE013349 and AG029705 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 18, 2016, is named 117823_08402_ST25.txt and is 24,576 bytes in size.

BACKGROUND OF THE INVENTION

Musculoskeletal disorders and diseases are the leading cause of disability in the United States and account for more that one-half of all chronic conditions in people over 50 years of age in developed countries.

Among various musculoskeletal injuries, soft tissue skeletal muscle injuries often cause a significant loss of flexibility and strength. Incomplete healing of these injuries could lead to a frequent reinjury of skeletal muscles. This scenario is especially common for athletes and military personnel, for whom the risks of traumatic skeletal muscle injuries are common.

SUMMARY OF THE INVENTION

The invention features an improved device and method for extended repair and regeneration of muscle tissue due to injury such as combat injury, lacerations, traumatic physical accidents (e.g., major surgeries, car accidents, work-related accidents) or disease such as muscular dystrophies, multiple sclerosis, heart disorders, lung disorders, and urinary tract disorders such as incontinence. The device is used as injectable delivery vehicle for the regeneration of muscle tissue and comprises a hydrogel. The hydrogel comprises a vascular endothelial growth factor (VEGF) or a combination of VEGF and Insulin-like growth factor (IGF), e.g. Insulin-like growth factor-1 (IGF-1), for use as injectable delivery vehicle for the regeneration or innervation of muscle tissue. The VEGF+IGF combination leads to a synergistic regeneration effect on muscle tissue.

The hydrogel optionally further comprises a population of myogenic cells, e.g., satellite cells or myoblasts. Such cells are obtained by biopsy from mature muscle tissue of the individual to be treated. The myogenic cells are seeded into or onto the hydrogel ex vivo. Alternatively, the cells are seeded into or onto the hydrogel in vivo following insertion of the hydrogel into the subject. The cells are expanded ex vivo or used directly, i.e., without expansion in culture prior to seeding the hydrogel.

The hydrogel, if to be used to transplant cells, comprises pores to permit the structure to be seeded with cells and to allow the cells to proliferate and migrate out to the structure to relocate to bodily tissues such as the injured or diseased muscle in need of repair or regeneration. For example, cells are seeded at a concentration of about $1\times10^4$ to $1\times10^7$ cells/ml and are administered dropwise onto a dried hydrogel device. The dose of the gel/device to be delivered to the subject is scaled depending on the magnitude of the injury or diseased area, e.g., one milliliter of gel for a relatively small defect and up to 50 mls of gel for a large wound.

The hydrogel composition permits cell movement throughout the structure. Cells move through a structure by virtue porosity (e.g., pores that are at least one micron in size); by virtue of their ability to deform the material, e.g., squeeze through the material or push their way out of the material; or by virtue of the cell's ability to degrade the material. The scaffold preferably comprises pores, e.g., nanopores (0.1-100 micron diameter), micropores (1-50 micron diameter), or macropores (50-500 micron diameter). For example, the hydrogel comprises macropores that are characterized by a diameter of 400-500 microns. The gel delivery devices are suitable for treatment of human beings, as well as animals such as horses, cats, or dogs.

In some embodiments, the hydrogel is characterized by shape-memory. The polymer chains of the hydrogel are covalently crosslinked and/or oxidized. Such hydrogels are suitable for minimally-invasive delivery. Prior to delivery into the human body, such a hydrogel is lyophyllized and compressed prior to administration to a subject for the regeneration of muscle tissue. Minimally-invasive delivery is characterized by making only a small incision into the body. For example, the hydrogel is administered to a muscle of a subject using a needle or angiocatheter. Alternatively, the hydrogel delivery vehicles are administered to the body using conventional surgical techniques.

An exemplary device is characterized by the following components. The device comprises (a) a scaffold comprising an ECM component; (b) a combination of growth factors, said combination comprising VEGF and IGF; and (c) a population of myogenic cells, e.g., such as satellite cells. The growth factors are incorporated into or coated onto said scaffold composition and are released from the scaffold at approximately the same rate or at different rates. For example, VEGF is released from the scaffold composition at a first rate and IGF is released from the scaffold composition at a second rate. The scaffold may comprise nanopores, micropores, or macropores. For example, the scaffold comprises an open, interconnected macroporous structure.

Methods of muscle repair and regeneration comprise introducing into a tissue the device described above. Implantation of the device leads to muscle regeneration and repair over an extended period of time, e.g., 2, 4, 6, 8, 10, 12, 16, weeks or more post implantation. Although the methods and devices are applicable to many different tissue types, a preferred tissue comprises primarily skeletal muscle tissue, cardiac muscle, or smooth muscle tissue.

The devices and methods are particularly useful for treatment of aged subjects, because the naturally-occurring regeneration of muscle tissue decreases dramatically with the age of an individual. Children or teenager comprise a basal level of muscle regeneration after injury or disease, and the devices and methods of the invention enhance that level of regeneration. However, aged subjects (e.g., 20-30 years of age, and more particularly 35, 40, 50, 60, 70, 80, 90 or more years of age) are characterized by minimal or no basal regenerative activity. In such individuals, the hydrogel delivery vehicles comprising VEGF+IGF led to significant muscle regeneration, a surprisingly beneficial effect.

The growth factors used in therapeutic applications are purified. A purified composition such as a protein or peptide is at least 60%, by weight, free from proteins and naturally occurring organic molecules with which it is naturally associated. Preferably, the preparation is at least 75%, more preferably 90%, and most preferably at least 99%, by weight, the desired composition. A purified protein or polypeptide may be obtained, for example, by affinity chromatography. A purified nucleic acid, polypeptide, or other molecule is one that has been separated from the components that naturally accompany it. Typically, the polypeptide is substantially pure when it is at least 60%, 70%, 80%, 90%, 95%, or even 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis.

Publications, U.S. patents and applications, GENBANK™/NCBI accession numbers, and all other references cited herein, are hereby incorporated by reference.

BRIEF DESCRIPTION OF THE DRAWINGS

(FIG. 3A) The weight of the uninjured tibialis muscles (Control) at 3 days, 2 weeks and 6 weeks is compared with the muscles after myotoxin/ischemia injury and treatment with blank alginate gel (Alginate Gel), alginate gel delivering VEGF and IGF-1 (gel/VEGF+IGF), alginate gel delivering cells and VEGF and IGF-1 (Gel/VEGF/IGF-1+cells) and, bolus delivery of cells and VEGF and IGF-1 in PBS (Bolus). Values represent mean±SD (n=6) in all graphs. p<0.05 level the means are significantly different (FIG. 3B) Photographs of explanted tibialis anterior at 3 days following treatment with blank alginate gel and alginate gel delivering cells and VEGF and IGF-1 (Gel/VEGF/IGF-1+cells). Size bars are shown on the photomicrographs.

FIGS. 4A-B are a bar graph and a series of photomicrographs showing analysis of muscle regeneration. (FIG. 4A) The number of centrally located nuclei of regenerating fibers at 3 days and 6 weeks after the induction of myotoxin/ischemia injury was quantified. (FIG. 4B) Representative photomicrographs of tibialis tissue sections from injured hindlimbs of C57 mice at postoperative 3 days and 6 weeks, stained with H&E. Cross and longitudinal section respectively of injured muscles treated with blank alginate gel (Alginate Gel), alginate gel delivering VEGF and IGF-1 (gel/VEGF+IGF), alginate gel delivering cells and VEGF and IGF-1 (Gel/VEGF/IGF-1+cells) and, bolus delivery of cells and VEGF and IGF-1 in PBS (Bolus). High power magnification are shown on the side. ANOVA statistical tests were performed on all data sets. At p<0.05 level the means are significantly different.

FIGS. 5A-B are a bar graph and a series of photomicrographs showing quantification of blood vessel densities. (FIG. 5A) Quantification of blood vessel densities in tibialis muscles at 3 days and 6 weeks after induction of myotoxin/ischemia injury and treatment with blank alginate gel (alginate gel), alginate gel delivering VEGF and IGF-1 (gel/VEGF+IGF), alginate gel delivering cells and VEGF and IGF-1 (Gel/VEGF/IGF-1+cells), bolus delivery of cells and VEGF and IGF-1 in PBS (Bolus) and, control (non-operated) limb. Values are mean±SD. p<0.05. (FIG. 5B) Photomicrographs of the entire tibialis section were obtained postoperative 6 wks, and immunostained for the endothelial marker CD-31.

FIGS. 6A-B are a series of laser Doppler images and a line graph showing blood perfusion. (FIG. 6A) Representative color-coded laser Doppler perfusion imaging (LDPI) images at various time points (after surgery, at 3 days, 2, 4 and 6 weeks post-operation) of mice for all the conditions analyzed. (FIG. 6B) LDPI blood perfusion analysis of C57 mice hindlimbs treated with (black square) blank alginate gel, (gray circle) alginate gel delivering VEGF and IGF-1, (gray triangle) alginate gel delivering cells and VEGF and IGF-1 and, (black diamond) bolus delivery of VEGF and IGF-1 in PBS. p<0.05; mean values are presented with SD.

FIGS. 7A-B are a bar graph and a series of photomicrographs showing functional properties of skeletal muscles and interstitial fibrotic collagen deposition (slow & fast myofibers). (FIG. 7A) Tetanic force of the anterior tibialis muscles of mice were measured at 3 days. 2 and 6 weeks after treatment. Tetanic force was normalized to each muscle's weight to obtain weight-corrected specific force. Stimulation was evoked via parallel wire electrodes with 2.0 ms pulse width and 1 sec train duration, and the maximal stimulation was measured at 15V-300 Hz. Mean values are presented with SD; p<0.05 (FIG. 7B) Representative photomicrographs show the deposition of interstitial fibrotic collagen of tissue sections stained with Masson's trichromic in tibialis muscles from uninjured hindlimbs (control) and hindlimbs of mice at postoperative 3 days, 2 weeks and 6 weeks treated with blank alginate gel (Alginate Gel), alginate gel delivering VEGF and IGF-1 (gel/VEGF+IGF), alginate gel delivering cells and VEGF and IGF-1 (Gel/VEGF/IGF-1+cells) and, bolus delivery of cells and VEGF and IGF-1 in PBS (Bolus). Images are representative of 5 independent experiments.

FIGS. 13A-C are photomicrographs and FIG. 13D is a line graph showing that neural regeneration by exogenous VEGF is time and dose-dependent.

FIGS. 14A-D are photomicrographs and FIGS. 14 E-F are line graphs showing that local delivery of VEGF promotes the maturation of motor axons in motor endplates and neuromuscular junction remodeling after the ischemic injury and neural crush.

FIGS. 18A-H is a series of photographs showing dehydrated scaffold/delivery vehicle for minimally invasive delivery. The lyophilized scaffold is compressed from a thickness of around 1 mm (FIGS. 18A and 18B) to a thickness of 0.1 mm (FIG. 18C), cut to desired size (13.5× 2.6 mm2) (FIG. 18D), rolled up into a tight cylinder around a 10 G needle (FIGS. 18E and 18F), and delivered through 1.8 mm (FIGS. 18I and 18D) angiocath (FIGS. 18F and 18G) to achieve minimally invasive delivery through a 2-3 mm incision in the skin. The scaffold has been rehydrated with DPBS from the 10 G needle (FIG. 18H), which is also used to deliver a 50 µL suspension of cells and growth factors to rehydrate the scaffold immediately after insertion next to the injured muscle. The scaffold absorbs the DPBS solution and rapidly (<30 seconds) and recovers its original 3D dimensions (FIG. 18G).

DETAILED DESCRIPTION

Figure 1:
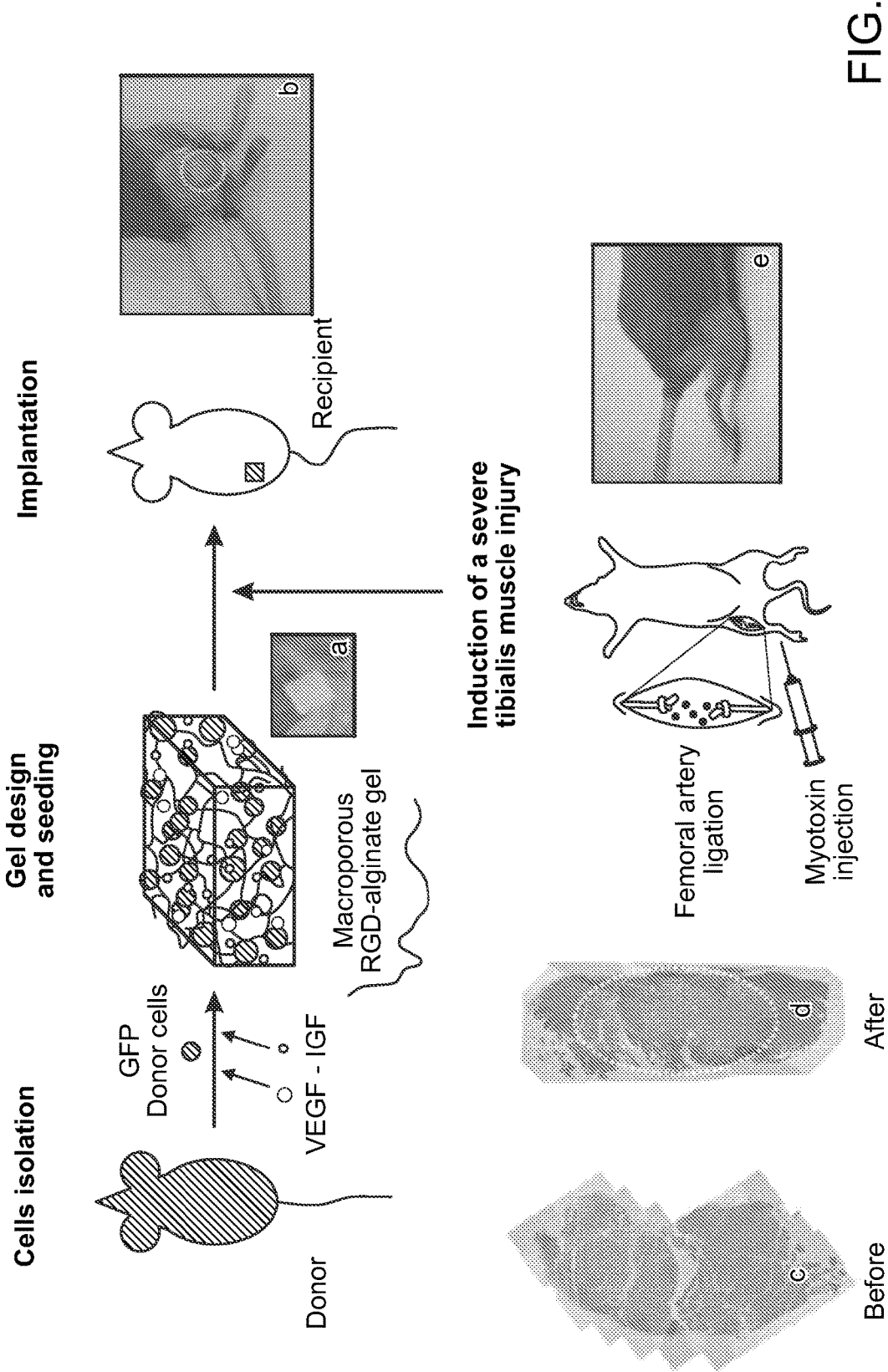
FIG. 1 is a diagram of the study protocol. Primary GFP myoblasts (green), isolated from transgenic Tg(ACTbE-GFP)1Osb, constitutively expressing GFP in all the cells, were seeded in a macroporous RGD-modified alginate gel (blue) encapsulating VEGF (red) and IGF-1 (yellow). Wild type C57BL/6J mice were injured with a myotoxin injection first and an ischemia damage was further induced after 6 days by a femoral artery and vein ligation before the treatment. (a). Photograph of the macroporous square-shaped alginate scaffold (5×5×2 mm) in a lyophilized form. (b). Scaffold implant after 2 weeks from treatment. (c-d). Tibialis cross-sections, H&E stained before (c) and after (d) muscle injury. (e). Complete loss of locomotion of the injured hindlimb after injuries.

The two main strategies today in cell therapy consist of the direct injection of cells into the damaged tissue or their pre-culture and transplantation on scaffolds that serve as a template for neo-tissue formation. However, modulation of tissue regeneration subsequent to injury by cell transplantation requires the survival of donor cells and their stable incorporation into the host tissue. Previous approaches have been limited by low survival and integration rate of injected cells into host tissue. The work described herein involves the transplantation of progenitor cells on cell-instructive scaffolds designed to maintain cell viability, promote cell activation (proliferation) and outward migration from the scaffold in order to promote repopulation of the host damaged tissue and regeneration of the myotoxin-injured skeletal muscle ischemia. The goal was to direct the myogenic cells to bypass their normal tendency to differentiate and remain in a proliferative phase until a sufficient number of cells is attained to regenerate the tissue.

Bolus delivery of VEGF and/or IGF is ineffective for tissue regeneration. However, dual delivery of VEGF with IGF-1 from macro-porous peptide-modified alginate scaffolds enhanced the engraftment of transplanted myogenic stem cells participating in subsequent rounds of injury repair, increased the proliferation of the satellite cells, limited fibrosis and, accelerated the regenerative process of injured skeletal muscle, resulting in increased muscle mass and most importantly, improved contractile function. Together, these results demonstrate the efficacy of finely controlled differentiated state of myogenic stem cell transplant for treating muscle degenerative disease or injury to muscle tissue.

Exemplary hydrogel delivery vehicles for muscle regeneration require the following components: (1) a composition to mediate adhesion of cells' (2) a composition to induce migration of cells into surrounding tissues; and (3) a composition to induce an angiogenic response. ECM molecules such as RGD peptides are useful to mediate cell adhesion and then migration. For muscle cells, e.g., myogenic cells such as satellite cells or myoblasts, IGF is useful to induce migration out of the scaffold delivery device and into surrounding muscular tissue. HGF and FGF2 is also useful for this purpose. The studies described herein indicate that IGF is as good as or even better than the combination of HGF and FGF2. Finally, VEGF is useful to induce the host angiogenic response. The presence of VEGF in the hydrogel leads to enhanced regeneration compared to the level in its absence.

Skeletal Muscle and Skeletal Muscle Injury

Skeletal muscle accounts for half of the total body mass and is the most abundant tissue of the human body. The major function of skeletal muscle is to coordinate body movements through attachment to the skeleton. To maintain its physiological function, the muscle tissue needs to be vascularized and innervated. A skeletal muscle is composed of many bundles of myofibers. A single myofiber is derived from the fusion of numerous myoblasts. Each myofiber contains many myofibrils, which are composed of repeating sarcomeres. Adult skeletal muscle has a large population of quiescent muscle stem cells termed satellite cells (2-3% of the nuclei in the tissue) that reside just outside the muscle fiber's plasma membrane.

When injured or otherwise compromised by disease (e.g., a degenerative disease), a skeletal muscle has limited ability to restore morphology and function. The major obstacle for skeletal muscle regeneration is fibrosis and formation of scar tissue during the muscle healing process, which leads to incomplete functional recovery, loss of flexibility, and muscle strength. The compositions and methods described herein speed up the repair process of muscle healing and reduce the formation of scar tissue.

Direct injection of muscle stem cells has been unsuccessful due to the rapid loss in viability of the majority of the cells. Prior to the invention, numerous reports have indicated that cultured myoblasts demonstrate poor engraftment efficiency when subsequently transplanted, with little functional impact. In contrast, the studies described herein demonstrate that delivery of cultured myoblasts on an appropriate delivery vehicle leads to a high level of engraftment, and profound functional impact.

Biodegradable scaffolds loaded with therapeutic molecules (VEGF and/or IGF), and in some cases loaded with myoblast cells, led to an enhancement in tissue regeneration. Among various musculoskeletal injuries, soft tissue skeletal muscle injuries often cause a significant loss of flexibility and strength. Incomplete healing of these injuries could lead to a frequent reinjury of skeletal muscles.

Satellite Cells

Muscle degeneration is rapidly followed by the activation of an auto-repairing process. This phase is characterized first by the activation of adult muscle satellite cells and the subsequent events: proliferation, differentiation, and fusion of these cells, leading to new myofiber formation and restoration of the functions of a contractile apparatus. With minor damage, skeletal muscles can often repair themselves by regenerating muscle fibers and restoring muscle strength. As soon as a muscle injury occurs, myogenic precursor cells are able to initiate rapid and efficient growth and regeneration. The predominant source of the myogenic precursor cells is satellite cells. Satellite cells are small mononuclear progenitor cells that reside between the basement membrane and sarcolemma of individual skeletal muscle fibers. They are involved in the normal growth of muscle, as well as regeneration following injury or disease. Their primary function is to mediate postnatal muscle growth and repair. They can be triggered to proliferate and differentiate into myogenic cells, fusing to augment existing muscle fibers and to form new fibers.

In undamaged muscle, the majority of satellite cells remain quiescent; however, in response to mechanical strain or injury, satellite cells become activated. When muscle cells undergo injury, quiescent satellite cells respond to the injury and are released from their niche. Satellite cells can be activated to give rise to skeletal myoblasts. The myoblasts in turn differentiate and form post-mitotic myotubes. These myotubes can facilitate muscle regeneration and repair by fusing into existing neighboring myofibers. Satellite cells are harvested from an individual to be treated and loaded into growth factor-containing hydrogels. Optionally, the harvested satellite cells are cultured ex vivo prior to being loaded onto the hydrogel (e.g., dehydrated doped hydrogel described below) and administered to the patient.

Satellite cells express a number of distinctive molecular markers that are used to identify and purify the cells (e.g., using flow cytometry and Fluorescence Activated Cell Sorting (FACS) analysis). For therapeutic application, the satellite cells need not be isolated from surrounding muscle tissue but transplanted on intact muscle fibers or merely gently dissociated prior to applying the cells to the scaffold/delivery vehicle. In some cases, freshly harvested cells (e.g., satellite cells on muscle fibers, rather than isolated, cultured cells) are preferable due to their greater capacity to generate tissue. In this case, fewer cells are required than when cultured cells are used. Human satellite cells are obtained by biopsy from a mature muscle, e.g., quadriceps, gluteus maximus, bicep, tricep, or any muscle of the individual to be treated. The cells are multiplied ex vivo or used without expanding the cells in culture. For example, the cell suspension to be used to seed the gel comprises muscle fibers and satellite cells. Alternatively, the suspension is a population of purified satellite cells. Prior to the invention, cultured myoblasts were not effective for muscle regeneration; however, cultured myoblasts delivered in the hydrogels of the invention proliferate and are induced to migrate due to the structure of the device and the presence of growth factors in the device leading to clinically beneficial muscle regeneration.

Activated quiescent satellite cells express myogenic transcription factors such as MyoD and/or Myf5. Pax-7 is expressed in both quiescent/or activated satellite cells. Proliferating satellite cells express muscle-specific filament proteins such as desmin as they differentiate to myoblasts. During the muscle repair process, proliferating myoblasts withdraw from the cell cycle to become terminally differentiated myocytes that express Myogenin and MRF4, and subsequently muscle-specific genes such as myosin heavy chain (MHC) and muscle creatine kinase (MCK) [20]. Finally, myocyte fusion gives rise to multinucleated myofibers, which then fuse to each other to form postmitotic muscle fibers or mature skeletal muscle tissue.

Tissue Remodeling and Fibrosis

After naturally-occurring satellite cell initiated regeneration occurs, tissue remodeling starts. Phagocytosis of the damaged tissue and formation of a connective-tissue scar (fibrosis) occurs. Fibrosis is a pathological process that impairs post-injury regeneration of muscle tissue. It starts roughly 2 weeks after injury and can last for up to 2 weeks. Fibrotic tissue inhibits the regenerative growth and reinnervation of muscle tissue, which in turn results in incomplete functional recovery, physical impairment of neighboring normal tissue structure, loss of strength and flexibility, and propensity of reinjury and even atrophy. The compositions and methods described herein speed up the process of muscle healing and reduce the formation of scar tissue following muscle damage.

Growth Factors

Muscle regeneration is regulated by multiple biochemical pathways in which inflammatory cytokines, and growth factors (Table 1) play important roles. The identification of factors that improve the process of muscle healing and reduce the formation of scar tissue is of great importance for restoring the function and structure of the injured muscle.

TABLE 1

Growth factors involved in muscle repair

| Growth Factor | Cell Proliferation | Cell Differentiation |
|---|---|---|
| Hepatocyte growth factor (HGF) | Stimulates | Stimulates |
| Basic fibroblast growth factor (bFGF) | Stimulates | Stimulates |
| Insulin-like growth factor-1 (IGF-1) | Stimulates | Stimulates |
| Nerve growth factor (NGF) | Stimulates | Stimulates |
| Leukemia Inhibitory factor (LIF) | Stimulates | Stimulates |
| Acid fibroblast growth factor (aFGF) | Inhibits | Stimulates |
| Platelet-derived growth factor (PDGF-AA) | Inhibits | Stimulates |
| Platelet-derived growth factor (PDGF-BB) | Stimulates | Inhibits |
| Epidermal growth factor (EGF) | Inhibits | Inhibits |
| Transforming growth factor-α (TGF-α) | Inhibits | Inhibits |
| Transforming growth factor-β1 (TGF-β1) | Inhibits | Inhibits |

IGF compared to a combination of HGF and FGF2 for muscle regeneration

Both HGF and members of the FGF family have been widely used for inducing activation, proliferation and migration of the myoblast cells. Besides those factors, numerous other factors are involved as initiators of satellite cell activation showing both mitogenic and motogenic effects on satellite cells. The role of growth factors in skeletal muscle regeneration were compared in order to identify the best candidate to initiate satellite cell activation, stimulating cells to enter the cell cycle, and inducing their migration out of scaffolds. In particular, HGF, bFGF, IGF-1 (at concentrations ranging between 5, 100, 250 ng/gel for HGF; 5, 100, 250 ng/gel for bFGF and 2.5, 5, 12.5 ng/gel IGF-1) alone or in combination were added to a solution of $G_4$RGDSP-modified alginate scaffolds, prior to gelation via calcium sulfate. The gels were cooled to produce macro-porous scaffolds with open interconnected pores, freeze dried and cell seeded (2×106 cell/mL; 50 μl of cell suspension/gel). The size and morphology of the pores in alginate scaffolds were imaged utilizing a scanning electron microscope. The SEM characterization showed 98% porosity with high pore connectivity of ovoidal-shaped pores with a diameter ranging between 0.009 to 0.130 mm. Scaffold fabrication/characterization and cell seeding is described below and in patent application U.S. Ser. No. 12/992,617, hereby incorporated by reference.

The release kinetics of the growth factors incorporated into the modified binary alginate scaffolds was then quantified. After the gels had completely polymerized, they were cut into 5 mm squares and placed in 24 well plates, and 1 mL of PBS was added to each well. At various time points, the PBS was removed and fresh PBS was added to the scaffolds. The PBS samples were measured for total factor content via quantitative ELISA and the results were compared to the initially incorporated growth factor. The quantification showed that IGF-1, likely due to its smaller size (7.5 Kda) and its non-heparin binding nature, showed a faster release; in fact, approximately 80% of the total IGF loaded was released in the first 24 h, then a sustained release of 0.05% was observed in the following weeks. Conversely, a sustained release was observed for the two heparin binding proteins bFGF and HGF, as previously described (Hill et al., Tissue Eng. 2006).

Primary myoblasts derived from 4-12 weeks-old C57BL/6 mice skeletal musculature were seeded into the scaffolds after being expanded in culture for 7 days and characterized for the expression of the myogenic protein, desmin. Analysis via light microscopy fields revealed that the cell cultures purified via Percoll density gradient fractionation consisted of a 95% desmin-positive population. The resulting cell viability and migration of myoblasts from alginate scaffolds incorporating the GFs alone or in combination was subsequently measured by maintaining scaffolds in culture for various time points. The cell viability inside the scaffold was high in all the conditions analyzed. In particular, the viability of primary myoblasts inside the scaffold was high (80-90%) with IGF-1, and this was a significant improvement compared to the control (blank alginate scaffold without any factors) and IGF at the concentration of 12.5 ng/gel. Conversely, a less pronounced increase (60-70%) of cell viability was found with the following combination of factors IGF100 ng/gel/FGF100 ng/gel; IGF100 ng/gel/HGF100 ng/gel; IGF100 ng/gel/FGF100 ng/gel/HGF100 ng/gel.

Furthermore, IGF-1 was shown to be more effective in inducing a sustained outward migration of the myoblasts when compared with the combination of all factors, both in a wound healing assay and when examining outward migration from macro-porous scaffolds. The results showed that IGF-1 release at all the concentration analysed (IGF 2.5, 5, 12.5 ng/gel) induced the activation of satellite cells promoting a sustained significant outward migration for an extended period of time (2 weeks). In particular, IGF (5 ng/gel) induced respectively a 1.6, 1.5, 1.9, 1.9, 2.9, 4-fold increase respectively at 24 h, 48 h, 72 h, 96 h, 1 week and 2 weeks compared to the control. Moreover, the IGF-1 release alone at the lowest concentrations (2.5 and 5 ng/gel) induced the activation of satellite cells promoting outward migration comparable with the combination of factors IGF100 ng/gel/HGF100 ng/gel and multiple release of IGF100 ng/gel/bFGF100 ng/gel/HGF100 ng/gel. Interestingly the combination of IGF/FGF induced a particular significant outward migration at 48 h followed by a little increase over time; conversely IGF 2.5 and IGF 5 ng/gel induced a sustained significant increase of outward migration over time.

To determine the speed of primary myoblast migration, cells were cultured in two-dimensional plates until near confluency. A scratch, simulating a wound, was generated along the middle line of the plate and the repair of the wound was recorded. The results showed that 7.5 h after the injury IGF-1 at 2.5 ng/gel induces a rapid wound healing when compared with all the other conditions (IGF 2.5, 5, 12.5 ng/gel; HGF 100 ng/gel; FGF 100 ng/gel; and the combinations HGF100 ng/gel/IGF100 ng/gel; FGF100 ng/gel/IGF100 ng/gel; FGF100 ng/gel/HGF100 ng/gel/IGF100 ng/gel).

The combination of factors was not as effective as the induction of IGF alone at the concentrations of 2.5 and 5 ng/gel. All these results together lead to the surprising conclusion that IGF alone is a better candidate to enhance both cell viability inside the scaffold and outward migration compared with all the other factors alone or in combination. Along with these findings, the data showed that macroporous alginate gels delivering IGF in combination with VEGF was shown to increase the speed of outward migration and the persistence time of migrating cells, and led to an improved design of a macroporous vehicle for primary myoblast delivery with potential utility for (ischemic) skeletal muscle tissue engineering able to maintain cell viability and promote a prolonged and sustained migration outward the vehicle.

Alginate modification and scaffold fabrication was carried out as follows. A solution of non-irradiated high-molecular-weight (2%, wt/vol) RGD-modified alginate was prepared in DMEM. HGF, bFGF, IGF-1 and VEGF165 were added to the alginate solution alone or in combination (at concentrations ranging between 5, 100, 250 ng/gel for HGF; 5, 100, 250 ng/gel for bFGF and 2.5, 5, 12.5 ng/gel IGF-1). A calcium sulfate slurry (0.41 g $CaSO_4$/ml dd H2O) was added at a ratio of 40 μl of $CaSO_4$ for 1 mL of alginate and vigorously mixed. The resulting solution was immediately expressed into the molds 2 mm depth. A sterile glass plate was placed over the mold and, after the alginate had completely gelled for 30 min, square of 5 mm×5 mm were cut using a blazer. To produce macro-porous scaffolds with open interconnected pores, the gels were cooled to −80° C., and the gels were lyophilized and stored at −20° C. until cell seeding. Fifty μl (100,000 cells/gel) of a cell suspension ($2\times10^6$ cells/ml) was gently poured onto modified open-pore polymer scaffolds. The gel were incubated for about 20 min before adding a 500 μl of complete culture medium. The experiments were done in 12 well plates.

Growth factors incorporation and release were evaluated as follows. To determine the release kinetics of the growth factors incorporated into modified binary alginate scaffolds, a quantitative sandwich enzyme immunoassay technique (ELISA) was employed. Recombinant proteins (Santa Cruz Biotechnology) was incorporated into alginate solutions prior to gelling and gels were cast as previously described. After the gels had completely polymerized, they were cut into 5 mm squares and placed in 24 well plates, and 1 mL of PBS was added to each well. At various time points, the PBS was removed and stored at −80° C. and fresh PBS was added to the scaffolds. The PBS samples were measured for total GF content via quantitative ELISA (Quantikine, Minneapolis, Minn.), and the results were compared to the initially incorporated GF.

Myoblast purification culture, and characterization were carried out as follows. Primary myoblasts and both C2C12 and GFP-PMM23.8 cell lines were used. Myoblasts were derived from 4-12 weeks-old C57BL/6 and transgenic Tg(ACTbEGFP)1Osb, constitutively express GFP in all the cells, mice skeletal musculature. Under sterile conditions, the all musculature was surgically excised, finely minced, and disassociated in 0.02% Trypsin (Gibco/Invitrogen) and 2% collagenase type 4 (Worthington Biochemical, Lakewood, N.J.) for 60 min at 37° C./5% $CO_2$ while agitating on an orbital shaker. Disassociated cells were strained through a 70 μm sieve, centrifuged at 1600 rpm for 5 min, and re-suspended in high-glucose DMEM, with added pyruvate (Gibco). The medium was further supplemented with 10% fetal bovine serum (FBS) and 10% penicillin/streptomycin (P/S, Gibco) and this was used in all cell culture studies (for both primary and cell line). Cells were plated and cultured at 37° C./5% $CO_2$ for 72 h before media change. After 72 h in culture, the media were changed every 48 h until cells were 80% confluent (about 7 days). Cells were collected via centrifugation and overlaid on a Percoll gradient (Amersham Biosciences, Uppsala, Sweden) in a 15 mL Falcon tube. The gradient consisted of 3 mL of 20% Percoll diluted in DMEM (Invitrogen), 3 mL of 30% Percoll diluted in PBS (Gibco), and 3 mL of 50% Percoll diluted in DMEM (Invitrogen). Cells were immediately centrifuged at 1600 rpm for 20 min at 25° C. The cells from the 30% fraction were collected and re-suspended in high-glucose DMEM.

Immunohistochemistry analysis was carried out as follows. To characterize myoblast cultures for the expression of myogenic proteins, Percoll purified primary myoblasts were plated on sterile cover slips overnight and fixed in 0.2% paraformaldehyde for 20 min. Cover slips were rinsed in phosphate-buffered saline with 0.5% Triton-X (PBS-X) and incubated in Hoechst nuclear dye (1:1000). Cover slips were also incubated in an anti-desmin (1/100) monoclonal antibody (Chemicon, Temecula, Calif.) followed by immunofluorescent secondary antibody (1:1000) (FITC, Jackson Labs, West Grove, Pa.). After secondary antibody binding, cover slips were mounted on glass slides with aqueous mounting medium and sealed with clear nail polish. Slides were viewed with a conventional fluorescent light microscope (Nikon Eclipse E-800, Tokyo, Japan) or stored in total darkness for later analysis. Images were captured utilizing NIH imaging software (Bethesda, Md.), Spot digital camera (Sterling Heights, Mich.), and Adobe Photoshop (San Jose, Calif.).

Viability and proliferation were evaluated. To analyze the cell viability and proliferation within the scaffolds, the scaffolds were finely minced and treated with 1 mL of trypsin for 1 min at 37° C. and 7 mL 50 mM EDTA for 15 min at 37° C. All the volume (8 mL) of dissolved alginate and suspended cells were then counted under Coulter Cell (using as a blank the 50 mM EDTA), and 1 mL of this solution was then analysed for cell viability with V Cell via Trypan Blue exclusion (dead cells appear blue due to their inability to exclude Trypan Blue from their nucleus).

To measure the cell ability to migrate outward the scaffold, myoblasts were seeded in three-dimensional alginate scaffolds ($2 \times 10^6$ cell/mL) in 24 well plates. In particular, a solution of cells in medium (30 μL) was pipetted into each lyophilized scaffold; the medium was rapidly absorbed. The resulting viability and migration of myoblasts from alginate scaffolds incorporating several GFs alone or in combination was subsequently measured by maintaining scaffolds in culture for various time points. To measure the outward migration of myoblasts, scaffolds were placed in new plates (24 well plates) every 24 hours, and the cells that had colonized the plates over the previous 24 h were removed via trypsinization and counted in a Coulter counter (Beckman) using as a blank the isotonic solution. The total number of cells that migrated out of the scaffold was normalized to the total number of cells initially seeded into the alginate scaffolds. Cells from separate isolations were used to generate each data set, and duplication of experiments with cells from a second, independent isolation was performed to confirm results.

To determine the speed of wound healing purified primary myoblasts were cultured in two-dimensional plates ($2 \times 10^6$ cell/mL) until a nearly confluency (95%). A straight width limited scratch, simulating a wound, was generated with a 0.5-10 μl pipet tip under an angle of 30° along the middle line of the plate. The plate was then transferred to a microscope stage in a incubator maintained at 37° C. and 5% $CO_2$, and the front of cells migrating into the wounded area was recorded. Acquisitions were taken every 10 min for 18 hours.

Scanning electron microscopy (SEM) was also used to characterize the scaffold delivery vehicles. The size and morphology of the pores in alginate scaffolds were imaged utilizing a scanning electron microscope (ISIDS 130, Topcon Techn. CA, Tokyo, Japan). All samples were dried and sputter coated (Desk II, Denton Vacuum, Moorestown, N.J.) prior to analysis. All statistical analysis was done using ANOVA test. Differences between conditions were considered significant if $p<0.05$.

Vascular Endothelial Growth Factor (VEGF, Also Known as VEGF-A)

The term "VEGF" broadly encompasses two families of proteins that result from the alternate splicing of a single gene, VEGF, composed of 8 exons. The alternate splice sites reside in the exons 6, 7, and 8. However, the alternate splice site in the terminal exon 8 is functionally important. One family of proteins arise from the proximal splice site and are denoted ($VEGF_{xxx}$). Proteins produced by alternate splicing at this proximal location are PRO-angiogenic and are expressed conditionally (for instance, when tissues are hypoxic and secreted signals induce angiogenesis). The other family of proteins arise from the distal splice site and are denoted ($VEGF_{xxx}b$). Proteins produced by alternate splicing at this distal location are ANTI-angiogenic and are expressed in healthy tissues under normal conditions.

VEGF exons 6 and 7 contain splice sites (result in the inclusion or exclusion of exons 6 and 7) that affect heparin binding affinity and amino acid number. Humans comprise $VEGF_{121}$, $VEGF_{121}b$, $VEGF_{145}$, $VEGF_{165}$, $VEGF_{165}b$, $VEGF_{189}$, and $VEGF_{206}$. Heparin binding affinity, interactions with heparin surface proteoglycans (HSPGs) and neuropilin co-receptors on the cell surface mediated by amino acid sequences in exons 6 and 7 enhance the ability of VEGF variants to activate VEGF signaling receptors (VEGFRs).

Endogenous VEGF splice variants are released from cells as glycosylated disulfide-bonded dimers. Structurally VEGF belongs to the PDGF family of cysteine-knot growth factors comprising Placenta growth factor (PlGF), VEGF-B, VEGF-C and VEGF-D (the VEGF sub-family of growth factors). VEGF is sometimes referred to as VEGF-A to differentiate it from these related growth factors. The term "VEGF" used herein to describe the present invention is meant to refer to VEGF-A.

Members of the VEGF family stimulate cellular responses by binding to cell-surface tyrosine kinase receptors (the VEGFRs). VEGF-A binds to VEGFR-1 (also known as Flt-1) and VEGFR-2 (also known as KDR/Flk-1). VEGFR-2 is the predominant receptor for VEGF-A mediating almost all of the known cellular responses to this growth factor. The function of VEGFR-1 is unclear, although it is thought to modulate VEGFR-2 signaling. VEGFR-1 may also sequester VEGF from VEGFR-2 binding (which may be important during development).

Compositions, methods, and devices of the present invention comprise all VEGF polypeptides generated from alternative splicing including pro- and anti-angiogenic forms.

Devices of the present invention administered to a subject contain only pro-angiogenic VEGF polypeptide splice forms. Alternatively, or in addition, devices of the present invention administered to a subject contain a mixture of pro- and anti-angiogenic VEGF polypeptide splice forms. Pro- and anti-angiogenic VEGF polypeptide splice forms are released by the scaffold composition of the device simultaneously or sequentially. For example, the opposing splice forms are released together in order to achieve a precise level of stimulation. Alternatively, the opposing splice forms are released sequentially to stimulate angiogenesis and subsequently attenuate the signal when the desired result has been achieved. In another embodiment, devices comprising pro-angiogenic VEGF polypeptide splice forms are placed at the target tissue site while devices comprising anti-angiogenic VEGF polypeptide splice forms are placed in surrounding tissues in order to prevent pro-angiogenic signals from disseminating into and stimulating non-target tissue.

Exemplary VEGF polypeptide splice forms comprised by the compositions, methods, and devices of the present invention include, but are not limited to, the polypeptides described by the following sequences and SED ID NOs. VEGF polypeptide splice forms are released from compositions, scaffolds, or devices of the present invention as naked, or glycosylated polypeptides. Alternatively, or in addition, VEGF polypeptide splice forms are monomers or disulfide-bonded dimers. In a preferred embodiment, VEGF polypeptide splice forms are released into target tissues from compositions, scaffolds, and/or devices of the present invention as glysosylated disulfide-bonded dimers.

Human $VEGF_{148}$ comprises the following amino acid sequence (NCBI Accession No. NP_001020540 and SEQ ID NO: 1):

```
  1 mtdrqtdtap spsyhllpgr rrtvdaaasr gqgpepapgg gvegvgargv alklfvqllg
 61 csrfggavvr ageaepsgaa rsassgreep qpeegeeeee keeergpqwr lgarkpgswt
121 geaavcadsa paarapqala rasgrggrva rrgaeesgpp hspsrrgsas ragpgraset
181 mnfllswvhw slalllylhh akwsqaapma egggqnhhev vkfmdvyqrs ychpietlvd
241 ifqeypdeie yifkpscvpl mrcggccnde glecvptees nitmqimrik phqgqhigem
301 sflqhnkcec rpkkdrarqe npcgpcserr khlfvqdpqt ckcsckntds rckm
```

Human $VEGF_{165}$ comprises the following amino acid sequence (NCBI Accession No. NP_001020539 and SEQ ID NO: 2):

```
  1 mtdrqtdtap spsyhllpgr rrtvdaaasr gqgpepapgg gvegvgargv alklfvqllg
 61 csrfggavvr ageaepsgaa rsassgreep qpeegeeeee keeergpqwr lgarkpgswt
121 geaavcadsa paarapqala rasgrggrva rrgaeesgpp hspsrrgsas ragpgraset
181 mnfllswvhw slalllylhh akwsqaapma egggqnhhev vkfmdvyqrs ychpietlvd
241 ifqeypdeie yifkpscvpl mrcggccnde glecvptees nitmqimrik phqgqhigem
301 sflqhnkcec rpkkdrarqe npcgpcserr khlfvqdpqt ckcsckntds rckarqleln
361 ertcrcdkpr r
```

Human $VEGF_{165}b$ comprises the following amino acid sequence (NCBI Accession No. NP_001028928 and SEQ ID NO: 3):

```
  1 mtdrqtdtap spsyhllpgr rrtvdaaasr gqgpepapgg gvegvgargv alklfvqllg
 61 csrfggavvr ageaepsgaa rsassgreep qpeegeeeee keeergpqwr lgarkpgswt
121 geaavcadsa paarapqala rasgrggrva rrgaeesgpp hspsrrgsas ragpgraset
181 mnfllswvhw slalllylhh akwsqaapma egggqnhhev vkfmdvyqrs ychpietlvd
241 ifqeypdeie yifkpscvpl mrcggccnde glecvptees nitmqimrik phqgqhigem
301 sflqhnkcec rpkkdrarqe npcgpcserr khlfvqdpqt ckcsckntds rckarqleln
361 ertcrsltrk d
```

Human VEGF$_{183}$ comprises the following amino acid sequence (NCBI Accession No. NP_001020538 and SEQ ID NO: 4):

```
  1 mtdrqtdtap spsyhllpgr rrtvdaaasr gqgpepapgg gvegvgargv alklfvqllg
 61 csrfggavvr ageaepsgaa rsassgreep qpeegeeeee keeergpqwr lgarkpgswt
121 geaavcadsa paarapqala rasgrggrva rrgaeesgpp hspsrrgsas ragpgraset
181 mnfllswvhw slalllylhh akwsqaapma egggqnhhev vkfmdvyqrs ychpietlvd
241 ifqeypdeie yifkpscvpl mrcggccnde glecvptees nitmqimrik phqgqhigem
301 sflqhnkcec rpkkdrarqe kksvrgkgkg qkrkrkksrp cgpcserrkh lfvqdpqtck
361 cscknsdsrc karqlelner tcrcdkprr
```

Human VEGF$_{189}$ comprises the following amino acid sequence (NCBI Accession No. NP_003367 and SEQ ID NO: 5):

```
  1 mtdrqtdtap spsyhllpgr rrtvdaaasr gqgpepapgg gvegvgargv alklfvqllg
 61 csrfggavvr ageaepsgaa rsassgreep qpeegeeeee keeergpqwr lgarkpgswt
121 geaavcadsa paarapqala rasgrggrva rrgaeesgpp hspsrrgsas ragpgraset
181 mnfllswvhw slalllylhh akwsqaapma egggqnhhev vkfmdvyqrs ychpietlvd
241 ifqeypdeie yifkpscvpl mrcggccnde glecvptees nitmqimrik phqgqhigem
301 sflqhnkcec rpkkdrarqe kksvrgkgkg qkrkrkksry kswsvpcgpc serrkhlfvq
361 dpqtckcsck ntdsrckarq lelnertcrc dkprr
```

Human VEGF$_{206}$ comprises the following amino acid sequence (NCBI Accession No. NP_001020537 and SEQ ID NO: 6):

```
  1 mtdrqtdtap spsyhllpgr rrtvdaaasr gqgpepapgg gvegvgargv alklfvqllg
 61 csrfggavvr ageaepsgaa rsassgreep qpeegeeeee keeergpqwr lgarkpgswt
121 geaavcadsa paarapqala rasgrggrva rrgaeesgpp hspsrrgsas ragpgraset
181 mnfllswvhw slalllylhh akwsqaapma egggqnhhev vkfmdvyqrs ychpietlvd
241 ifqeypdeie yifkpscvpl mrcggccnde glecvptees nitmqimrik phqgqhigem
301 sflqhnkcec rpkkdrarqe kksvrgkgkg qkrkrkksry kswsvyvgar cclmpwslpg
361 phpcgpcser rkhlfvqdpq tckcsckntd srckarqlel nertcrcdkp rr
```

Insulin-Like Growth Factor (IGF-1)

IGF-1 is a single chain polypeptide of 70 amino acids crosslinked by three disulfide bridges. (Rinderknecht et al., 1978, J. Biol. Chem. 253:2768-2776; sequence on p. 2771, hereby incorporated by reference). Human IGF-1 comprises the following amino acid sequence (GenBank: CAA01954.1 and SEQ ID NO: 7). Human IGF-1 can be purchased from R&D Systems (614 McKinley Place NE. Minneapolis, Minn. 55413)

```
  1 mgpetlcgae lvdalqfvcg drgfyfnkpt gygsssrrap qtgmvdeccf rscdkrrlem
 61 ycaplkpaks a
```

Human IGF-1B isoform comprises the following sequence (GenBank: CAA40093.1; SEQ ID NO: 8). The mature peptide comprises residues 49-118.

```
  1 mgkisslptq lfkccfcdfl kvkmhtmsss hlfylalcll tftssatagp etlcgaelvd
 61 alqfvcgdrg fyfnkptgyg sssrrapqtg ivdeccfrsc dlrrlemyca plkpaksars
121 vraqrhtdmp ktqkyqppst nkntksqrrk gwpkthpgge qkegteaslq irgkkkeqrr
181 eigsrnaecr gkkgk
```

Myoblast Transfer Therapy (MTT)

The descendents of satellite cells—myoblasts—have been considered as powerful candidates for cell-based therapies to treat muscle injury, muscular dystrophies, and other neuromuscular diseases. Myoblast transfer therapy (MTT) involves the intramuscular injection into host muscle of cultured muscle precursor cells—myoblasts are isolated from normal donor skeletal muscles, expanded in vitro, and injected to the muscle injury site of the recipient. However prior to the invention, this treatment was limited by the rapid and massive death of donor myoblasts following injection into the host muscle. The failure of MTT was due to a number of different reasons: host immune rejection to the injected myoblasts, poor migration of the cells, reduced cell myogenic potential after in vitro culture, mechanical stress, limited availability of oxygen and/or nutrient supply, and delayed clearance of metabolites. The invention solves these problems of earlier approaches in three significant ways: (1) the hydrogel delivery device provides temporary housing by virtue of its porosity and presence of ECM compositions (e.g., RGD-containing peptides) to mediate temporary adhesion of cells; (2) the presence of IGF in or on the delivery device induces migration of the cells (e.g., satellite cells or myoblasts) out of the scaffold device and into the subject's muscular tissue; and (3) VEGF in or on the device promotes a host angiogenic response. As a result, implantation of the VEGF-containing, IGF-containing, cell-seeded, ECM-derivatized hydrogel leads to enhanced muscle generarion that is superior to previous approaches.

Scaffold Compositions and Architecture

Components of the scaffolds are organized in a variety of geometric shapes (e.g., beads, pellets), niches, planar layers (e.g., sheets). For example, sheetlike are used in bandages or wound dressings. The device is placed on or administered into a target tissue. Devices are introduced into or onto a bodily tissue using a variety of known methods and tools, e.g., spoon, tweezers or graspers, hypodermic needle, endoscopic manipulator, endo- or trans-vascular-catheter, stereotaxic needle, snake device, organ-surface-crawling robot (United States Patent Application 20050154376; Ota et al., 2006, Innovations 1:227-231), minimally invasive surgical devices, surgical implantation tools, and transdermal patches.

A scaffold or scaffold device is the physical structure upon which or into which cells associate or attach, and a scaffold composition is the material from which the structure is made. For example, scaffold compositions include biodegradable or permanent materials such as those listed below. The mechanical characteristics of the scaffold vary according to the application or tissue type for which regeneration is sought. It is biodegradable (e.g., collagen, alginates, polysaccharides, polyethylene glycol (PEG), poly(glycolide) (PGA), poly(L-lactide) (PLA), or poly(lactide-co-glycolide) (PLGA) or permanent (e.g., silk). In the case of biodegradable structures, the composition is degraded by physical or chemical action, e.g., level of hydration, heat or ion exchange or by cellular action, e.g., elaboration of enzyme, peptides, or other compounds by nearby or resident cells. The consistency varies from a soft/pliable (e.g., a gel) to glassy, rubbery, brittle, tough, elastic, stiff. The structures contain pores, which are nanoporous, microporous, or macroporous, and the pattern of the pores is optionally homogeneous, heterogenous, aligned, repeating, or random.

Alginates are versatile polysaccharide based polymers that may be formulated for specific applications by controlling the molecular weight, rate of degradation and method of scaffold formation. Coupling reactions can be used to covalently attach bioactive epitopes, such as the cell adhesion sequence RGD to the polymer backbone. Alginate polymers are formed into a variety of scaffold types. Injectable hydrogels can be formed from low MW alginate solutions upon addition of a cross-linking agents, such as calcium ions, while macroporous scaffolds are formed by lyophilization of high MW alginate discs. The cross-linking is ionic or covalent (as in the case of shape-memory delivery devices).

Differences in scaffold formulation control the kinetics of scaffold degradation. Release rates of morphogens or other bioactive substances from alginate scaffolds is controlled by scaffold formulation to present morphogens in a spatially and temporally controlled manner. This controlled release not only eliminates systemic side effects and the need for multiple injections, but can be used to create a microenvironment that activates host cells at the implant site and transplanted cells seeded onto a scaffold.

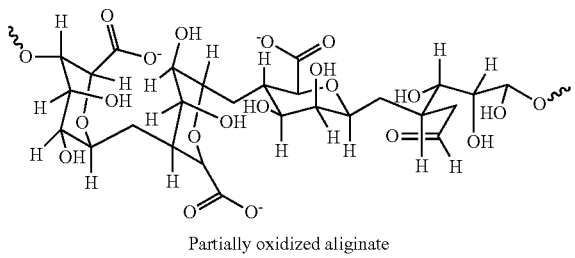

Partially oxidized alginate

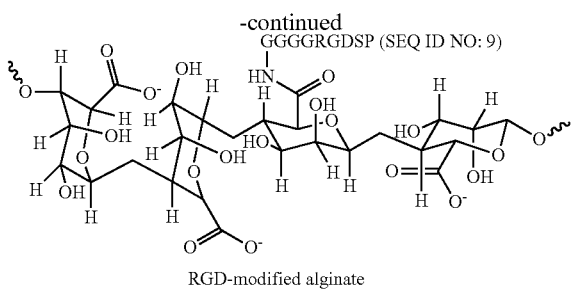
GGGGRGDSP (SEQ ID NO: 9)

RGD-modified alginate

The scaffold comprises a biocompatible polymer matrix that is optionally biodegradable in whole or in part. A hydrogel is one example of a suitable polymer matrix material. Examples of materials which can form hydrogels include polylactic acid, polyglycolic acid, PLGA polymers, alginates and alginate derivatives, gelatin, collagen, agarose, natural and synthetic polysaccharides, polyamino acids such as polypeptides particularly poly(lysine), polyesters such as polyhydroxybutyrate and poly-epsilon.-caprolactone, polyanhydrides; polyphosphazines, poly(vinyl alcohols), poly(alkylene oxides) particularly poly(ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers.

The scaffolds are fabricated from a variety of synthetic polymers and naturally-occurring polymers such as, but not limited to, collagen, fibrin, hyaluronic acid, agarose, and laminin-rich gels. One preferred material for the hydrogel is alginate or modified alginate material. Alginate molecules are comprised of (1-4)-linked β-D-mannuronic acid (M units) and α L-guluronic acid (G units) monomers, which can vary in proportion and sequential distribution along the polymer chain. Alginate polysaccharides are polyelectrolyte systems which have a strong affinity for divalent cations (e.g. $Ca^{+2}$, $Mg^{+2}$, $Ba^{+2}$) and form stable hydrogels when exposed to these molecules. See Martinsen A., et al., Biotech. & Bioeng., 33 (1989) 79-89.) For example, calcium cross-linked alginate hydrogels are useful for dental applications, wound dressings chondrocyte transplantation and as a matrix for other cell types.

An exemplary device utilizes an alginate or other polysaccharide of a relatively low molecular weight, preferably of size which, after dissolution, is at the renal threshold for clearance by humans, e.g., the alginate or polysaccharide is reduced to a molecular weight of 1000 to 80,000 daltons. Preferably, the molecular mass is 1000 to 60,000 daltons, particularly preferably 1000 to 50,000 daltons. It is also useful to use an alginate material of high guluronate content since the guluronate units, as opposed to the mannuronate units, provide sites for ionic crosslinking through divalent cations to gel the polymer. U.S. Pat. No. 6,642,363, incorporated herein by reference discloses methods for making and using polymers containing polysaccharides such as alginates or modified alginates that are particularly useful for cell transplantation and tissue engineering applications.

Useful polysaccharides other than alginates include agarose and microbial polysaccharides such as those listed in the table below.

| Polysaccharide Scaffold Compositions | |
|---|---|
| Polymers[a] | Structure |
| Fungal | |
| Pullulan (N) | 1,4-;1,6-α-D-Glucan |
| Scleroglucan (N) | 1,3;1,6-α-D-Glucan |
| Chitin (N) | 1,4-β-D-Acetyl Glucosamine |
| Chitosan (C) | 1,4-β.-D-N-Glucosamine |
| Elsinan (N) | 1,4-;1,3-α-D-Glucan |
| Bacterial | |
| Xanthan gum (A) | 1,4-β.-D-Glucan with D-mannose; D-glucuronic Acid as side groups |
| Curdlan (N) | 1,3-β.-D-Glucan (with branching) |
| Dextran (N) | 1,6-α-D-Glucan with some 1,2;1,3-; 1,4-α-linkages |
| Gellan (A) | 1,4-β.-D-Glucan with rhamose, D-glucuronic acid |
| Levan (N) | 2,6-β-D-Fructan with some β-2,1-branching |
| Emulsan (A) | Lipoheteropolysaccharide |
| Cellulose (N) | 1,4-β-D-Glucan |

[a]N—neutral, A = anionic and C = cationic.

Alginate Hydrogels as Cell/Growth Factor Delivery Vehicles

Hydrogels are made from water-soluble polymers and are a class of three-dimensional, water-swollen cross-linked homopolymers or copolymers. Alginates are a class of hydrogel-forming material that has been widely utilized in tissue engineering and drug delivery applications. They are a naturally derived polysaccharide, extracted from brown algae. Their chemical structure shows that they are copolymers of (1,4)-linked b-D-mannuronic acid (M) and a-L-guluronic acid (G). Alginate hydrogels are highly hydrated three-dimensional networks and their structure resembles the native ECM of tissues.

Alginate hydrogels have been used in the food industry and medicine due to their high biocompatibility and advantageous physical and chemical properties. Alginate hydrogels are easy to fabricate and process, and can be readily formed into defined structures and form three-dimensional matrices in a hydrated state. High water content is another unique property that makes alginate hydrogels resemble native tissues and thus makes them a good candidate material for cell culture matrix for tissue repair. In addition, they have material properties that are readily tunable by varying the type and degree of cross linking in the polymer network and other chemical or physical modifications.

Example 1

Functional Muscle Regeneration with Combined Delivery of Angiogenesis and Myogenesis Factors Studies were carried out to investigate an interplay between VEGF and IGF-1 in ischemic muscle regeneration, and the possibility that dual sustained delivery of these two critical morphogens could induce the regeneration of functional muscle in ischemic hindlimbs. The impact of the distance of the muscle from the factor delivery site on the regeneration process was also examined by analysing distinct muscles in the hindlimbs. As targets for these experiments, we chose the gracilis and tibialis muscles, respectively corresponding to the muscle site of injection and a muscle distant to the site of polymer placement. The ultimate goal of this approach is to preserve the local progenitor cells from apoptosis and necrosis during the degeneration process, and instead to activate the progenitor cells to enter the proliferative phase and differentiate into contractile muscle fibers to regenerate functional tissue.

Regenerative efforts typically focus on the delivery of single factors, but it is likely that multiple factors regulating distinct aspects of the regenerative process (e.g., vascularization and stem cell activation) can be utilized in parallel to affect regeneration of functional tissues. This possibility was addressed in the context of ischemic muscle injury, which typically leads to necrosis and loss of tissue and function. The role of sustained delivery, via injectable gel, of a combination of vascular endothelial growth factor (VEGF) to promote angiogenesis and insulin growth factor-1 (IGF-1) to directly promote muscle regeneration and the return of muscle function in ischemic rodent hindlimbs was investigated. Sustained VEGF delivery alone led to neo-angiogenesis in ischemic limbs with complete return of tissue perfusion to normal levels by 3 weeks, as well as protection from hypoxia and tissue necrosis, leading to an improvement in muscle contractility. Sustained IGF-1 delivery alone was found to enhance muscle fiber regeneration and, protected cells from apoptosis. However, the combined delivery of VEGF and IGF-1 led to parallel angiogenesis, reinnervation and myogenesis, as satellite cell activation and proliferation was stimulated, cells were protected from apoptosis, the inflammatory response was muted, and highly functional muscle tissue was formed. In contrast, bolus delivery of factors did not have any benefit in neoangiogenesis and perfusion, and minimal effect on muscle regeneration. These results support the utility of simultaneously targeting distinct aspects of the regenerative process.

The following materials and methods were used to generate the data described in Example 1.

Growth Factor Incorporation and Release Kinetics

Ultrapure MVG alginate was purchased from ProNova Biomedical (Norway). Biodegradable gels were formed from a combination of polymer molecular weights. Alginates were reconstituted in EBM-2 (Cambrex Corporation, Walkersville, Md., USA) to obtain a 2% w/v solution prior to gelation, and cross-linked with aqueous slurries of a calcium sulphate solution (0.21 g CaSO4/mL dH2O) at a ratio of 25:1 (40 pl of CaSO4 per 1 mL of 2% w/v alginate solution). Alginates were pre-mixed with recombinant human $_{VEGF165}$ protein (generously provided by Biological Resources Branch of the National Cancer Institute) and/or with recombinant human IGF1 (R&D System), at a final concentration of 60 pg/mL for each protein; in vitro release kinetics were measured using ELISA. Mixtures were allowed to gel for 30 min, and maintained at 4° C. prior to animal injections.

Animals and Surgical Procedures

Female C57BL/6J mice (6-7 weeks; Jackson Laboratories, Bar Harbour, Me., USA) were anesthetized with an intraperitoneal injection of a mixture of ketamine 80 mg/kg and xylazine 5 mg/kg prior to all surgical procedures. Hindlimb ischemia was induced by unilateral external iliac and femoral artery and vein ligation. After the vessel ligation, mice were injected with a total volume of 50 pl of alginate gel containing 3 pg of $_{VEGF165}$ and/or 3 pg of IGF1, gel containing 3 pg of IGF-1, gel with no GFs, or a PBS solution containing 3 pg of $_{VEGF165}$ and 3 pg of IGF-1 (bolus delivery). Injections were performed using a 25 G needle (Becton Dickinson, Franklin Lakes, N.J., USA), directly into the gracilis muscle (1-3 mm inside the muscle) at the site of vessel ligation. The incision was surgically closed, and animals monitored over time.

For analysis of reinnervation, hindlimb ischemia and gel delivery were carried out as described in transgenic C57BL/6 mice selectively expressing yellow fluorescent protein (YFP) under control of a thy-1 promoter in motoneurons.

Ischemia, Perfusion and Hypoxia Analysis

Measurements of the ischemic/normal limb blood flow ratio were performed on anesthetized animals (n=10) using a LDPI analyzer (Perimed AB, Stockholm, Sweden). Perfusion measurements were obtained by scanning entire hindlimbs under basal conditions and then weekly after surgery, and the ratio of perfusion of the ischemic to non-ischemic limb of the same animal was calculated. Tissue hypoxia was visualized in tissue sections using hydroxyprobe reagent, as per supplier instructions (Chemicon).

Histological Assessment of Skeletal Muscle

Mice were sacrificed and hindlimb muscle tissues (n=10 per time point per experimental condition) were processed for histological analyses. For regeneration metrics, the samples were stained with H&E, and fiber diameter and the number of centrally located nuclei were analyzed. Vascular ECs were identified by immunostaining for mouse CD31 (BD Biosciences Pharmingen, San Diego, Calif., USA). For measurement of capillary densities, histological analysis was performed in a blinded fashion as described. Immunostaining for Ki-67 (Ki-67 mouse IgG1, Dako, Carpinteria, Calif.) was performed to identify cell proliferation. Qualitative analysis of apoptosis was assessed by TUNEL assay (Roche). Interstitial fibrosis was morphometrically assessed in Masson Trichrome (Sigma Aldrich) stained sections.

Analysis of Reinnervation

Mice were anesthetized by an intraperitoneal injection of ketamine/xylazine and fixed by transcardial injection of 4% paraformaldehyde. The tibialis muscle was explanted, and stained with Alexa594-bungarotoxin (Invitrogen, Frederick, Md.) to visualize acetylcholine receptors. Innervation at the neuromuscular junction was imaged using a Zeiss Pascal 5 LSM upright laser scanning confocal microscope using an Ar laser to excite YFP at 488 nm, and a He/Ne laser to excite Alexa594 bungarotoxin at 543 nm. All images were processed using Zeiss software and images are displayed as Z-maximum intensity projections. Reinnervation was quantified by counting sites of overlap of motor neuron axon (yellow) and endplate (red) as a site of reinnervation. At least 50 NMJs were counted for each condition. Statistical significance was determined using unpaired ANOVA analysis.

Mechanical Measurements

Intact gracilis and tibialis muscles were dissected (n=5/condition), mounted vertically midway between two fine cylindrical parallel steel wire electrodes (1.6 mm diameter, 21 mm long), attached by their tendons to microclips connected to a force transducer (FORT 25, WPII, Sarasota, Fla., USA) and bathed in a physiological saline solution in a chamber oxygenated with 95% $O_2$-5% $CO_2$ at 25° C. Muscle length was adjusted until maximum twitch force was achieved (100-300 Hz). A wave pulse was initiated from a computer using a custom-written Lab VIEW program and delivered to the stimulation electrodes via a purpose-built power amplifier (QSC USA 1310). A switch on the amplifier permitted stimulation via wire electrodes. Contractions were continuously monitored on a LabView chart recorder, and contractions saved on a PC. Contractions were evoked every 5 min. Tetani were usually evoked at 3 00 Hz-1 5-20V with constant pulse width and train duration of 2 ms and 1 s, respectively. These stimulation frequencies and voltages were required to generate maximum force but exceed the naturally occurring median firing frequencies of 100-200 Hz in tibialis and gracilis. After force measurements were completed, the muscles were removed from the bath and weighed. Peak tetanic force was determined as the difference between the maximum force during a contraction and the baseline level, and specific force calculated by normalization by muscle weight.

Statistical Analyses

All results are expressed as mean±standard deviation (SD). Multivariate repeated-measures ANOVA was performed to test for interactions between conditions. Differences between conditions were considered significant if p value<0.05.

Dual Sustained Delivery of VEGF and IGF-1

Dual sustained delivery of these two critical morphogens induces the regeneration of functional muscle in ischemic hindlimbs. The impact of the distance of the muscle from the factor delivery site on the regeneration process was examined by analysing distinct muscles in the hindlimbs. The gracilis and tibialis muscles were chosen for the muscle site of injection and a muscle distant to the site of polymer placement, respectively. The goal of this approach was to preserve the local progenitor cells from apoptosis and necrosis during the degeneration process, and instead to activate the progenitor cells to enter the proliferative phase and differentiate into contractile muscle fibers to regenerate functional tissue.

Sustained VEGF&IGF-1 Presentation Enhance Muscle Size and Limb Vascularization

An ischemia injury was selected for these studies following analysis of the spontaneous recovery of muscle mechanical function subsequent to various types of injuries, including partial laceration, cryoinjury, and notexin injection. Ischemia led to the greatest loss of muscle function, as compared to the other injury models, and the least spontaneous return of function. Further, analysis of tissue sections 2 wks following injury revealed a largely necrotic defect with diffusely disorganized and disrupted/broken myofibers in the ischemic condition, supporting the stringency of this model.

Mice were treated at the time of induction of severe hindlimb ischemia with an injectable, degradable alginate gel. In vitro, after an initial burst, VEGF was released in a sustained manner over time, while IGF, due to its smaller size (7.5 Kda) and its non-heparin binding nature showed a faster release, approximately 80% of the total IGF loaded was released in the first 24 h. The following five interventions were analysed: (i) blank alginate gel, (ii) alginate gel delivering VEGF (3 ug), (iii) alginate gel delivering VEGF and IGF-1 (3 ug each), (iv) alginate gel delivering IGF-1 (3 ug), and (v) bolus delivery of VEGF and IGF-1 (3 ug each) in PBS.

Significant muscle loss was noted at seven weeks post-surgery with blank gel treatment, while injured muscles treated with gel containing both GFs were grossly larger. Quantification of the weight of these muscles revealed insignificant changes with gel releasing either VEGF or IGF alone, or with the saline bolus treatment, whereas statistically significant increases of 26%±11 and 30%±22 occurred for the tibialis (distant to gel injection) and gracilis muscles (site of gel injection) respectively, receiving gel releasing both GFs as compared with the blank treatment. The large standard deviations in the gracilis muscle analysis were due to the difficulty in isolating the gracilis muscle from the other tightly associated muscles.

As the effects of the VEGF delivery on muscle regeneration were likely mediated by its effects on angiogenesis, the level of muscle hypoxia, perfusion of ischemic tissues, and tissue necrosis were next analyzed. Immunohistochemical analysis of tibialis and gracilis muscle tissues revealed that VEGF-delivering alginate gels (alginate/VEGF, and alginate VEGF/IGF-1) increased muscle blood vessel densities, as compared with injection of a blank vehicle or bolus delivery of VEGF/IGF. In particular, at 7 wks, VEGF delivery from the gels resulted in an approximately 2-fold increase in vessel density in tibialis muscle and 3-fold increase in the gracilis muscle, as compared to the ischemic hindlimb treated with the blank alginate. IGF delivery alone had no significant effect on vascularization in the gracilis muscle, and a modest effect in the tibialis. The bolus delivery had no effect on blood vessel densities, as compared to the controls.

A Laser Doppler Perfusion Imaging (LDPI) system was used to quantify perfusion. The regional blood flow was reduced immediately after surgery to approximately 20% of normal in all conditions, as expected. Alginate gel only treatment led to a slow increase in reperfusion over time, and the ischemic limbs for the most part remained necrotic. Bolus delivery resulted in little difference from the no-treatment control or blank alginate injection. In contrast, VEGF and dual GF delivery from the vehicle led to a final recovery of respectively 80% and 95% of normal limbs. In particular, animals treated with alginate gels delivering VEGF/IGF-1 showed a marked increase in blood flow starting around the $4^{th}$ week after the injury, and an additional 20% increase at 7 weeks compared with the control. The level of tissue necrosis was also quantified by visual observation. Hindlimb ischemia led to severe toe or foot gangrene in control animals, but treatment with alginate gel with VEGF and VEGF/IGF largely spared the limbs from necrosis. Protection of myofibers from hypoxia was also observed with alginate gel VEGF and VEGF/IGF delivery, as based on hypoxia immunostaining.

VEGF and IGF-1 Induce Myoblast Proliferation and Protect Against Apoptosis

Immunostaining of tissue sections against the proliferation-associated protein Ki67 was performed to determine cell proliferation activity at early (2 weeks) and late (7 weeks) times. Abundant expression of Ki67 was detected in muscle tissues receiving alginate gels releasing VEGF alone and VEGF/IGF-1 in both tibialis and gracilis muscles at 2 weeks and 7 weeks. A less pronounced increase was observed with alginate gel delivering IGF, while no proliferation was observed in muscles treated with the blank vehicle. Furthermore, triple immunofluorescence for CD31, Ki67, and Dapi for nuclear staining suggested that both myoblasts and ECs proliferated at early stages of the reparative process. TUNEL analysis was performed to measure apoptosis in the regenerating muscles at 2 weeks post-ischemia. While significant apoptosis was observed in the blank vehicle group, apoptosis was reduced in the muscles treated with alginate delivering VEGF, and was significantly lower with vehicles delivering IGF alone. The combination of the two GFs was particularly effective in combating ischemia-induced apoptosis. Apoptosis was virtually absent in contra-lateral normoperfused muscles, as expected. Similar results were seen in five independent experiments.

Muscle Regeneration Enhanced by VEGF and IGF-1, Along with Reduced Fibrosis

To directly analyze muscle regeneration, the mean diameter of regenerated myofibers and number of centrally located nuclei in the resolving muscle tissue were quantified. The mean diameter of muscle fibers were quantitatively greater in muscles treated with alginate delivering both growth factors, as compared with alginate delivering only VEGF or IGF-1 or the two growth factors in bolus saline, in both tibialis and gracilis muscles. The tibialis muscles treated with alginate delivering VEGF or IGF-1 alone showed an approximately 10% increase in average diameter, while co-delivery of both GFs led to a 25% increase in the diameter of regenerating fibers, compared to the blank alginate gel, and a 19% increase compared to gel/VEGF ($p<0.05$). An increase was also observed in gracilis muscle with VEGF/IGF delivery from the alginate gels. At 2 wks post-injury the tibialis muscle fibers in the injury group treated with VEGF or IGF-1 alone also showed an approximately 40% increase in centrally located nuclei, versus a lesser increase of 30% with bolus factors delivery, as compared with the blank. The two factors in combination with alginate delivery led to a 53% and a 39% increase in centrally located nuclei, as compared with the blank alginate or alginate delivering VEGF alone. The number of centrally located nuclei in the gracilis fibers treated with alginate delivering both GFs increased ~70% and 20% increase, respectively, when compared with either the blank alginate or with alginate delivering VEGF only. Representative cross and longitudinal micro sections of tibialis tissue highlight the increase in centrally located myonuclei in the ischemic muscles treated with alginate delivering both GFs. Analysis of the muscle fiber types confirmed an active regenerative process induced by growth factor delivery. Type IIC fibers were noted at early times (3 days) following injury with delivery of growth factor from the gel, but were not present in uninjured control muscles or uninjured muscles treated with gel/growth factor. Further, analysis of injured muscle treated with gel delivering VEGF revealed a significant increase in myogenin positive cells, which contrasts with few myogenin-positive cells in control, uninjured muscle), also supporting an active muscle regeneration process.

Injured muscle tissue treated with blank alginate demonstrated significant interstitial fibrotic tissue. Control (non-operated) limbs demonstrated little fibrosis, as expected. However, limbs treated with alginate gel delivery of both GFs exhibited a significant decrease in fibrosis. A less pronounced reduction of fibrosis was observed with the two GFs delivered alone. Conversely, in the bolus injection condition a large content of fibrotic tissue was formed.

Growth Factor Delivery Promotes Earlier Regeneration of Damaged Neuromuscular Junctions Induction of ischemia in the hindlimb and treatment with a blank hydrogel led to a significant loss of innervation at the neuromuscular junction (NMJ) in the tibialis muscle seven days after injury in control mice; by day fourteen complete reinnervation had occurred and NMJs appeared normal. In contrast, muscles treated with either IGF-1 alone or VEGF/IGF-1 had completely reformed NMJs and no damage to receptors or muscle fibers was observed at 7 days. At this time point, VEGF delivery also resulted in robust reinnervation of NMJs, although not to a significantly greater extent than the blank hydrogel.

Dual Gel Delivery of VEGF&IGF-1 Enhances the Contraction Force of Damaged Muscles To test whether muscle changes induced by GF delivery would correspond to increased function, the contractile force of the muscles was analyzed. The weight normalized tetanic force of the tibialis and gracilis muscles were measured after maximal tetanic stimulation. Muscles treated with gel delivering both GFs showed a significant increase above normal values in the tetanic force at 2 wks postsurgery (2.3 and 7.9 fold increase, respectively, for tibialis and gracilis muscles, when compared with the blank) followed by a decrease toward the normal value at 7 wks. Animals receiving alginate delivering VEGF alone showed a similar trend, but the increase in the force of contraction was less pronounced. In particular, at 2 wks a 1.6 and 5.7 fold increase was measured, respectively in tibialis and gracilis muscles compared with alginate gel only. In contrast, the animal receiving alginate gel without GFs had a markedly lower contractile function at all time points.

The results from these studies demonstrate a beneficial interplay between VEGF and IGF-1, when delivered appropriately, in enhancing skeletal muscle regeneration, revascularization, re-innervation and gain of function following ischemic injuries. Past therapies to regenerate ischemic tissues typically relied on bolus delivery or systemic administration of single growth factors. Vascular endothelial growth factor (VEGF) specifically has been widely used as a potent pro-angiogenic initiator in many strategies to treat ischemic diseases. However, the impact on salvaging and driving regeneration of ischemic muscle has not been addressed. Moreover, an extensive body of literature supports a role for insulin growth factor-1 (IGF-1) in regulating the establishment and maintenance of the mature muscle phenotype in normal and regenerating muscle tissue both in vitro and in vivo. In particular IGF-1 has been implicated in early and late stages of muscle developmental processes playing first a role in inducing myoblast proliferation, and subsequently promoting myogenic differentiation. Past approaches to exploit GF signalling in muscle regeneration typically utilized bolus GF delivery, which leads to rapid depletion of the factors in the target tissue. Supra-physiologic concentrations of growth factors are used in an effort to offset this issue, potentially leading to unwanted side-effects.

Sustained VEGF delivery alone from alginate gels had a significant impact on angiogenesis, and tissue perfusion, but a less pronounced effect on muscle regeneration. These results are in accord to previous reports that the sustained and controlled release of VEGF from both a PLG and the same injectable alginate-based vehicle stimulated angiogenesis, returned perfusion to normal levels, and prevented necrosis in ischemic hindlimbs. VEGF has also recently been implicated in muscle regeneration and muscle reinnervation via a direct neuro-protective and neuro-directing effect. The contractile activity of skeletal muscle, and hence its functionality, are regulated by the nervous system and loss of innervation leads to a decrease in satellite cell number and muscle atrophy. The results of this study suggest delivery of VEGF alone has profound effects on muscle regeneration, as increases in the diameter of regenerating fibers and the number of centrally located nuclei in muscle fibers, both hallmarks of regenerating myofibers, were found with gel-VEGF delivery. The contractile properties of the injured muscle were also improved with appropriate VEGF delivery.

IGF-1 delivery alone from alginate gels was found to have a modest effect on muscle fiber regeneration and cell protection from apoptosis. These data are consistent with data that increased levels of IGF-1 augmented tissue DNA content (resulting from activation of satellite cells) and muscle protein synthesis within existing myofibers. Gel-IGF-1 delivery alone also induced neo-angiogenesis in the tibialis muscle, and to a lesser effect in the gracilis muscle. This effect was likely secondary to the effects of IGF-1 on the muscle cells. The delivery approach used in this study resulted in an initial burst delivery of this factor, likely leading to a rapid diffusion of the factor from the site of the injection. A more sustained delivery of IGF-1 increases muscle regeneration.

Surprisingly, dual VEGF/IGF-I delivery from gels had a synergetic effect on the regenerative parameters in both of the analyzed muscles. In particular, both the mean fiber diameter and the number of centrally located nuclei in the fibers were significantly enhanced with alginate delivery of both GFs, showing a more pronounced response in the muscle where the gel was injected (gracilis). These results were qualitatively validated by an increased number of myoblasts found in an active proliferative state, the presence of myogenin positive cells, type IIC muscle fibers, and decreased cell apoptosis. These results demonstrate an enhancement in myoblast recruitment for neomuscle formation, which is consistent with the larger size and mass of these muscles. The enhanced myogenic regeneration in response to VEGF and VEGF/IGF sustained delivery could also be explained by the existence of a population of myoendothelial cells endowed with multilineage potential, including high muscle regenerative potential. Stimulation of angiogenesis may increase the pool of myogenic stem cells which are available to drive muscle regeneration. Furthermore, the combination of VEGF/IGF-1 was shown to alleviate ischemia with a return to normal hemodynamic levels and a better prevention of the necrosis associated with ischemia. Previous in vivo studies, using this same animal model, confirmed that the sustained delivery of bioactive growth factors (VEGF) from this gel system led to long-term (>15 days) elevated muscle levels. This contrasted with bolus delivery, as the factor concentration fell to undetectable levels within hours following that delivery approach. The sustained presence of factors enabled by alginate gel delivery correlated with the long-term alterations in the vascular and muscle tissue noted in the present study with gel delivery, as contrasted to bolus delivery.

As the peripheral nervous system is also affected by ischemic injury, the effects of sustained growth factor delivery on innervation at the neuromuscular junction (NMJ) was also examined. Ischemia is known to result in loss of NMJ innervation via degeneration of the presynaptic axon, and this was observed in the injury model used in this study. In the absence of growth factors, axons required two weeks to fully regenerate. In contrast, treatment with gels releasing either 1GF-1 alone, VEGF alone or IGF-1 and VEGF accelerated regeneration of damaged NMJs. IGF has been shown to have neuroprotective effects in mouse models of ALS, which is mediated by satellite cells and mature muscle fibers. Upregulation of IGF in these models also leads to a decrease in ubiquitin expression, suggesting that the mechanism of IGF neuroprotection may be inhibition of Wallerian degeneration. The reinnervation observed upon treatment with VEGF and IGF 1 suggests that gel delivery of factors is useful in treating the neurological complications of chronic ischemia. Together these effects played important roles in the early recovery of the mouse locomotive skills.

Most strikingly, tetanic force measurements of the tibialis and gracilis muscles demonstrated a significant increase to above normal levels with dual delivery of GFs versus the untreated (blank alginate) hindlimb, indicating functional muscle regeneration. In particular, an increase in force above normal (non-injured) muscle was noted at two weeks with these conditions, with a 2 and 8 fold increase in force for tibialis and gracilis, respectively, compared to the blank. Conversely, a significant decrease toward the normal value was observed, after 7 weeks, likely indicating an adaptation to normal physiologic requirements for these muscles. Increased muscle strength was also associated with a decrease in fibrotic tissues. Previous studies have shown a role of IGF-1 in finely modulating the balance between inflammation and regeneration, which is crucial for accelerating the functional recovery of injured muscle. After muscle injury, an inflammatory response is activated, but prolonged accumulation of fibrotic tissue limits muscle cell replacement, leading to less strength and functional depletion compared with normal muscles. The increased force observed in muscles with GFs delivery may also be related to enhanced reinnervation, although the specific mechanisms by which these GFs influence reinnervation remain to be defined.

In summary, the dual delivery of VEGF/IGF-1 from an injectable biodegradable hydrogel leads to a complete functional recovery of ischemic injured skeletal muscle. This strategy to enhance skeletal muscle regeneration represents a new therapeutic option for treatment of muscle damaged from a variety of causes. Additional factors which play roles in regulating the proliferation and differentiation of satellite cells and cells are optionally incorporated and delivered with this system.

Example 2

Activation of Transplanted Cells by Dual Delivery of VEGF and IGF-1 from a Macroporous Alginate Gel Leads to Regeneration of a Functional Muscle Prior to the invention, the two main existing strategies in cell therapy consisted of the direct injection of cells into the damaged tissue or their pre-culture and transplantation on scaffolds that serve as a template for neo-tissue formation. However, modulation of tissue regeneration subsequent to injury by cell transplantation requires the survival of donor cells and their stable incorporation into the host tissue. The improved strategy described herein involves the transplantation of progenitor cells on cell-instructive scaffolds designed to maintain cell viability, promote cell activation (proliferation) and outward migration from the scaffold in order to promote repopulation of the host damaged tissue and regeneration of the myotoxin-injured skeletal muscle ischemia. The goal was to direct the myogenic cells to bypass their normal tendency to differentiate and remain in a proliferative phase until a sufficient number of cells is attained to regenerate the tissue.

Dual delivery of VEGF with IGF-1 from macro-porous peptide-modified alginate scaffolds enhanced the engraftment of transplanted myogenic stem cells participating in subsequent rounds of injury repair, increased the proliferation of the satellite cells, limited fibrosis and, accelerated the regenerative process of injured skeletal muscle, resulting in increased muscle mass and most importantly, improved contractile function. Together, these results demonstrate the efficacy of finely controlled differentiated state of myogenic stem cell transplant for treating muscle degenerative disease. Design of Cell Therapy/Drug Delivery System for Muscle Generation In normal/healthy muscle, highly specialized myofibers, the basic contractile units of skeletal muscle, have the intrinsic ability to contract and generate movement. In injured muscles, the loss of myofibers' contractility can induce severe functional deficiency. Among others cell populations found to be implicated in muscle regeneration, such as muscle-resident side population (muSP) multipotent adult progenitor cells (MAPC) bone marrow-derived cells, the activation of the satellite cells, a quiescent specialized sub-population of adult stem cells localized within the basal lamina of the myofibers, is believed to be primarily responsible in the physiologic muscle-regenerative potential. So far, skeletal muscle regenerative efforts focused on cell therapies or (single/multiple) drug delivery strategies. However, on one side cell therapies, either the direct injection of cells into the injured tissues and engineered tissue transplantation, are limited by the massive death of the donor cells and by the poor integration of the out of shelf tissues with the host/recipient. In the other side the drug delivery strategies are limited by the rapidly depleted local concentrations of growth factors (GFs) and by the loss of bioactivity of the morphogens seriously impaired by the degradation occurring by the fast enzymatic cleavage which takes place when they are exposed to the in vivo environment. Furthermore, both these approaches were found to induce a slight improvement in tissue muscle regeneration.

Myoblast fate is finely regulated through biochemical and/or biomechanical microenvironmental signals including both extracellular matrix molecules and growth factors. To enhance transplanted myoblast survival and proliferation and regulate the extent of differentiation a arginine, glycine, aspartic acid (RGD)-containing cell adhesion ligands and macroporous alginate gels were used to encapsulate the cells and preserve/protect them from apoptosis Trophic factors regulate myoblast fate controlling the proliferation and differentiation of satellite cells. In vitro and in vivo studies have involved a number of factors, including both inflammatory cytokines, and growth factors, insulin growth factors acting as key modulatory role in muscle growth and regeneration. The release of single or multiple GFs (e.g. HGF, FGF-2, VEGF, IGF-1, PDGF-BB, etc) interspersed within natural or synthetic matrices (alginate PLG) occurs with a kinetics that is controlled by the physico-chemical properties of the scaffold material and therefore is finely tunable. In particular, the dual delivery of angiogenic (VEGF) and myogenic (IGF-1) factors from a biodegradable injectable alginate were found to promote skeletal muscle regeneration and induced a functional muscle regeneration of an ischemic musculoskeletal muscle. Efforts were undertaken to further improve the functional muscle recovery resulting from myotoxin-injured skeletal muscle ischemia by combining satellite cell transplantation and localized and sustained presentation of factors, i.e., those that modulate the angiogenesis (VEGF) and the myogenesis (IGF-1) processes.

The goal was to design a cell-instructive-scaffolds able to preserve exogenous progenitor cells from apoptosis and instead be activated and enter in the proliferative phase, migrate outward to the site of injury, fuse and differentiate in order to enhance repopulation of injured muscle from transplanted myoblasts and increase regeneration.

Donor myoblasts were obtained from transgenic Tg(ACT-bEGFP)1Osb, constitutively expressing GFP in all the cells and were seeded in scaffolds formed from arginine, glycine, aspartic acid (RGD)-presenting polymer, which also provide a sustained delivery of VEGF and IGF-1, and transplanted into genetically matched normal mice to determine the engraftment and hence the participation of host versus donor cells in regeneration. The delivery of cells on scaffolds that preserve myoblast viability and promote their activation and migration, led to a massive engraftment and long-term contribution of the transplanted cells on and in the host injured muscle tissue. The system was found to accelerate the regenerative process of a severely injured skeletal muscle, reduce degeneration, limit fibrosis, increase muscle mass, and overall lead to a striking improvement of muscle contraction function.

The following materials and methods were used to generate the data described in Example 2.

Alginate Modification and Scaffold Fabrication

Ultrapure alginates were purchased from ProNova Biomedical (Norway). MVG alginate, a high-G-containing alginate (M/G ratio of 40/60 as specified by the manufacturer) was used as the high molecular weight (250 000 Da) component to prepare gels. Low molecular weight (LMW) alginate (50 000 Da) was obtained by γ-irradiating high molecular weight alginate with a cobalt-60 source for 4 h at a γ-dose of 5.0 Mrad (Phoenix Lab, University of Michigan, Ann Arbor, Mich., USA). Both alginate polymers were diluted to 1% w/v in double-distilled $H_2O$, and 1% of the sugar residues in the polymer chains were oxidized with sodium periodate (Aldrich, St Louis, Mo., USA) by maintaining solutions in the dark for 17 h at room temperature. An equimolar amount of ethylene glycol (Fisher, Pittsburgh, Pa., USA) was added to stop the reaction, and the solution was subsequently dialyzed (MWCO 1000, Spectra/Por®) over 3 days. The solution was sterilized by filtration, lyophilized and stored at −20° C. Both alginates were modified with covalently conjugated oligopeptides with a sequence of $G_4RGDSP$ (Commonwealth Biotechnology, Richmond, Va.) at an average density of 3.4 mM peptide/mole of alginate monomer using carbodiimide chemistry as previously described. 2% irradiated alginate solutions were frozen and lyophilized until completely dry. Lyophilized alginate was added to MES buffer (Sigma-Aldrich, St. Louis, Mo.) to yield a 1% w/v solution, and EDC, Sulfo-NHS, and RGDSP peptide were added to the dissolved alginate and allowed to react for 20 h. The reaction was quenched with hydroxylamine, and the solution was dialyzed with decreasing concentrations of NaCl (7.5, 6.25, 5.0, 3.75, 2.5, 1.25, and 0%) over 3 days. The solution was purified via the addition of activated charcoal and subsequent sterile filtration. Sterile filtered alginate was frozen and lyophilized and stored at −20° C. The modified alginates were reconstituted in calcium-free DMEM (Invitrogen, Carlsbad, Calif.) to obtain 2% w/v solution (50% LMW/50% MVG used in all experiments) prior to gelation. Reconstituted alginate was stored at 4° C. To prepare gels, modified alginates were reconstituted in EBM-2 (Cambrex Corporation, Walkersville, Md., USA) to obtain a 2% w/v solution (50% LMW, 50% MVG used in all experiments) prior to gelation. The 2% w/v alginate solutions were cross-linked with aqueous slurries of a calcium sulphate solution (0.21 g $CaSO_4$/mL distilled $H_2O$) at a ratio of 25:1 (40 μl of $CaSO_4$ per 1 mL of 2% w/v alginate solution) using a 1-mL syringe. Alginates were first mixed with recombinant human VEGF165 protein (Biological Resources Branch of National Cancer Institute) and/or with recombinant human IGF-1 (R&D system) by using two syringes coupled by a syringe connector at a final concentration of 60 ug/mL for each protein. The calcium slurry (Sigma, St Louis, Mo., USA) was then mixed with the resulting alginate/growth factor/s solution using two syringes coupled by a syringe connector to facilitate the mixing process and prevent entrapment of air bubbles during mixing. The resulting solution was immediately expressed into the molds 2 mm depth. A sterile glass plate was placed over the mold and, after the alginate had completely gelled for 30 min, square of 5 mm×5 mm were cut using a punch.

To produce macro-porous scaffolds with open interconnected pores, the gels were cooled to −80° C., and the gels were lyophilized/freeze dried and stored at −20° C. until cell seeding. Fifty μl (200.000 cells/gel) of a cell suspension (4×10$^6$ cells/ml) was gently poured onto modified open-pore polymer scaffolds. The gel were incubated for about 20 min before adding a 500 μl of complete culture medium, then maintained at 4° C. prior to animal implantation.

Scaffold manufacture, porosity, and characteristics are further described in U.S. Ser. No. 11/638,796, U.S. Ser. No. 12/665,761, PCT/US2009/045856, PCT/US2009/000914, U.S. Ser. No. 61/168,909, and U.S. Ser. No. 61/281,663, hereby incorporated by reference.

Myoblast Purification, Characterization and Cultures

Primary myoblasts were derived from 4-12 weeks-old wt C57BL/6 and transgenic Tg(ACTbEGFP)1Osb, constitutively expressing GFP in all the cells, mice skeletal musculature. After the sacrifice, the satellite cells were isolated from hindlimbs using standard methods. Under sterile conditions, hindlimb skeletal musculature was surgically excised, finely minced, and disassociated in 0.02% Trypsin (Gibco/Invitrogen) and 2% collagenase type 4 (Worthington Biochemical, Lakewood, N.J.) for 60 min at 37° C./5% CO$_2$ while agitating on an orbital shaker. Disassociated cells were strained through a 70 μm sieve, centrifuged at 1600 rpm (Eppendorf 5810R) for 5 min, and re-suspended in high-glucose DMEM, with added pyruvate (Gibco). The medium was further supplemented with 10% fetal bovine serum (FBS) and 10% penicillin/streptomycin (P/S, Gibco) and this was used in all cell culture studies (for both primary and cell line). Cells were plated and cultured at 37° C./5% CO$_2$ for 72 h before media change. After 72 h in culture, the media were changed every 48 h until cells were 80% confluent (about 7 days). Cells were collected via centrifugation and purified via Percoll (Amersham Biosciences, Uppsala, Sweden) fractionation. To characterize Percoll purified primary myoblast cultures, myogenic differentiation was assessed by staining with desmin (1/100; Santa Cruz Biotechnology, Santa Cruz, Calif.).

For clinical applications, as few as 10,000 cells, 1×10$^4$, 1×10$^5$, 1×10$^6$, 1×10$^7$ or 1×10$^8$ cells are used to seed a delivery scaffold. Sources and methods of obtaining myogenic cells for seeding are further described in Saverio et al., 2010, J. Clin. Invest. 120:11-19; hereby incorporated by reference.

Animals and Tissue Injury

GFP transgenic mice (C57BL/6-Tg(ACTbEGFP)1Osb) were used only as a cell source, conversely six-seven weeks-old female wt C57BL/6J mice (Jackson Laboratories, Bar Harbor, Me., USA), were used for treatments. Mice were anesthetized with an intraperitoneal injection of a mixture of ketamine 80 mg/kg and xylazine 5 mg/kg prior to all surgical procedures. For myotoxin injuries, the tibialis anterior muscles (TA) of the right legs of anesthetized mice were injected with 10 ul of 10 ug/ml Notexin Np myotoxin from *Notechis Scutatus* snake venom (Latexan) using a 5 ul Hamilton syringe. After 6 days from notexin injection, hindlimb ischemia was induced by unilateral external iliac and femoral artery and vein ligation. After the vessel ligation, the middle part of tibialis muscle was treated. The incision was surgically closed, and animals monitored over time.

Ischemia and Perfusion

Measurements of the ischemic/normal limb blood flow ratio were performed on anesthetized animals (n=10) using a LDPI analyzer (Perimed AB, Stockholm, Sweden). Perfusion measurements were obtained by scanning entire hindlimbs under basal conditions and then weekly after surgery, and the ratio of perfusion between ischemic to non-ischemic limb of the same animal was calculated.

Histological Assessment of Skeletal Muscle

At 3 days, 2 weeks and 6 weeks following induction of ischemic injury, anesthetized mice were sacrificed and hindlimb muscle tissues (n=10 per time point per experimental condition) were processed for histological analyses. For regeneration metrics, the samples were stained with hematoxylin and eosin. Images were captured at 20× magnification and merged in Adobe Photoshop (Adobe systems, San Jose, Calif.) and then the number of centrally located nuclei was manually measured and tallied. Vascular ECs were identified by immunostaining for mouse CD31 (BD Biosciences Pharmingen, San Diego, Calif., USA). For measurement of capillary densities, histological analysis was performed in a blinded fashion. All the merged tissue sections were randomly analyzed. The number of positively stained blood vessels was manually counted and normalized to the tissue area. Sections from each sample were visualized at 200 and 400 with an Olympus IX81 light microscope (Japan) connected to an Olympus DP70 digital image capture system (Japan), and analyzed using IPLab 3.7 software (Scanalytics, Rockville, Md., USA).

GFP expression was detected in both muscle cryo-section and paraffin-section of cells engrafted muscles respectively by direct GFP fluorescence and by anti-GFP immunofluorescence. In particular, muscle paraffin-sections were permeabilized with 1% BSA-0.2% Triton X100/PBS and 5% goat serum, and stained with 1:50 chicken anti-GFP (Molecular Probes) and, 1:200, 488 goat Alexa Fluor anti chicken (Molecular Probes). Interstitial fibrosis was morphometrically assessed in Masson Trichrome (Sigma Aldrich) stained sections.

Mechanical Measurements

At 3 days, 2 and 6 weeks following the treatment, C57BJ6 mice (n=5/conditions) were anesthetized before muscle isolation and then sacrificed by cervical dislocation. Intact Tibialis (T) muscles for each conditions (blank alginate, alginate+VEGF$_{165}$/IGF-1, alginate+VEGF$_{165}$/IGF-1 and cells, bolus of VEGF$_{165}$/IGF-1 and cells) and the uninjured controlateral hindlimb were dissected for isolated muscle force measurements. The muscle was mounted vertically midway between two fine cylindrical parallel steel wire electrodes (1.6-mm diameter, 21 mm long), attached by its tendons to microclips connected to a force transducer (FORT 25, WPII, Sarasota, Fla., USA) and bathed in a physiological saline solution (in mM: 122.2 NaCl, 2.8 KCl, 1.2 KH$_2$PO$_4$, 25 NaHCO$_3$, 1.2 MgSO$_4$, 1.3 CaCl$_2$, and 5 D-glucose in a chamber oxygenated with 95% O$_2$-5% CO$_2$. The experimental temperature (monitored in the bathing solution) was maintained at 25° C. The experimental protocol involved adjustment of muscle length until maximum twitch force was achieved (100-300 Hz). A wave pulse was initiated from a computer using a custom-written LabVIEW program and delivered to the stimulation electrodes via a purpose-built power amplifier (QSC USA 1310). A switch on the amplifier permitted stimulation via wire electrodes. Contractions were continuously monitored on a LabView chart recorder, and contractions saved on a PC. Contractions were evoked every 5 min.

Tetani were usually evoked at 300 Hz-15-20 V with constant pulse width and train duration of 2 ms and 1 s, respectively. These stimulation frequencies and voltages were required to generate maximum force but exceed the naturally occurring median firing frequencies of 100-200 Hz in Tibialis. After force measurements were completed the muscle were removed from the bath and weighed. Peak tetanic force was determined as the difference between the maximum force during a contraction and the baseline level, and specific force calculated based on muscle weight.

Statistical Analyses

All results are expressed as mean±standard deviation (SD). Multivariate repeated-measures ANOVA was performed to test for interaction between conditions. Differences between conditions were considered significant if p value<0.05.

Enhancement of Skeletal Muscle Stem Cell Engraftment by Dual Delivery of VEGF and IGF-1 from a Cell-Adhesive Macroporous Alginate Gel In this study, tibialis muscle of each recipient C57BJ6 mouse was preinjured by intramuscular injection of notexin six day prior the transplantation in order to enhance the muscle regenerative response After 6 days, when presynaptic activity, blocking the release of acetylcholine, and the myotoxin effects exerted from Notexin Np injection was markedly diffused into the middle part of tibialis muscle, mice had undergone unilateral external iliac and femoral artery and vein ligation to induce a more severe hindlimb ischemia and treated. Analysis of the tissue sections at early time revealed a largely necrotic defect with diffusely disorganized and disrupted/broken myofibers in all the conditions analysed (FIG. 1 c-d). The combination of Notexin injection and ischemia injury was selected as the most severe injury model, comparing the recovery of the mechanical functionality of the tibialis muscles at 2 weeks between muscles subjected to different type of injuries, including partial laceration, cryoinjury, notexin injection alone or the previous combined with the femoral artery and vein ligation. At the time of vessel ligation the middle part of the tibialis muscle was treated. A macroporous, degradable RGD-modified alginate gel with open, interconnected pores was designed to deliver growth factors and/or GFP-primary myoblasts.

In particular, one of the following four treatments were used to heal the injury: (i) blank macroporous alginate vehicle, (ii) alginate vehicle delivering VEGF (3 μg) and IGF-1 (3 μg), (iii) alginate gel delivering VEGF and IGF-1 (3 μg each) and GFP-satellite cells (200.000 cells/gel) and, (iv) bolus of GFP-satellite cells (200.000 cells/gel) and VEGF and IGF-1 (3 μg each) in PBS. Even though no suture points, adhesive or glue were used to maintain the scaffold at the site of implantation, at the time of retrieval (3 days, 2 and, 6 weeks) the scaffolds were still localized where it was implanted initially (FIG. 1-b). A complete loss of locomotion of the injured hindlimb was immediately observed in all the condition analysed (FIG. 1-e).

Figure 2:
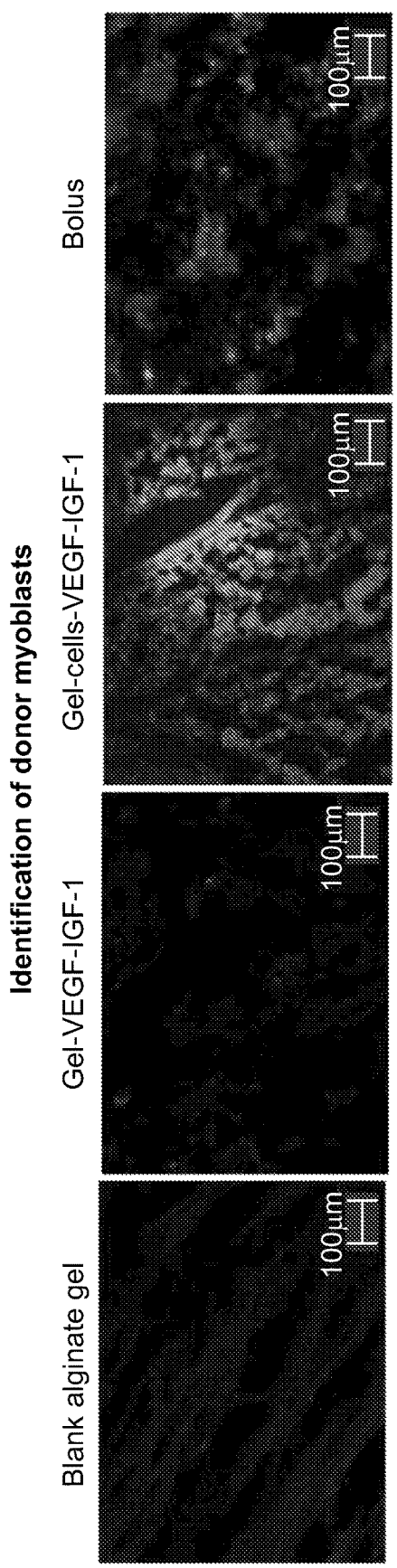
FIG. 2 is a series of photomicrographs showing identification of donor myoblasts engraftment. Representative images showing GFP expression (green) by immunofluorescence on transverse sections of muscle harvested 6 weeks after transplantation and treatment.

The capacity of donor GFP-primary myoblasts to engraft in diseased muscle and to act as a regenerative precursor population to repair muscle, was first analysed. Engraftment of donor-derived myofibers in recipients was measured by direct epifluorescence for GFP on transverse and longitudinal sections of muscle harvested at 6 weeks after transplant. However, GFP detection by epifluorescence also was confirmed by immunofluorescence (FIG. 2). Analyses of transplanted tibialis muscles of recipient mice revealed a robust engraftment of donor-GFP myoblasts into the host regenerating muscle when cells were transplanted on scaffolds releasing VEGF/IGF-1 (FIG. 2). A more limited number of engrafted donor cells was found in the conditions by using direct myoblast bolus injection with GFs. No cells were noted in the other experimental treatment (alginate gel VEGF/IGF-1) and control conditions (blank alginate gel).

Furthermore, a significantly larger skeletal muscle mass was noted at 3 days in injured muscles treated with alginate gel containing/delivering both satellite cells and growth factors when compared with the blank alginate gel at the same time (FIG. 3 B). Quantification of the weight of these muscles confirmed a pronounced changes with alginate releasing either cells and VEGF/IGF-1, or VEGF/IGF-1 treatment with a statistically significant increases of 28.5% and 20.4% (FIG. 3 A) respectively, compared with blank alginate gel at early time (3 days) with the tendency to decrease gradually with time (showing respectively an increase of 22.7% and 1.2% at 2 weeks and 23% and 3.1% at 6 weeks). To directly analyze muscle regeneration, the number of postmitotic centrally located nuclei per length of myofiber in the resolving muscle tissue were quantified as index of newly regenerated myofibers (FIG. 4 A). At early time post-injury (3 days) the tibialis muscle fibers in the injury group treated with VEGF and IGF-1 without cell showed an approximately 60-50% increase in centrally located nuclei as compared with the blank and bolus factors delivery. The two factors in combination with cells alginate delivery led to a 78% and a 45% increase in centrally located nuclei per 100 um fiber length, as compared with the blank alginate or with alginate delivering GFs (FIG. 4 A). At 6 weeks post-injury the tibialis muscle fibers treated with alginate delivering cells and VEGF/IGF-1 showed an approximately 2.5 fold-increase in centrally located nuclei, while co-delivery of both GFs without cells led to a 1.27 fold increase in the number of centrally located nuclei, compared to the blank alginate gel, and a 3.1 fold increase compared to the bolus treatment (FIG. 4 A).

Representative cross and longitudinal microsections of tibialis tissue at postoperative 3 days and 6 weeks (FIG. 4 B), stained with H&E highlight the increase in centrally located myonuclei in the injured muscles treated with alginate delivering cells and VEGF//IGF-1. In mice treated with gels delivering cells and growth factors, multiple centrally located nuclei were observed in tissue cross sections under high power magnification. The capability of donor GFP-primary myoblasts transplantation to improve blood vessel density and hemodynamic recovery (the perfusion of ischemic injured tissues) was next analyzed. Immunohistochemical analysis was carried out on tibialis tissue sections for the presence of the endothelial marker CD31 (FIG. 5 A) at early time (3 days) and at the late time (6 weeks) post-treatment. In particular, at 3 days, it revealed that VEGF/IGF-1-delivering alginate gels (FIG. 5 A) increased muscle blood vessel densities of 1.4 fold and 1.2 fold, as compared respectively with injection of a blank vehicle or bolus delivery of cells and VEGF/IGF. At 6 weeks, VEGF/IGF-1 delivery from the gels resulted in an approximately 1.9 fold and 1.5 fold increase in vessel density in tibialis muscle as compared to the ischemic hindlimb treated with the blank alginate and bolus injection (FIG. 5A). Quantification revealed that gels delivering both myoblasts and GFs induce an even greater increase in blood vessel density leading to a 1.4-fold and 1.2-fold increase compared to gels delivering only growth factors respectively at 3 days and 6 weeks post treatment. Conversely, bolus delivery of cells and VEGF/IGF had no significant effect on vascularization and a modest effect is observed at early time as compared to the control (FIG. 5 A). Representative images of all the merged tissue sections at 6 weeks post-treatment are shown in FIG. 5 B.

A Laser Doppler Perfusion Imaging (LDPI) system was used to quantify perfusion of the hindlimbs (FIG. 6 A-B). Images indicate improved hemodynamic recovery of mice transplanted with alginate gel delivering both cells and GFs (FIG. 6 A). The GFs delivery alone produced a milder improvement of the clinical outcome. In particular quantification of the ischemic/non ischemic perfusion ratio (FIG. 6 B) revealed, after an expected 20% reduction of the blood flow immediately after surgery in all the conditions analysed, a slow increase in reperfusion in mice treated with blank alginate gel and bolus of cells and VEGF/IGF over time. In contrast, dual VEGF/IGF delivery from the alginate gel led to a gradually increase in tissue perfusion over time with a final recovery of 75% of normal limbs at 6 weeks. Interestingly, animals treated with alginate gels delivering both myoblasts and VEGF/IGF-1 showed a marked increase in blood flow starting from the first week after the injury with a 78.6%, and reaching a 99% recovery at 5 weeks compared respectively with 64.9% recovery induced by gel delivering VEGF/IGF-1 (FIG. 6 B).

To test whether muscle changes induced by GFs delivery and engraftment/incorporation by satellite cells might correspond to increased function and hence have a therapeutic benefit, the contractile force of the muscles was measured. The weight normalized tetanic force of the anterior tibialis (FIG. 7 A) were measured after maximal tetanic stimulation. At 3 days postsurgery, all the muscle treatments induced about 1.2 fold loss of the contractile force compared with the uninjured control. At 2 weeks postsurgery, muscles treated with alginate gel delivering VEGF/IGF-1 showed a significant increase above normal values in the tetanic force (1.2 fold and 3.2 fold increase, respectively when compared with the control and the blank alginate). A similar trend was observed in animals receiving bolus treatment. A more pronounced effect was measured with alginate gel delivering both satellite cells and VEGF/IGF-1 (2 fold and 1.6 increase respectively when compared with the control and the alginate gel delivering VEGF/IGF-1). However, a decrease toward the normal value was observed only in animals treated with alginate gel delivering satellite cells and VEGF/IGF-1 at 6 wks postsurgery. In fact, animals receiving alginate delivering only VEGF/IGF-1 or bolus treated showed a similar trend, but the decrease in the contractile function was markedly more pronounced.

Along with reduced recovery of the functional contractile properties, a large content of fibrotic tissue was formed, as imaged by Masson's trichrome staining (FIG. 7 B), in injured muscle tissue treated with either blank alginate and bolus injection over time, while control uninjured hindlimbs demonstrated little fibrotic tissue, as expected. Conversely, limbs treated with alginate gel delivering GFs alone and alginate gel delivering both myoblasts and VEGF/IGF-1 exhibited a significant decrease in fibrosis.

The strategy described herein involves the transplantation of satellite cells on scaffolds appropriately designed to maintain the viability of donor cells, promote their activation and their afterward cell spreading and migration outside the scaffold and their stable incorporation into the host tissue. This approach showed to be effective in inducing both a repopulation of the host damaged tissue and an enhancement of muscle repair.

Compared with standard approaches (cell therapy and drug delivery), the scaffold does not serve as a tissue template, but it has to mimic special tissue environment biochemical cues immediately surrounding (the precursor/progenitor) cells, so called "stem cell niche". The device comprising cells and at least 2 factors (VEGF and IGF, in this case) effectively mimics a naturally-occurring stem cell niche. The niche is fundamental in controlling the stem cell behavior, in particular, the quiescence, self-renewal and cell fate commitment state of the implanted stem cells. The viability and the ability of myoblasts to migrate from vehicles are strongly regulated by four main factors, consisting of the presentation of adhesion ligands by the material vehicle, the material biodegradation, the pore structure/size and the release kinetics of growth factors from the vehicle material.

Covalent modification of alginate with the adhesion oligopeptides $G_4RGDSP$ prior to scaffold fabrication, compared with scaffold lacking cell adhesion ligands, was demonstrated diffusively to allow a controlled presentation of signals that promote and regulate cell adhesion to this polymer, and hence the viability and the proliferation of the primary myoblasts. In addition, the feasibility to control the molecular weight distribution of the polymer used to form gels allows to regulate gel degradation, the pore size (nano, micro, macro-pores) and the architectural structure (interconnected, aligned . . . ) of the polymer and hence, to modulate the viability of alginate encapsulated cells as well as their outward migration. In particular, as compared to nano- and micro-porous (10-20 µm pores) peptide modified scaffolds, myoblasts seeded in macroporous (~200-400 µm) peptide modified scaffolds was demonstrated to improve both the viability and outward migration. Similar results were observed for smooth muscle cells, e.g., better proliferation on macroporous scaffolds. The incorporation of soluble factors significantly influences the proliferative/differentiation state of the transplanted myoblasts. The dual delivery of the pro-angiogenic regulator VEGF and the key regulator of satellite cells activation and differentiation IGF-1 (VEGF/IGF-1 alginate gel) from an alginate gel was investigated in both in vitro and in vivo (Example 1). The combination of these two factors was demonstrated to enhance functional contractile skeletal muscle regeneration, revascularization and re-innervation of muscle tissue. In contrast to other combinations tested (e.g., FGF-2, HGF), the VEGF/IGF combination was found to not only promote muscle regeneration but also to profoundly improve the contractile activity of the skeletal muscle. This surprising and significant advantage is due to the synergic effect exerted by both VEGF and IGF-1 on reinnervation.

These data indicate that controlled spatio-temporal release of the two critical morphogens, $VEGF_{165}$ and IGF-1, from a macroporous RGD-modified alginate gel coupled with the transplantation of donor satellite cells induce surprising and remarkably more efficient functional muscle regeneration compared to any other known method. This effect was demonstrated using a severe ablating muscle injury model (myotoxin-ischemia induced skeletal muscle injury). The results of this study indicate that localized delivery of VEGF and IGF-1 from a macroporous scaffold into injured myotoxin-ischemic muscles significantly enhances muscle regeneration compared with the blank alginate treatment (FIGS. 3A-4B). These data confirm and extend findings showing a therapeutic benefit of the combined delivery of VEGF/IGF-1 from a alginate gel on the overall muscle regeneration process (Example 1).

Figure 3B:
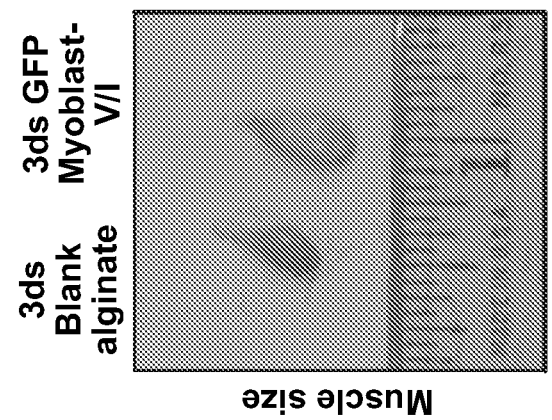
FIGS. 3A-B are a bar graph and photograph showing muscle weight and size, respectively.
Figure 3A:
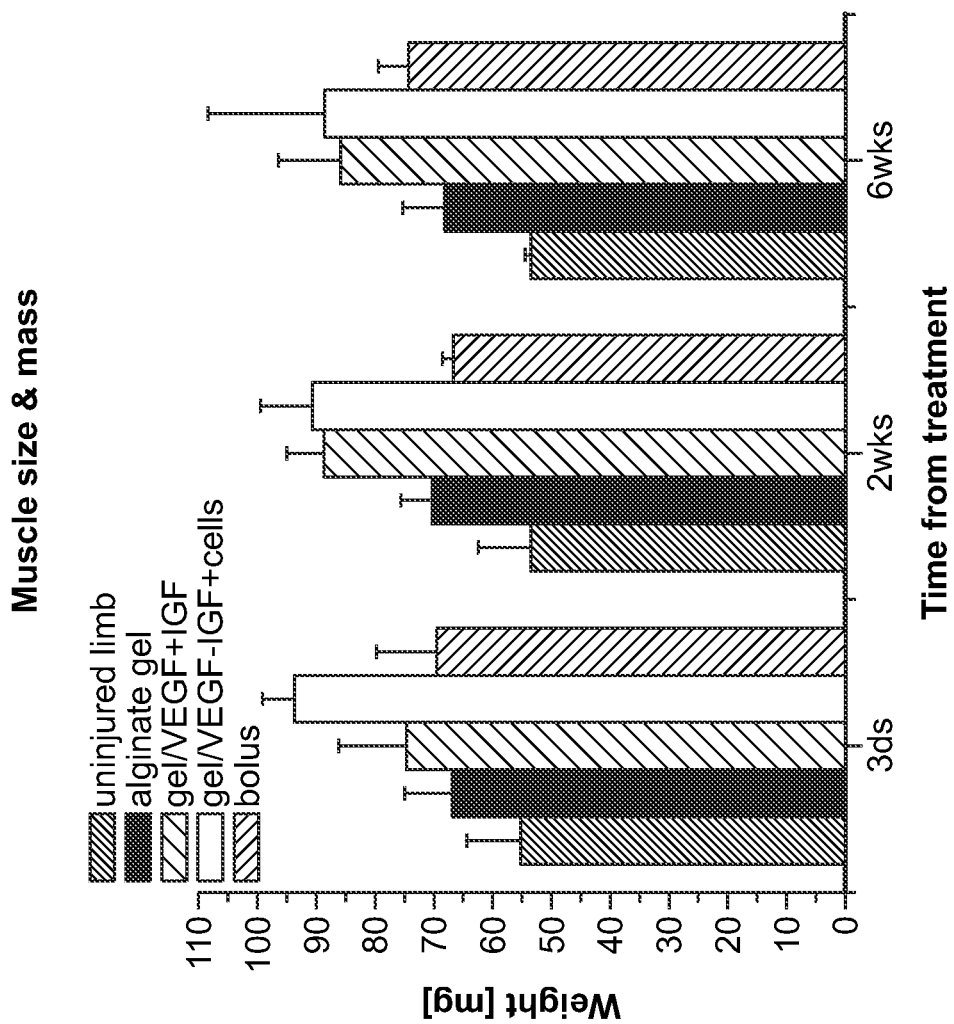

Transplanting the cells with a scaffold that simultaneously delivers VEGF/IGF-1 dramatically enhanced the participation of transplanted cells in muscle regeneration (FIG. 2), promoting both cell viability and migration out of the scaffold in the surrounding injured tissue. The robust transplanted cell engraftment was maintained for extended period of time following the time of treatment in mice (6 weeks). This capacity of enduring in time indicated that the beneficial effect exerted by the dual delivery of the GFs creates an appropriate microenvironmental niche for a long-living progeny able to induce a lasting muscle regeneration process. Conversely, the direct bolus injection of primary satellite cells and GFs induced a significant lesser amount of transplanted cells engrafted in the host muscle; this effect was likely due to both the modality of delivery leading to a rapid lost of the GFs' bioactivity on one side and, to a massive death of the donor cells deprived of the adhesive initial polymeric support to the other side. The enhancement in satellite cells engraftment in the repair of severe ablative muscle injury is accompanied by a higher recruitment of activated myoblasts as shown by the quantitatively greater density of the centrally located nuclei per length of myofibers in muscle treated with scaffold delivering cells and growth factors. This result is also validated/consistent with the increase in size and weight of these muscle as compared with injured muscle treated with black alginate and bolus injection from early time (FIGS. 3A and 3B). A lesser increase in muscle regeneration parameters was observed with the implantation of alginate delivering only GFs, but still detectable as compared with blank alginate or bolus treatments.

The analysis of muscle injury section treated with localized sustained delivery of GFs and cells revealed a better resolved defect area at early time (FIG. 4 B) as compared with all the other conditions where the larger injured area were characterized by profoundly disorganized and necrotic myofibers at the same time point. The data indicate that the methods lead to a faster, more efficient, and more effective regenerative process due to a contribution of satellite cells both by fusion with existing host myofibers and/or by de novo myogenesis as a result of the microenvironment created by the device and the presence and tuned release of VEGF and IGF in concert. The synergistic effect was demonstrated by a clinically relevant outcome of markedly earlier recovery of the motility (walking ability) of the injured hindlimb.

In addition to an improved and early effect on myogenesis, the transplantation of cells from scaffolds delivering GFs promoted pronounced angiogenesis and the return to the normal level tissue perfusion as compared with all the other conditions, likely activating pathways controlling the endogenous activity of these cells. However, a slower but still significant pro-angiogenic effect was quantified (FIG. 5 A) in muscle injured treated with alginate gel delivering GFs at late time from treatment as observed in FIG. 5 B. Conversely, a modest increment in blood vessel density was induced by blank alginate gel and bolus treatments.

Finally, the dual delivery of satellite cells and GFs from macroporous alginate gel reduced muscle inflammation and fibrosis (FIG. 7 B) and more importantly, improved strongly the muscle contractile function (FIG. 7 A). This result is related with the synergic effect played by IGF-1 in modulating inflammation and regeneration processes and in part with the proangiogenic and neuro-protective effect of VEGF. After a 2.2 fold (54.32%) loss of muscle strength immediately after the injury, a significant increase of the muscle strength, above the normal level, was observed after 2 weeks from the treatment, followed by a decrease around the normal value at 6 week post-treatment. This trend is likely associated to the two main phases of activation/proliferation and late differentiation of the myoblasts participating to the muscle regeneration process. These effects were consistent with the modest increase in the fibrotic tissue (FIG. 7 B). Conversely, the delivery of a combination of VEGF and IGF-1 from scaffolds, in the absence of transplanted cells, had a less pronounced effect on muscle regeneration.

The results provided startling evidence for the feasibility of stem cell niches molecular mimicry in vivo and in a accepted and clinically relevant animal model. In fact, the devices and methods described herein demonstrate that the use of cell-instructive scaffolds simultaneously function as a vehicle and a reservoir of progenitor cells and growth factors. The myogenic response in vivo and the transplanted cell fate was effectively modulated by the synergic cooperation between structural ECM components associated with angiogenic and myogenic growth factors.

Example 3

Muscle Regeneration and Revascularization in Aging Subjects

In young subjects, a nominal level of muscle regeneration/revascularization occurs after injury or disease to the tissue. As is discussed above, delivery of VEGF and IGF in a hydrogel matrix significantly enhances the regenerative effect. However in older individuals, the naturally-occurring regenerative response to injury/disease is greatly reduced or absent. In humans, the total lean body mass (LBM) declines by about 18% in men and by 27% in women from the second to eighth decade of life; the decline in LBM becomes detectable after the age of 45 years, and also reflects a loss of regenerative capacity. Thus, the VEGF/IGF devices and delivery methods are particularly useful for treatment of such individuals.

Figure 8:
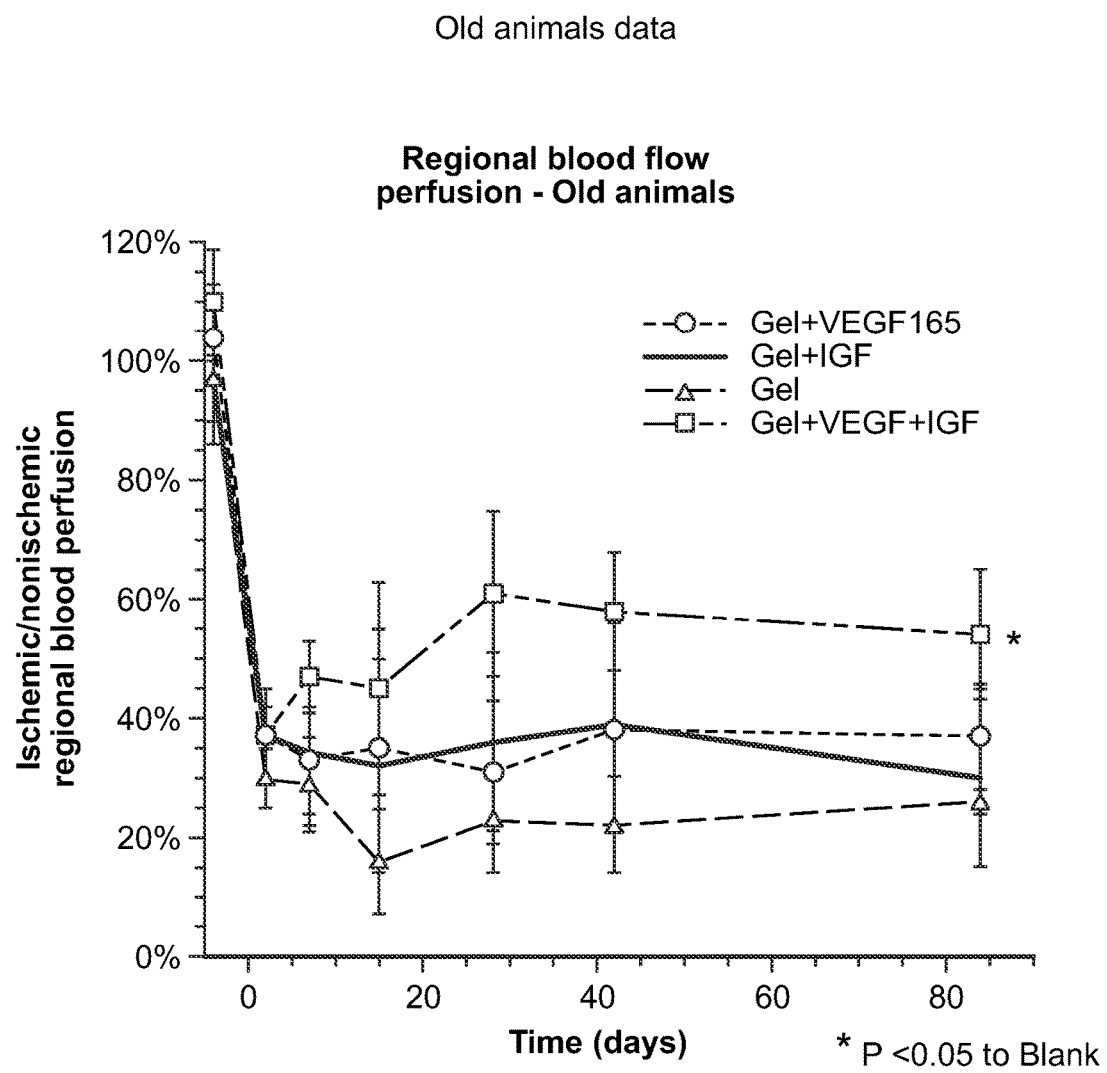
FIG. 8 is a line graph showing regional blood flow following gel delivery of VEGF and/or IGF.

Studies were undertaken to evaluate the effect of hydrogel VEGF/IGF delivery to muscle tissue in young animals as compared to old animals. Preparation and delivery of growth-factor loaded hydrogels was carried out as described above. Rather than using young mice (e.g., 6-8 weeks of age), old mice (approximately 2 years of age) were tested. FIG. 8 shows regional blood perfusion of the hindlimb (ischemic vs nonischemic limb) of old mice. C57BL/6J old animals (>2 years old) displayed little to no spontaneous recover (gel), in terms of hemodynamic flow analysis, which contrasts to the situation in young mice. Mice treated with gel delivery of $VEGF_{165}$ or IGF alone showed a low level of recovery, while gel delivery of both VEGF and IGF alone led to a much greater level of recovery. For example, the enhancement in perfusion with delivery of IGF and VEGF is greater than 3-fold, as compared to untreated subjects.

Figure 9:
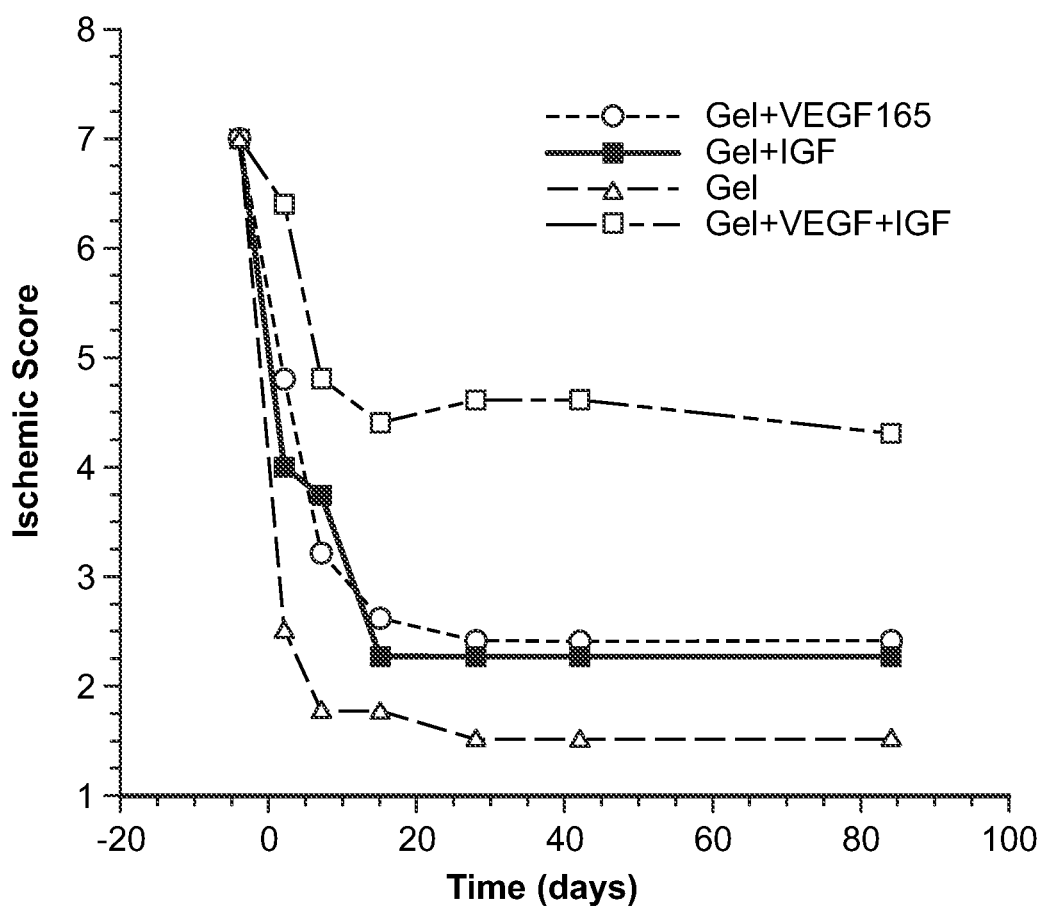
FIG. 9 is a line graph showing ischemic grade/score following gel delivery of VEGF and/or IGF.
Figure 10:
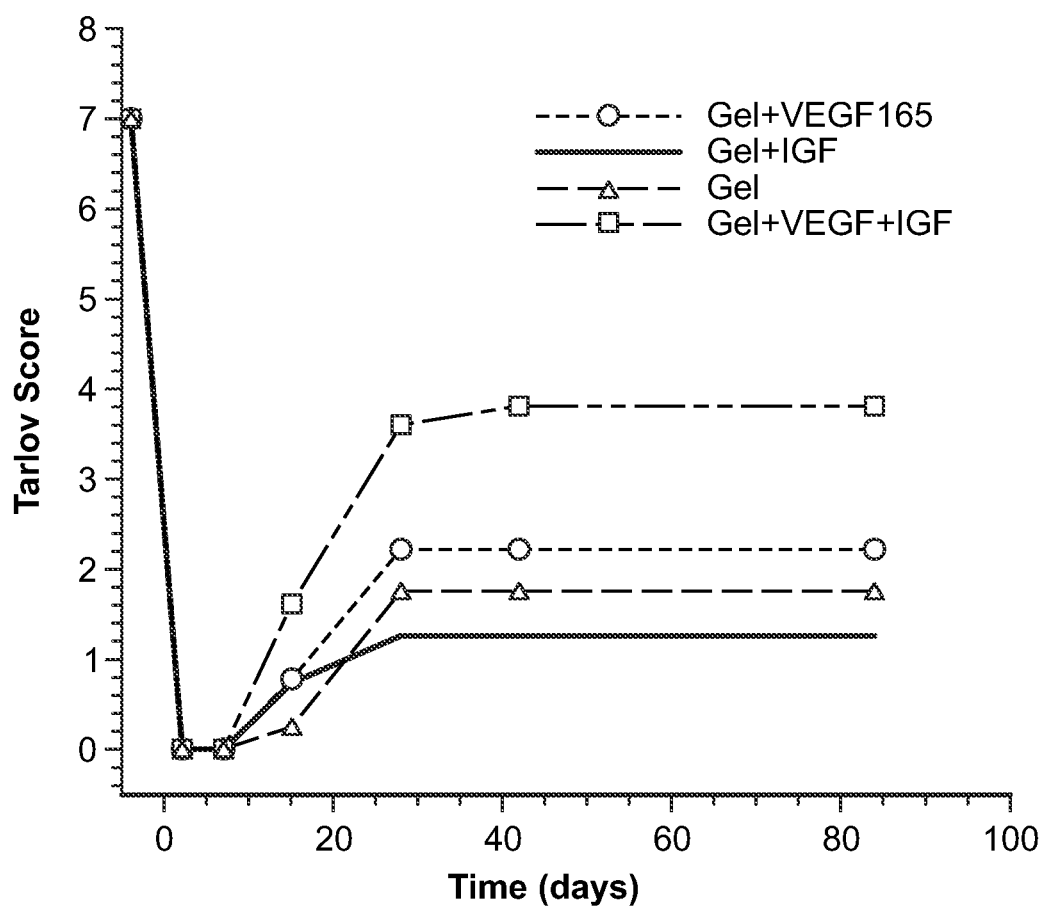
FIG. 10 is a bar graph showing the ability of animals to locomote and bear body weight following gel delivery of VEGF and/or IGF.
Figure 11:
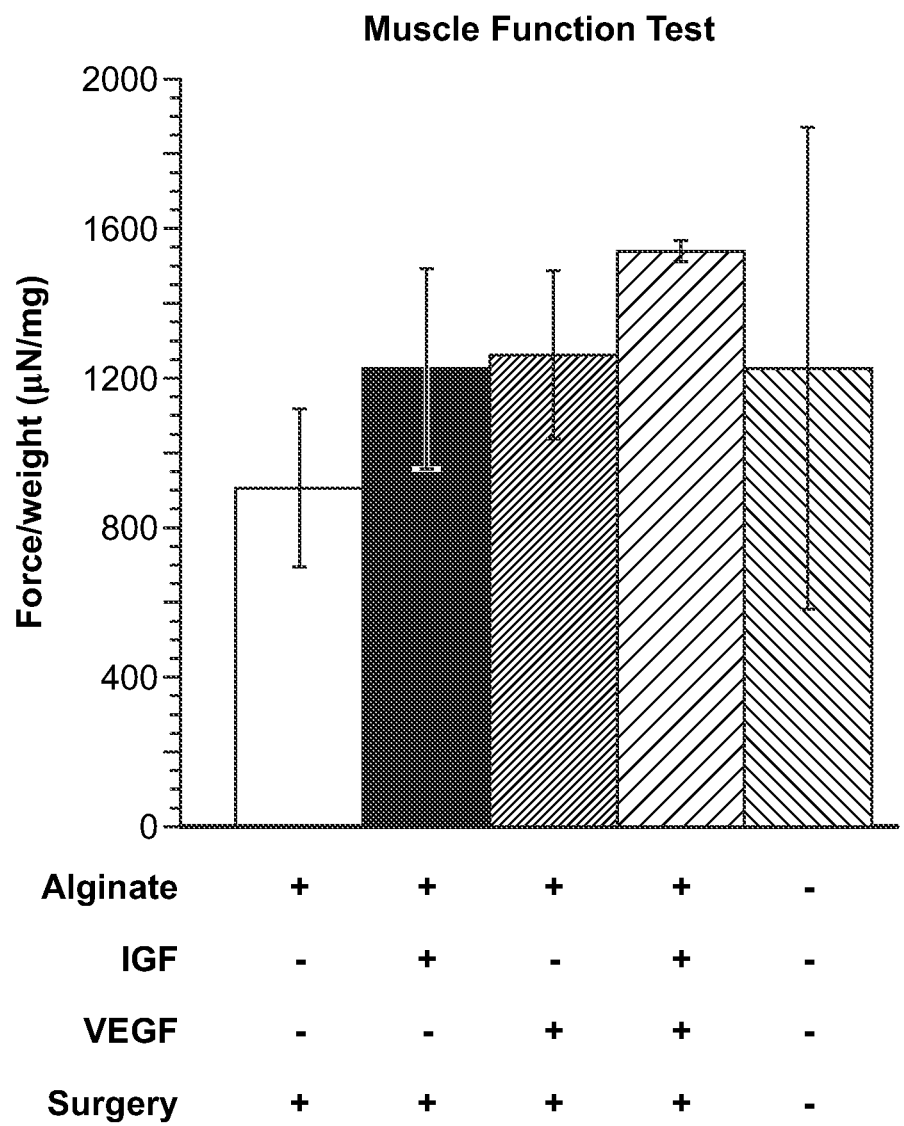
FIG. 11 is a bar graph showing the results of a muscle function test following gel delivery of VEGF and/or IGF.

A distribution and level of ischemic severity displayed in the old animals is shown in FIG. 9. The ischemic grade used the following score: 0—autoamputation of leg; 1—leg necrosis; 2—foot necrosis; 3—two or more toe discoloration; 4—one toe discoloration; 5—two or more nail discoloration; 6—One nail discoloration; 7—No necrosis. The results indicated that gel delivery of VEGF and IGF together led to a much less ischemic injury than the factors alone, or control (gel with no factors).

In addition to evaluation of blood perfusion and ischemic severity, the functionality of the treated muscle tissue was determined. The Tarlov score is a functional test that directly evaluates the ability of animals to locomote and to bear their body weight via the inferior limbs. The Tarlov grade use the following score: 0—No movement; 1—Barely perceptible movement, no weight bearing; 2—frequent and vigorous movement, no weight bearing; 3—supports weight, may take 1 or 2 steps; 4—walks with only mild deficit; 5—normal but slow walking; 6—full and fast walking. Gel delivery of VEGF and IGF together led to a significant improvement (at least 1 and up to 2-3 units in Tarlov grade) in hindlimb function. Muscle function of hindlimbs of old animals was also evaluated using a force generation test at 12 weeks after surgery and polymeric vehicle treatment. The force generation (normalized to muscle mass) was measured by dissecting the muscle from the mice at the 12 week time point. Gel delivery of VEGF and IGF was found to lead to a significantly higher level of muscle regeneration and function, as compared to injured, control muscles treated with blank gel. Control, non-ischemic muscles are shown for comparison.

These surprising results indicate that co-delivery of VEGF and IGF to injured or diseased muscles is particularly efficacious for treatment to regenerate muscle tissue of aged individuals.

Example 4

Minimally Invasive Repair of Injured Skeletal Muscle with Biodegradable Scaffolds The repair of damaged skeletal muscle may be enhanced by the injection of muscle stem cells and/or recombinant growth factors, but is currently limited by inefficient methods for their delivery. A degradable covalently cross-linked alginate scaffold was developed for delivery of progenitor muscle cells and growth factors to treat skeletal muscle injuries. This scaffold was highly porous and compressible, returning to its original shape when rehydrated (i.e., the scaffold is characterized as having "shape memory"). This composition allowed minimally invasive implantation of the scaffold via a catheter and, since the scaffold is degradable, there was no need for invasive follow-up surgery to remove the implant once its repair function was completed.

The shape-memory alginate hydrogels are covalently crosslinked and oxidized (to induce biodegradability). They are dry and porous. Following lyophillization and compression, the material is pliable (not brittle), e.g., it can be rolled up and put into a syringe/needle assembly or angiocatheter (e.g., 10-14 gauge) for in vivo delivery to the body. Once place in a desired location in the body, a syringe/needle assembly or catheter is used to subsequently deliver a cell suspension to the shape-memory device. Because the device is hydrophilic, it then soaks up the cells. The cells are then slowly released from the device and migrate out of the device to bodily tissues.

Cultured muscle progenitor cells delivered alone (i.e., in the absence of the hydrogel matrix/scaffold) are characterized by poor survival and little or no proliferation postdelivery in vivo. In contrast, muscle progenitor cells delivered within the scaffold survived for several weeks (3-4 weeks and longer), proliferated, and demonstrated active migration from the scaffold (i.e., out of the scaffold and into muscle tissue of the treated subject). The alginate scaffold was also capable of prolonged growth factor release.

A severe muscle injury model was used to test the ability of the growth factor-containing hydrogel scaffold to enhance the muscle repair process. The scaffold was used to deliver combinations of different treatments including primary murine muscle cells, IGF-1 and/or VEGF.

The implanted scaffolds delivering cells and IGF-1 enhanced cell survival and migration into the damaged muscle site compared to cells and IGF-1 injected without scaffolds, resulting in increased fusion of the injected cells with the regenerating host muscle fibers. The addition of VEGF to the scaffold promoted angiogenesis in the damaged muscle tissue, contributing to muscle repair. The combined delivery of VEGF and IGF-1 from the scaffold led to a significant reduction in fibrotic tissue and an increase in muscle contractile function compared to their delivery without a scaffold. The implanted scaffold did not stimulate an inflammatory response. Thus, the shape-memory alginate scaffold is useful as a synthetic matrix for use in a tissue repair to improve the restoration of the structure and function of severely injured skeletal muscle.

The 3-D degradable scaffold is highly compressible for in vivo delivery by catheter yet returns to its original shape in vivo (i.e. shape-memory characteristics), with the ability to deliver growth factors and muscle precursor cells in vivo for skeletal muscle repair. Transplanted cells in resorbable three-dimensional (3-D) scaffolds, with the local release of growth factors encapsulated in the scaffold, improve skeletal muscle regeneration compared to current technologies. Insertion of such a repair scaffold/cell/growth factor combination by minimally invasive surgical techniques, (e.g., using a needle or catheter) has wide clinical applicability.

The resorbable scaffold for delivery of growth factors and muscle progenitor cells mediates the localized release of growth factors and the enhancement of myoblast survival in the region of injured muscle tissues. Porous and biocompatible matrices provide space for cells to grow and survive and microenvironment for growth factor/drug retention and release. The devices and methods described represent a general approach to tissue regeneration that is applicable to the transplantation of many different cell types to enhance the regenerative response of multiple tissues.

Example 5

Neural Regeneration Using VEGF-Hydrogel Delivery Compositions

Figure 12A:
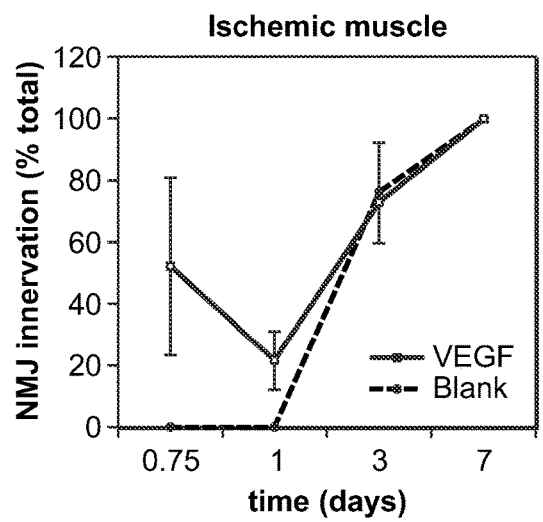
FIGS. 12A-B are line graphs, and FIGS. 12 C-E are photomicrographs showing that local delivery of VEGF promotes nerve regeneration and facilitates recovery following nerve damage in ischemic and healthy muscle.
Figure 12B:
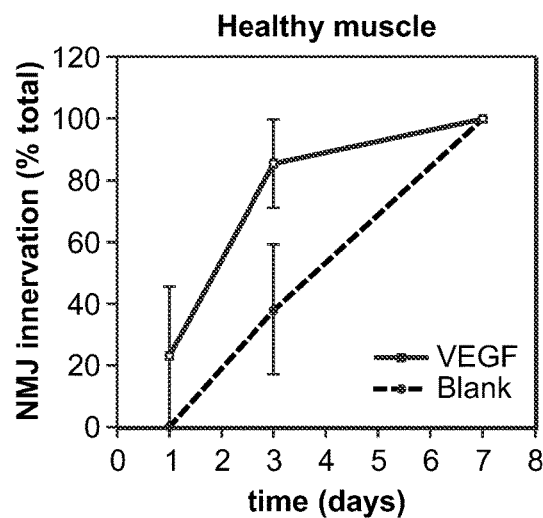
Figure 12C:
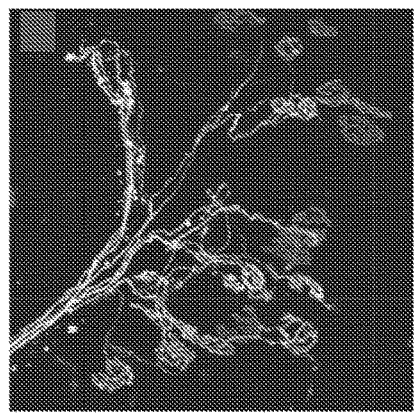
Figure 12D:
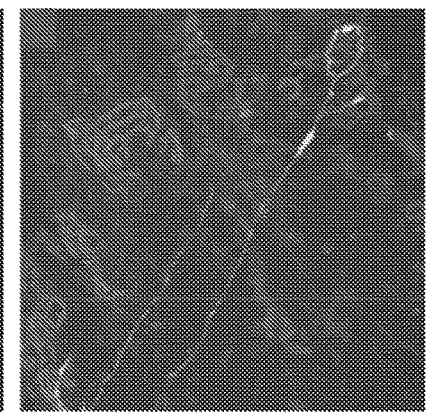
Figure 12E:
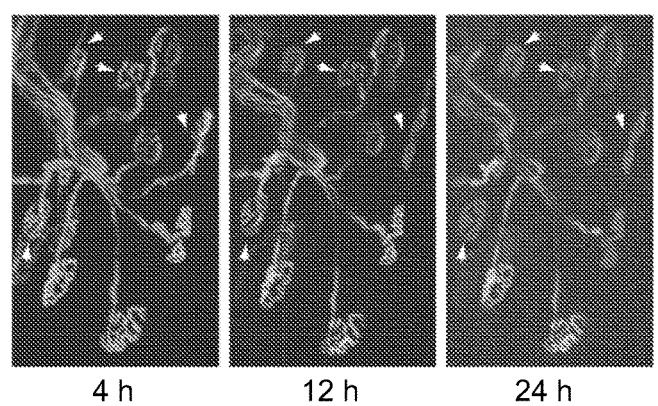

Hydrogel compositions, e.g., alginate gels, loaded with VEGF alone, i.e., in the absence of other growth factors, were found to prevent degeneration at the neuromuscular junction. FIGS. 12A-B show that innervation of neuromuscular junctions was significantly decreased following nerve crush injury in stemomas-toid muscle. Exogenous VEGF-gel delivery prevented complete degeneration and accelerated re-inervation. FIGS. 12C, D show that in the absence of exogenous VEGF, Wallerian degeneration of the nerves was observed within 24 h of the traumatic insult. Time-lapse imaging showing retraction of the motor axons (white arrows) due to the crush injury (FIG. 12E).

Neural regeneration by exogenous VEGF delivered in the context of a hydrogel is time and dose dependent. FIGS. 13A-C show dose-dependent neuromuscular joint innervations. Here, the optimal dose of VEGF was 3 µg. FIG. 13 D shows a timecourse of VEGF release from alginate hydrogels in vitro, showing the bulk release of VEGF within 7 days of incapsulation. The release kinetics are similar, regardless of the VEGF dose, with a rapid release for the first 5 days, followed by a slower, but continuing release for the duration of the analysis.

Maturation of motor axons in motor endplates and neuromuscular junction remodeling after the ischemic injury and neural crush was observed after local delivery of VEGF. Seven days after the injury, significant numbers of terminal axonal sprouts were present in NMJ treated with blank hydrogels, whereas VEGF delivery lowered the number of immature neuromuscular junctions (FIGS. 14 A, B). Multiple innervation was significantly increased in blank-supplemented muscles, whereas VEFG delivery resulted in one axon innervation of the motor endplate of injured muscle (FIGS. 14C,D). Both the percentage of neuromuscular junctions with multiple axons and % of neuromuscular junctions with axons that did not terminate at the motor endplate of the neuromuscular junctions (both halmarks of immature neuromuscular junctions) was reduced upon VEGF-gel delivery (FIG. 14E-F).

Figure 15B:
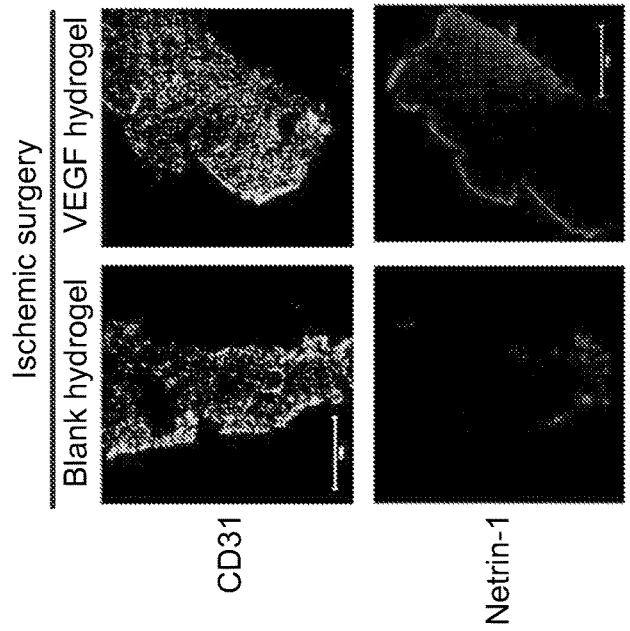
FIGS. 15A-C are a series of photomicrographs of stained cryosections showing that injection of VEGF-loaded hydrogels into ischemic tibialis anterior muscles elevates the expression of neurotrophic factors within 7 days after the injury.
Figure 15A:
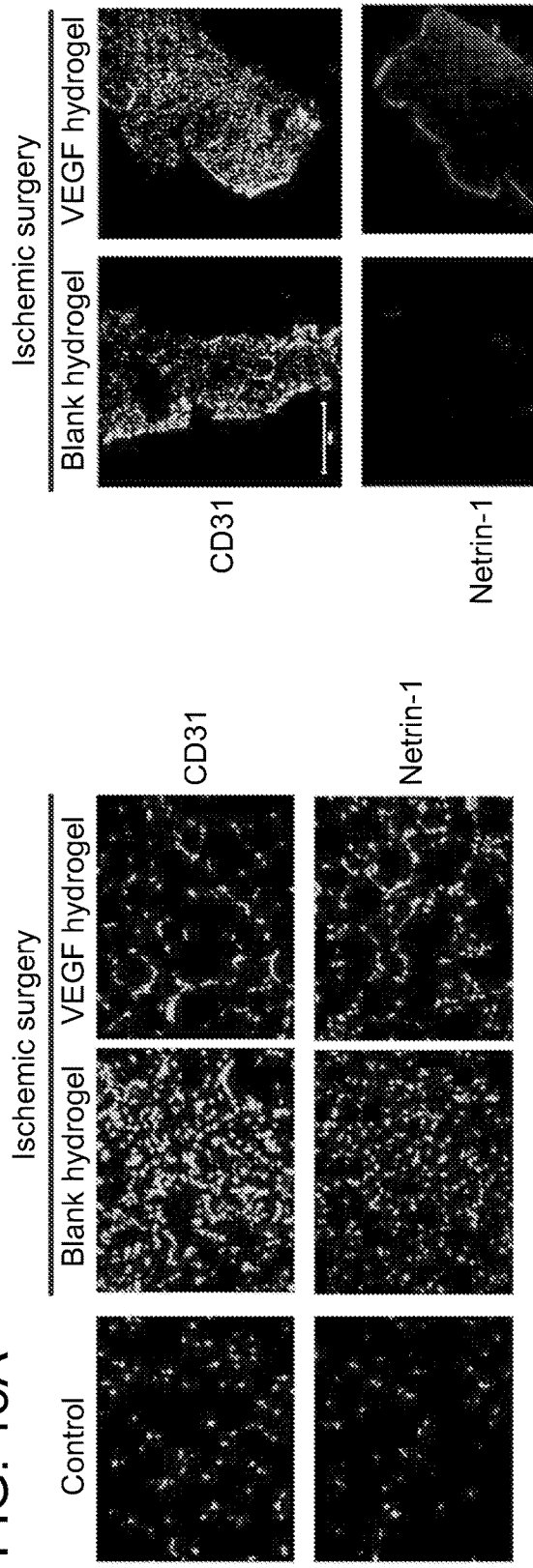
Figure 15C:
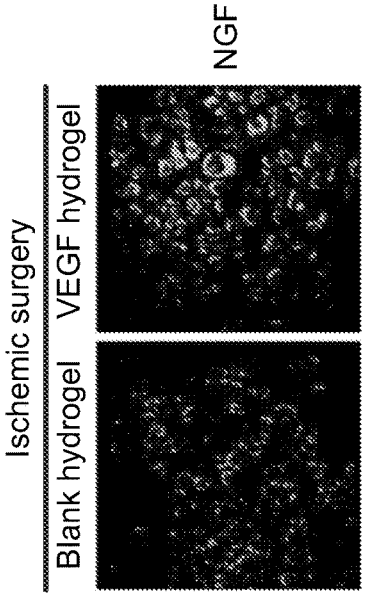

Injection of VEGF-loaded hydrogels into ischemic Tibialis Anterior muscles elevates the expression of neurotrophic factors within 7 days after the injury. Cryosections of the Tibilalis Anterior (TA) muscle showing elevated expression of Netrin-1 upon the delivery of VEGF (FIG. 15A). Panoramic images of the whole cryosection showing increased levels of Netrin-1 in VEGF supplemented ischemic TA muscle (FIG. 15B). Delivery of VEGF further elevated the expression levels of Neural Growth Factor (NGF) in ischemic TA muscles (FIG. 15C). The mechanism of VEGF-gel influence on the motor endplate reinnervations involves endogenous upregulation of these factors by endothelial cells.

Figure 16A:
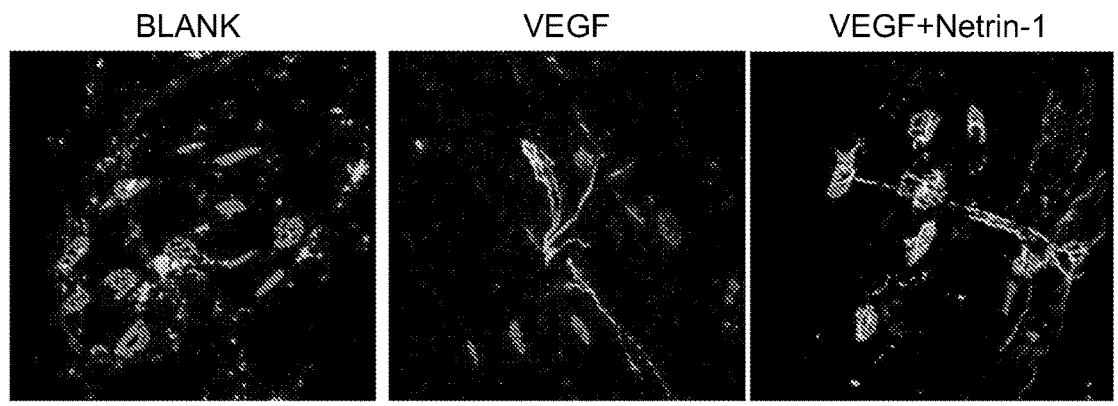
FIG. 16A is a series of photomicrographs.
Figure 16B:
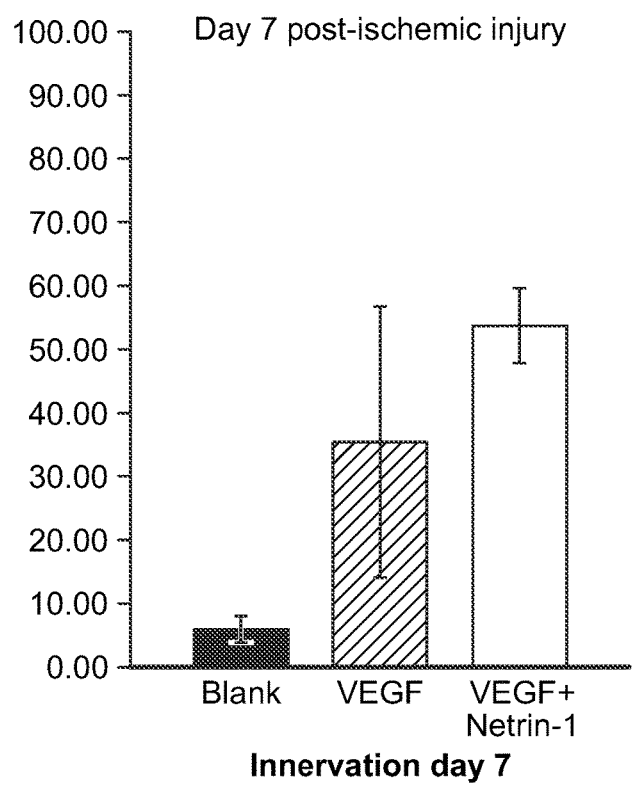
FIG. 16B is a bar graph showing that injection of alginate hydrogels supplemented with VEGF and Netrin-1 significantly elevates levels of neuromuscular junction innervation within 7 days of ischemic injury in TA muscle of mouse hindlimb.

Injection of alginate hydrogels supplemented with VEGF and Netrin-1 significantly elevates levels of neuromuscular junction innervation within 7 days of ischemic injury in TA muscle of mouse hindlimb. FIG. 16A shows representative images of neuromuscular junction innervation in ischemic TA muscles and increased innervation following VEGF and Netrin-1 delivery. FIG. 16B shows the results of a quantification of the TA innervation in ischemic TA muscles and a synergistic effect of the combined VEGF and Netrin-1 delivery. n=6 animals for each condition. Simultaneous delivery of VEGF and Netrin-1 enhances reinnervation of the motor endplates in a synergistic manner.

These data indicate that VEGF-containing hydrogels lead to a neuroprotection in the anatomical vicinity (at or near) of the site of administration. A therapeutic effect was noted at distances up to several centimeters away from the injection site. To treat a large tissue volume one would perform multiple gel injections, appropriately spaced in order to impact the entire tissue volume.

Example 6

Shape-Memory Polymers and Scaffolds

Shape memory polymers are characterized by their capacity to be highly compressed and recover their original shape from a stored packaged state in response to an environmental stimulus, e.g., administration into or onto a tissue of the body. Shape-memory materials, such as the compressed hydrogels described herein, are used to facilitate minimally invasive surgery by injection of a compressed structure which is a fraction of its original volume, but which then resumes its precompressed size and shape when implanted in vivo. The advantages of this type of material are that it combines the structure-defining property of implantable materials with the minimally invasive method for implantation of the material. This approach permits a less traumatic introduction of the implant into the body and reduces pain and recovery time. Macroporous alginate hydrogel scaffolds are prepared in predefined geometries, dehydrated and compressed into smaller, temporary forms. When rehydrated with a suspension of cells, e.g., by dropping a suspension of cells onto the dried scaffold, the scaffold returns to its original shape and was thus suitable for minimally invasive surgery. Dehydrated scaffolds are delivered through a needle or catheter and rehydrated in situ.

Figure 19:
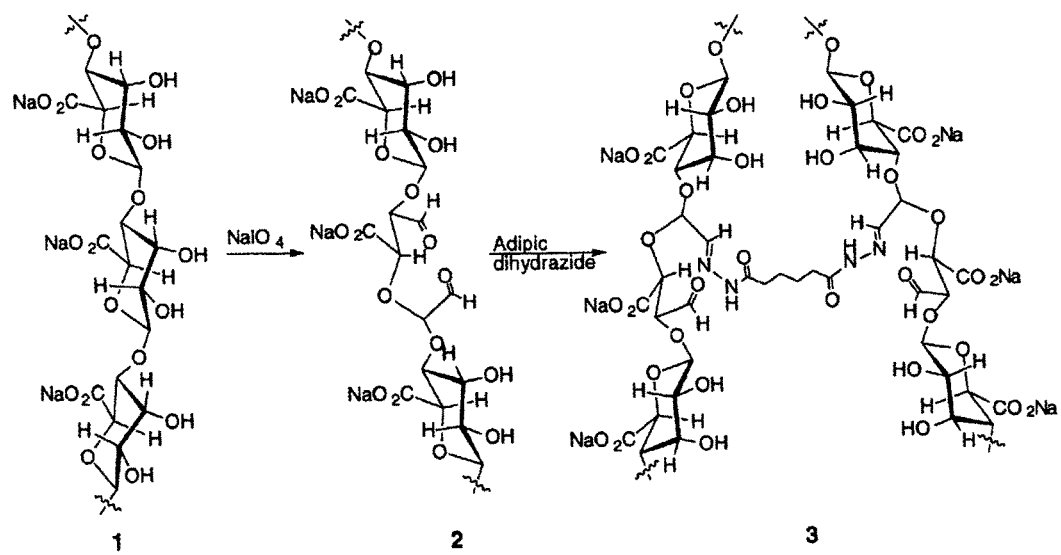
FIG. 19 depicts a scheme for the synthesis and cross-linking of poly(aldehyde guluronate).

Macroporous scaffolds with shape memory are covalently crosslinked. A scheme for the synthesis and cross-linking of poly(aldehyde guluronate) is provided at FIG. 19 (Polymer, Bouhadir K H, Hausman D. S, Mooney D. J, Synthesis of cross-linked poly(aldehyde guluronate) hydrogels. 1999. 40: p. 3575-3584).

The combination of shape-memory capability and biodegradability increases the multi-functionality of a biomaterial in medical devices used for minimally invasive surgery. Implant materials are injected in a compressed state into the body through a small incision or puncture hole (e.g., using a needle or catheter). After implantation, the hydrogel becomes rapidly rehydrated and restored to its previously-designed 3D shape. After these 3D matrices have served their purposes (cell and growth factor delivery), removal of the implants by follow-up surgery is not necessary, as the implant degrades.

Polymer Degradation

Polymer degradation is controlled using a variety of techniques such as irradiation, oxidation, and/or varying the molecular weight distribution of the polymer chains. One way to enhance degradation properties of alginate polymer is irradiation. Polymer degradation results from changes in polymeric chemical structure initiated by high energy electrons generated by gamma irradiation. Low molecular weight (LMW) polymer can be generated as the product of irradiated high molecular weight (HMW) polymer, and is subject to faster degradation. Low molecular weight means 5000-50,000 daltons; High molecular weight means 100,000-500,000 daltons. The molecular weight of the LMW polymer generated is determined by the irradiation dose and time of exposure. The percent LMW polymer generated is determined by the strength of the irradiation beam and time of exposure.

Exemplary compositions include 5% 1LMW:1HMW.

Oxidation

Another approach to control alginate gel degradation is partial periodate oxidation which offers control over the degradation rate—increasing the degree of oxidation accelerates the rate of degradation. When alginate is oxidized by reacting with sodium periodate ($NaIO_4$), the carbon-carbon bond of the cis-diol groups in the uronate residues are cleaved, and the aldehyde groups of oxidized hexuronic-acid residues spontaneously form six-membered hemiacetal rings with the closest hydroxyl groups on two adjacent, unoxidized sugar residues in the chains. This procedure alters the conformation of the molecules and creates hydrolytically labile bonds that facilitate faster degradation.

Alginates are naturally derived long chain polysaccharide copolymers formed by alternating or repeating the uronic functional units: mannuronic acid (M) and guluronic acid (G) and thus its chemical structure can be represented with MVG. Low molecular weight alginate can be generated by irradiating high molecular weight alginate at a dose of 5 Mrad for 4 hours. Both LMW and HMW alginate are then be oxidized by reacting with $NaIO_4$. The extent of oxidation is dependant on the amount of $NaIO_4$ reacted with the uronic acid function unit.

Molecular Weight Distribution

A third approach to regulate alginate gel degradation rate involves control over the molecular weight distribution of the polymer chains used to form scaffolds. Scaffolds formed from LMW polymer chains rapidly degrade in vivo but are mechanically weak. Therefore, the use of a bimodal molecular weight distribution combining HMW: LMW polymer in different ratios may result in the formation of mechanically stable gels with degradation rates that can be controlled.

Modification of the Scaffold with ECM Components

Modification of the scaffold for cell delivery includes binding of RGD peptides to encourage temporary cell adhesion. Generally, the surface chemistry conveyed through the adsorbed protein layer and macro-scale topographical features affect cell-surface interactions and greatly influence the success of an implant for tissue regeneration. Unmodified alginate does not facilitate mammalian cell adhesion due to its poor binding of serum proteins. Therefore, in order to allow the biomaterial to mimic the physicochemical properties of natural tissues for cell survival and proliferation, the surface and the bulk of the alginate needs modification by adding cell-binding peptides.

RGD (arginine-glycine-aspartic acid) is a peptide sequence that promotes cell adhesion and is present as the cell-binding domain of many extracellular matrix proteins. With RGD, the cells form attachments, which maintain and/or enhance cell survival and proliferation. In addition, these cell-peptide interactions may also promote other cell-specific functions, such as hormone production or cell migration into a repair site Scaffold Manufacture LMW alginate was generated by gamma irradiation of HMW LF 20/40 alginate (FMC Biopolymer, Philadelphia, Pa., USA) at 5.0 Mrad for 4 hours (h) with a cobalt-60 source for 4 h. To fabricate oxidized alginates, both LMW and HMW alginate were diluted to 1% w/v in ddH2O, and 1% and 5% and 10% of the sugar residues were oxidized using different amount of sodium periodate (Sigma-Aldrich, Saint Louis, Mo.) and maintaining solutions in the dark for 19 h at room temperature. An equimolar amount of ethylene glycol (Fisher scientific, Fair Lawn, N.J.) was added to quench the reaction, and the solution was subsequently dialyzed with Spectra/Por dialysis tubing (MWCO3500) (VWR International, Pittsburgh, Pa.), filtered and lyophilized to generate 1% and 5% and 10% oxidized LMW and HMW alginates. All alginate components were further modified with linear RGD peptide ($G_4$RGDSP-OH) (Commonwealth Biotechnology, Inc.) using 1-ethyl-(dimethyl aminopropyl) carbodiimide (EDC Sigma-Aldrich), N-hydroxysulfosuccinimide (sulfo-NHS, Pierce, Rockford, Ill.), and the bifunctional cross-linker adipic acid dihydrazide (AAD, Sigma-Aldrich).

Figure 20:
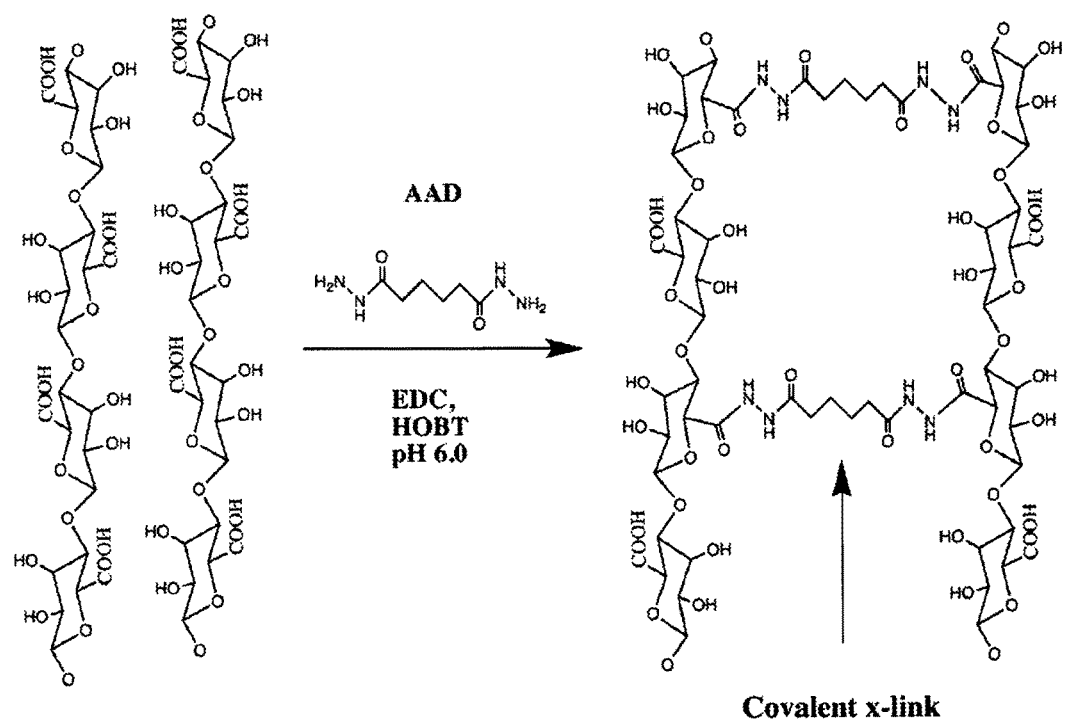
FIG. 20 depicts a scheme for the preparation of covalently cross-linked alginate scaffolds.

To prepare covalently cross-linked alginate scaffolds, sodium alginate 2% (w/v) was dissolved in MES buffer [0.1 M 2-(N-morpholino) ethanesulfonic acid (MES); 0.3 M NaCl], pH 6.0, and covalently cross-linked hydrogels were formed by standard carbodiimide chemistry using 1-ethyl-(dimethyl aminopropyl) carbodiimide (EDC), 1-hydroxybenzotriazole, and the bifunctional cross-linker adipic acid dihydrazide (AAD) (ratio of AAD:reactive groups on polymer; 1:20) as depicted in FIG. 20. Scaffolds were then placed in a large volume of distilled water, for a minimum of 24 hours, to attain equilibrium swelling and to remove residual unpolymerized chemicals.

Three different scaffolds were fabricated as follows, each with LMW and HMW alginates combined in a 1:1 weight ratio:
A. 1% binary group—1% oxidized HMW alginate×1% oxidized LMW alginate—(percent of oxidation refers to the percent of the uronic groups that are oxidized)
B. 5% binary group—5% oxidized HMW alginate×5% oxidized LMW alginate—
C. 10% binary group—10% oxidized HMW alginate×10% oxidized LMW alginate—

The resulting alginate materials were then frozen at −20° C. and lyophilized to generate macroporous scaffolds. Scaffold porosity (void volume) and pore characteristics, equilibrium swelling ratios (Qs), were all determined as described below. Scaffold dimensions were measured with Vernier calipers, lyophilized and then rehydrated with distilled water to determine the ability of the scaffolds to return to their original dimensions.

Swelling Ratio (Q) and Porosity Measurements

Scaffolds were equilibrated in distilled water at room temperature. After removing excess liquid from the surfaces by blotting, the scaffolds were weighed (WS) and diameter and thickness measurements were taken using Vernier calipers. Scaffolds were then frozen, lyophilized as described above, and the weight measurements repeated (WD). The swelling ratio (QS) is defined as the mass ratio of absorbed water to dry scaffold, calculated from:

$QS=(WS-WD)/WD$.

To determine the porosity (void volume) of the dry scaffolds, scaffolds were weighed (WS) and then reweighed after freezing and lyophilization (WD). The porosity was calculated from:

$(WS-WD)/WS \times 100\%$

SEM Scaffold Surface Morphology

The lyophilized scaffolds were placed on the surface of carbon adhesive paper and coated with gold nano-particles by a sputter coater to make the surface conductive. Default settings used for coating were: 4 min, 25 mA, 1 coating for each sample. Images were taken by a HITACHI 2700 Scanning Electron Microscope (Voltage: 6 KV/Beam current: 6*/Scanning speed: 160). The images were collected with a Quartz PCI digital imaging system (Quartz Imaging Corporation) and analyzed with ImageJ software (NIH).

Cell Distribution in Scaffolds

PMMGFP cells (GFP transduced primary mouse myoblasts) were grown at low density in tissue culture plates, and harvested by trypsinization. Five hundred thousand cells/scaffold were suspended in 50 µl PMMGM [PMMGM: 20% Fetal bovine serum (FBS), 39% Dulbecco's Modified Eagle Medium (DMEM, Gibco), 39% Fibroblast growth medium (FGM, Lonza), 1% ITS Liquid Media Supplement (Sigma) and 1% penicillin/strepmyosin (Sigma)] and pipetted dropwise onto the scaffolds in 35 mm diameter tissue culture dishes. The dishes were placed for 30 min in a 5% $CO^2$ humidified incubator at 37° C. before being covered with 1 ml PMMGM to immerse the scaffolds. The PMMGM was changed daily. Images were taken 2 weeks after the cells were seeded onto the scaffolds with a Leica TCS SP2 AOBS spectral confocal microscope. Images were acquired and analyzed with Leica confocal software (LCS) Version 2.5.

Shape Memory Properties of the Scaffold

Shape memory properties are important for delivery using a minimally invasive method. To evaluate the shape memory capacity of the 5% 1LMW:1HMW scaffold, the dehydrated and compressed scaffolds were rehydrated in vitro and investigated two main shape memory properties evaluated: porosity and swelling ratio. 1.2 mm-thick scaffolds were compressed at 500 psi to a thin film with an average thickness of 0.11 mm. Strikingly, the average swelling ratio was approximately 11, indicating that the scaffold can swell to ~11 times its volume after rehydration.

| Shape memory parameters | | | |
|---|---|---|---|
| Porosity | Swelling ratio | | % of volume recovered |
| Cross-link density | | | |
| Original scaffold | 98.1 + 0.1% | 56.2 + 2.2 | 90.0% (compressed manually)[80] |
| 5% LMW:HMW | 90.7 + 0.3% | 11.36 + 0.2 | 80.62% (compressed at 500 psi) |

Average porosity and swelling ratio for 5% oxidized covalently cross-linked scaffold. The lyophilized 5% oxidized 1LMW:1HMW scaffolds were compressed at 500 psi to a thin layer (0.12 mm in depth, measured by Venier calipers) then rehydrated with distilled water until equilibrium. The porosity and swelling ratio are calculated from the weight before and after rehydration. The original scaffold refers to an unmodified HMW covalently cross-linked shape memory scaffold. The original scaffold was compressed manually. Data represent mean±SEM (n=4).

The porosity was measured at ~90.7%, which implied that the scaffolds are very porous and have high water content (~90%). Collectively, these data indicate that the scaffolds made with the 5% oxidized LMW and 5% oxidized HMW at the ratio 1:1 maintained good shape memory properties after physical and chemical modifications to the original non-modified scaffolds. They also appear to have good porosity for cell uptake.

Scaffold Surface Morphology and Cell Distribution

Figure 17A:
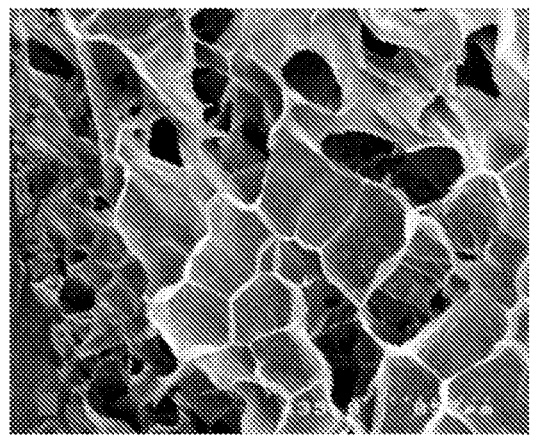
FIGS. 17A-C are photomicrographs. SEM image of the lyophilized porous 5% 1LMW:1HMW scaffold is shown in FIG. 17A, and confocal imaging of PMMGFP cells growing on the RGD modified 5% 1LMW:1HMW scaffold 30 mins after seeding and after 2 weeks in culture are shown in FIGS. 17B-C. The average pore size, calculated from the SEM images, was 412±17 µm. Data represent mean±SEM (n=4). Low molecular weight (LMW) range from 5000-50,000, while high molecular weight (HWM) range from 100,000-500,000.

The large porosity of the 5% 1LMW:1HMW scaffolds should offer a structural advantage for their use as a vehicle for delivery of cells for various repair and bioengineering applications. To further assess porosity of the scaffolds, their surface was imaged using a scanning electronic microscope (SEM). As illustrated in the FIG. 17a, the scaffolds were porous with the average pore size of 412 μm. This porosity feature facilitates cell infiltration and migration out of the scaffold as well as provides sufficient surface area for seeding significant cell numbers. In addition, the open porous structure facilitates exchange of nutrients and metabolites between seeded cells and the neighboring microenvironment.

Figure 17B:
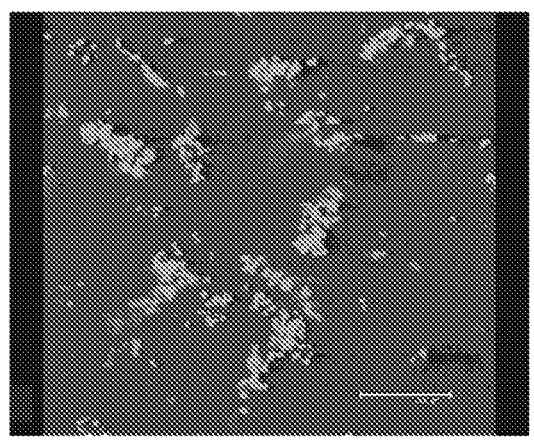
Figure 17C:
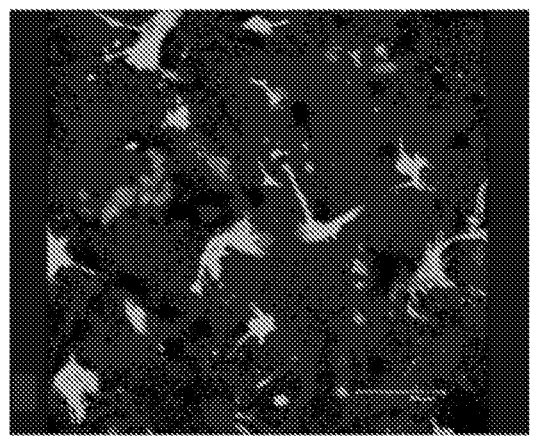

To assess cell distribution on these scaffolds, they were RGD modified and loaded with PMMGFP cells as described above. The cell suspension settled well into the pores of the scaffold (FIG. 17b), and after two weeks of incubation, cells appeared to be well attached to the scaffold, growing in clusters (FIG. 17c). After 2 weeks in culture, the cells were viable and proliferating, as determined by an increase in the number of viable cells inside the scaffold (measured by GFP assay) and the cell clusters had an even distribution pattern on the scaffold. (FIG. 17c)

Scaffold Geometries for Tibialis Muscle Regeneration and Design Considerations

The shape-memory scaffolds are used as a delivery vehicle for cells and growth factors to promote regeneration of injured muscle. In addition to surgery, the scaffolds are administered implantation using a minimally invasive technique to deposit it next to an injured or diseased muscle site. Thus, the dimensions of the scaffolds were designed to match geometries of target tissues. A severe murine tibialis anterior injury model was used for in vivo studies. In this case, the scaffolds were generated to be the approximate length of a tibialis anterior (13.5 mm) and a width equal to the circumference of a tibialis anterior (2.6 mm). The size is varied to accommodate the target site in the subject and the mode of administration (e.g., surgery, needle, or catheter). In the mouse model, the scaffolds were approximately 1.1 mm thick after rehydration. With these dimensions, the 5% 1LMW:1HMW was processed and delivered through a 1.5 mm angiocath to lie next to the tibialis anterior muscle (FIG. 18).

After rehydration, the covalently cross-linked scaffolds made from the 5% oxidized low molecular weight and high molecular weight alginate in a 1:1 ratio recovered more than 70% of their original volume. The scaffolds are also capable of restoring to their original dimensions after compression and rehydration. These results show that the modified scaffolds possess good shape memory properties.

The surface morphology shown by SEM imaging of a lyophilized scaffold indicates that the scaffold has a porous and interconnected structure. The porosity was also measured from the same set of data that generates swelling ratio. The porosity property confers to this covalently cross-linked scaffold an appropriate structure for seeding cells, and facilitates exchange of nutrients and metabolites within the surrounding in vivo microenviroment. In addition, the porosity data indicates that the rehydrated scaffolds have a high water content, which resembles normal muscle tissues.

The shape memory properties permit delivery of the dehydrated scaffolds to the site of the muscle damage with ease and accuracy. The scaffold is injected in a compressed state into the body through a small incision. After the injection of the scaffold, a subsequent injection of aqueous solution containing growth factors and cells efficiently rehydrates and restores the scaffold geometries. Since the scaffold degrades within a pre-defined time interval, surgical removal is not necessary after the scaffold has served its purpose, i.e., improving the survival of delivered cells and releasing growth factors for improved muscle regeneration.

Myoblasts Proliferate and Migrate Out to the Hydrogel Scaffold into Muscle Tissue Myoblasts proliferate and migrate out of the hydrogel scaffold and into recipient's muscle tissue continuously for at least 3 week period. To test cell proliferation on, and migration out of the alginate scaffolds, 0.3 million GFP transduced primary mouse myoblasts (PMMGFP) were seeded onto the scaffolds. The cells absorbed well into the porous scaffold material. Over a 3-week observation period, the cells proliferated and migrated from the scaffold onto the collagen-coated tissue culture plates (surrogate for muscle tissue of the subject). Cells migrated out of the scaffold 2 weeks after they were initially seeded and continued to grow on the plate surface. By the end of 3 weeks, there were approximately 0.81 million viable cells in the scaffold based on total GFP extraction and the cumulative number of cells that had migrated off the scaffold was approximately 0.11 million cells based on cell counts. These data indicate that myogenic cells proliferate and migrate out of the candidate scaffold continuously at a nearly constant rate during a 3-week period.

The efficiency of IGF-1 release from the scaffolds was also tested. Approximately 90% of the IGF-1 was released at a constant rate during the first three days, followed by sustained slower release rate from Day 3 to Day 14. By Day 14, nearly 100% of IGF-1 was released. Since IGF-1 was largely released within the first three days, IGF-1 has an effect on transplanted muscle progenitor cells and host satellite cells in the early stage of the injury recovery process. Satellite cells are activated immediately following injury as a pulse lasting for only a few days, and since IGF-1 stimulates proliferation and migration of satellite cells, the early burst release of IGF-1 from the scaffold is spatially and temporally synchronized with the activation of satellite cells. Upregulation of satellite cell proliferation and migration by IGF-1 further enhances myogenic cell-mediated skeletal muscle regeneration. The use of the scaffold to deliver growth factors provides the advantage of localized delivery, as growth factors are targeted to a small region near injury sites. By contrast, injected growth factors (in the absence of the hydrogel delivery vehicle/scaffold) are often either rapidly taken up by cells, quickly degraded, or bound up by extracellular matrix molecules, all of which cause a rapid decrease in their concentration. The scaffolds/vehicles described herein function as a localized delivery system for growth factors enhance the effects of the growth factors locally while eliminating side effects at other regions of the body, as would occur with systemic administration. Localized delivery limits the global impact of growth factors by minimizing their entry into the circulatory system. In addition, localized delivery reduces the amount of growth factors needed to achieve the desired effects. Thus, the biodegradable alginate scaffold has significant advantages as a vehicle for delivering cells and growth factors in vivo.

Growth Factor and Progenitor Cell Delivery from Scaffolds Promotes Muscle Regeneration The scaffold serves as a temporary delivery vehicle for muscle progenitor cells and growth factors, while avoiding the chronic problems associated with long term biomaterial implantation. Enriched populations of myoblasts were seeded onto the scaffold and the role of vehicle design in cell survival and migration was examined. The data indicate that long-term survival and migration of cells from the polymeric delivery vehicles and into host muscle tissue was achieved. Muscle progenitor cells can continuously proliferate and migrate out of the alginate scaffold during a 3-week period and longer. The alginate scaffold is also capable of prolonging IGF-1 release from the scaffold while maintaining its high local concentration temporarily. These data indicate that the alginate scaffold functions as a degradable ECM and temporary delivery vehicle for muscle progenitor cells and growth factors, which is useful to restore the function and the structure of the injured skeletal muscle.

Other embodiments are within the following claims.

The invention claimed is:

1. A method of enhancing muscle tissue repair or regeneration, comprising introducing into a muscle tissue of a human subject an injectable device comprising an alginate hydrogel comprising a combination of vascular endothelial growth factor 165 (VEGF$_{165}$) and insulin-like growth factor-1 (IGF-1), wherein the alginate hydrogel comprises oxidized alginate, wherein the VEGF$_{165}$ and the IGF-1 are released from the device into said muscle tissue, and wherein introduction of said device comprising a combination of VEGF$_{165}$ and IGF-1 provides a synergistic muscle tissue regeneration effect in the human subject.

2. The method of claim 1, wherein said muscle tissue comprises skeletal muscle tissue.

3. The method of claim 1, wherein said muscle tissue comprises smooth muscle tissue.

4. The method of claim 1, wherein said muscle tissue comprises cardiac muscle tissue.

5. The method of claim 1, wherein introduction of said device comprising a combination of $VEGF_{165}$ and IGF-1 provides an increase in blood vessel density in said muscle tissue.

6. The method of claim 1, wherein regional blood perfusion of muscle tissue is increased following introduction of said device.

7. The method of claim 1, wherein said device is introduced into a muscle tissue of the human subject using a needle.

8. The method of claim 1, wherein said device comprises macropores.

9. The method of claim 1, wherein said device further comprises a population of myogenic cells.

10. The method of claim 9, wherein said myogenic cells comprise myoblasts.

11. The method of claim 9, wherein said myogenic cells comprise satellite cells.

12. The method of claim 9, wherein said myogenic cells are seeded into or onto said hydrogel ex vivo.

13. The method of claim 1, wherein the alginate hydrogel comprises low molecular weight alginate and high molecular weight alginate.

14. The method of claim 13, wherein the alginate hydrogel comprises oxidized low molecular weight alginate and oxidized high molecular weight alginate.

15. The method of claim 14, wherein the ratio of low molecular weight to high molecular weight alginate is 1:1.

16. The method of claim 1, wherein the alginate hydrogel comprises 1%, 5%, or 10% oxidized alginate.

17. A method of treating an ischemic disease or ischemic injury in a human subject comprising introducing into a tissue of the human subject a device comprising an alginate hydrogel comprising a combination of vascular endothelial growth factor 165 ($VEGF_{165}$) and insulin-like growth factor-1 (IGF 1), wherein the alginate hydrogel comprises oxidized alginate, wherein the $VEGF_{165}$ and the IGF-1 are released from the device into the tissue, and wherein introduction of said device comprising a combination of $VEGF_{165}$ and IGF-1 provides a synergistic muscle tissue regeneration or revascularization effect in the human subject.

18. The method of claim 17, wherein the ischemic disease comprises chronic ischemia.

19. The method of claim 1, wherein the alginate hydrogel further comprises non-oxidized alginate.

* * * * *

UNITED STATES PATENT AND TRADEMARK OFFICE
CERTIFICATE OF CORRECTION

| | |
|---|---|
| PATENT NO. | : 9,610,328 B2 |
| APPLICATION NO. | : 13/582900 |
| DATED | : April 4, 2017 |
| INVENTOR(S) | : David J. Mooney et al. |

It is certified that error appears in the above-identified patent and that said Letters Patent is hereby corrected as shown below:

On the Title Page

(75) Inventors: replace "Dimitry" with --Dmitry--.

In the Claims

At Column 64, Claim number 17, Line number 13, replace "(IGF 1)" with --(IGF-1)--.

Signed and Sealed this
Twelfth Day of July, 2022

Katherine Kelly Vidal
*Director of the United States Patent and Trademark Office*

```
SEQUENCE LISTING

<160> NUMBER OF SEQ ID NOS: 9

<210> SEQ ID NO 1
<211> LENGTH: 354
<212> TYPE: PRT
<213> ORGANISM: Homo sapiens
<220> FEATURE:
<221> NAME/KEY: misc_feature
<223> OTHER INFORMATION: Human VEGF148

<400> SEQUENCE: 1

Met Thr Asp Arg Gln Thr Asp Thr Ala Pro Ser Pro Ser Tyr His Leu
1               5                   10                  15

Leu Pro Gly Arg Arg Thr Val Asp Ala Ala Ala Ser Arg Gly Gln
            20                  25                  30

Gly Pro Glu Pro Ala Pro Gly Gly Gly Val Glu Gly Val Gly Ala Arg
        35                  40                  45

Gly Val Ala Leu Lys Leu Phe Val Gln Leu Leu Gly Cys Ser Arg Phe
    50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140

Arg Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
```

-continued

```
                245                 250                 255
Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Asn Pro Cys Gly Pro Cys Ser Glu Arg Arg Lys His Leu Phe Val Gln
            325                 330                 335

Asp Pro Gln Thr Cys Lys Cys Ser Cys Lys Asn Thr Asp Ser Arg Cys
        340                 345                 350

Lys Met

<210> SEQ ID NO 2
<211> LENGTH: 371
<212> TYPE: PRT
<213> ORGANISM: Homo sapiens
<220> FEATURE:
<221> NAME/KEY: misc_feature
<223> OTHER INFORMATION: Human VEGF165

<400> SEQUENCE: 2

Met Thr Asp Arg Gln Thr Asp Thr Ala Pro Ser Pro Ser Tyr His Leu
1               5                  10                  15

Leu Pro Gly Arg Arg Arg Thr Val Asp Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
    50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
```

```
                    245                 250                 255
Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
            275                 280                 285

Ile Lys Pro His Gln Gly Gln His Ile Gly Glu Met Ser Phe Leu Gln
            290                 295                 300

His Asn Lys Cys Glu Cys Arg Pro Lys Lys Asp Arg Ala Arg Gln Glu
305                 310                 315                 320

Asn Pro Cys Gly Pro Cys Ser Glu Arg Arg Lys His Leu Phe Val Gln
            325                 330                 335

Asp Pro Gln Thr Cys Lys Cys Ser Cys Lys Asn Thr Asp Ser Arg Cys
            340                 345                 350

Lys Ala Arg Gln Leu Glu Leu Asn Glu Arg Thr Cys Arg Cys Asp Lys
            355                 360                 365

Pro Arg Arg
    370

<210> SEQ ID NO 3
<211> LENGTH: 371
<212> TYPE: PRT
<213> ORGANISM: Homo sapiens
<220> FEATURE:
<221> NAME/KEY: misc_feature
<223> OTHER INFORMATION: Human VEGF165b

<400> SEQUENCE: 3

Met Thr Asp Arg Gln Thr Asp Thr Ala Pro Ser Pro Ser Tyr His Leu
1               5                   10                  15

Leu Pro Gly Arg Arg Thr Val Asp Ala Ala Ala Ser Arg Gly Gln
            20                  25                  30

Gly Pro Glu Pro Ala Pro Gly Gly Gly Val Glu Gly Val Gly Ala Arg
            35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
            85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
    130                 135                 140

Arg Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
            165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
            195                 200                 205

Met Ala Glu Gly Gly Gly Gln Asn His His Glu Val Val Lys Phe Met
    210                 215                 220
```

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
            245                 250                 255

Cys Val Pro Leu Met Arg Cys Gly Gly Cys Cys Asn Asp Glu Gly Leu
        260                 265                 270

Glu Cys Val Pro Thr Glu Glu Ser Asn Ile Thr Met Gln Ile Met Arg
    275                 280                 285

Ile Lys Pro His Gln Gly Gln His Ile Gly Glu Met Ser Phe Leu Gln
290                 295                 300

His Asn Lys Cys Glu Cys Arg Pro Lys Lys Asp Arg Ala Arg Gln Glu
305                 310                 315                 320

Asn Pro Cys Gly Pro Cys Ser Glu Arg Arg Lys His Leu Phe Val Gln
                325                 330                 335

Asp Pro Gln Thr Cys Lys Cys Ser Cys Lys Asn Thr Asp Ser Arg Cys
            340                 345                 350

Lys Ala Arg Gln Leu Glu Leu Asn Glu Arg Thr Cys Arg Ser Leu Thr
        355                 360                 365

Arg Lys Asp
    370

<210> SEQ ID NO 4
<211> LENGTH: 389
<212> TYPE: PRT
<213> ORGANISM: Homo sapiens
<220> FEATURE:
<221> NAME/KEY: misc_feature
<223> OTHER INFORMATION: Human VEGF183

<400> SEQUENCE: 4

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
            20                  25                  30

Gly Pro Glu Pro Ala Pro Gly Gly Gly Val Glu Gly Val Gly Ala Arg
        35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
            85                  90                  95

Glu Glu Glu Glu Lys Glu Glu Glu Arg Gly Pro Gln Trp Arg Leu Gly
        100                 105                 110

Ala Arg Lys Pro Gly Ser Trp Thr Gly Glu Ala Ala Val Cys Ala Asp
    115                 120                 125

Ser Ala Pro Ala Ala Arg Ala Pro Gln Ala Leu Ala Arg Ala Ser Gly
130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
        210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
                260                 265                 270

Glu Cys Val Pro Thr Glu Glu Ser Asn Ile Thr Met Gln Ile Met Arg
            275                 280                 285

Ile Lys Pro His Gln Gly Gln His Ile Gly Glu Met Ser Phe Leu Gln
        290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Pro Cys Gly Pro Cys Ser Glu Arg Arg Lys His Leu Phe
                340                 345                 350

Val Gln Asp Pro Gln Thr Cys Lys Cys Ser Cys Lys Asn Thr Asp Ser
            355                 360                 365

Arg Cys Lys Ala Arg Gln Leu Glu Leu Asn Glu Arg Thr Cys Arg Cys
370                 375                 380

Asp Lys Pro Arg Arg
385

<210> SEQ ID NO 5
<211> LENGTH: 395
<212> TYPE: PRT
<213> ORGANISM: Homo sapiens
<220> FEATURE:
<221> NAME/KEY: misc_feature
<223> OTHER INFORMATION: Human VEGF189

<400> SEQUENCE: 5

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ser Arg Gly Gln
                20                  25                  30

Gly Pro Glu Pro Ala Pro Gly Gly Val Glu Gly Val Gly Ala Arg
            35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
                100                 105                 110

Ala Arg Lys Pro Gly Ser Trp Thr Gly Glu Ala Ala Val Cys Ala Asp
                115                 120                 125

Ser Ala Pro Ala Ala Arg Ala Pro Gln Ala Leu Ala Arg Ala Ser Gly
            130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg

-continued

```
                165                 170                 175
Ala Ser Glu Thr Met Asn Phe Leu Leu Ser Trp Val His Trp Ser Leu
            180                 185                 190
Ala Leu Leu Leu Tyr Leu His His Ala Lys Trp Ser Gln Ala Ala Pro
            195                 200                 205
Met Ala Glu Gly Gly Gly Gln Asn His His Glu Val Val Lys Phe Met
            210                 215                 220
Asp Val Tyr Gln Arg Ser Tyr Cys His Pro Ile Glu Thr Leu Val Asp
225                 230                 235                 240
Ile Phe Gln Glu Tyr Pro Asp Glu Ile Glu Tyr Ile Phe Lys Pro Ser
            245                 250                 255
Cys Val Pro Leu Met Arg Cys Gly Gly Cys Cys Asn Asp Glu Gly Leu
            260                 265                 270
Glu Cys Val Pro Thr Glu Glu Ser Asn Ile Thr Met Gln Ile Met Arg
            275                 280                 285
Ile Lys Pro His Gln Gly Gln His Ile Gly Glu Met Ser Phe Leu Gln
            290                 295                 300
His Asn Lys Cys Glu Cys Arg Pro Lys Lys Asp Arg Ala Arg Gln Glu
305                 310                 315                 320
Lys Lys Ser Val Arg Gly Lys Gly Lys Gly Gln Lys Arg Lys Arg Lys
            325                 330                 335
Lys Ser Arg Tyr Lys Ser Trp Ser Val Pro Cys Gly Pro Cys Ser Glu
            340                 345                 350
Arg Arg Lys His Leu Phe Val Gln Asp Pro Gln Thr Cys Lys Cys Ser
            355                 360                 365
Cys Lys Asn Thr Asp Ser Arg Cys Lys Ala Arg Gln Leu Glu Leu Asn
            370                 375                 380
Glu Arg Thr Cys Arg Cys Asp Lys Pro Arg Arg
385                 390                 395

<210> SEQ ID NO 6
<211> LENGTH: 412
<212> TYPE: PRT
<213> ORGANISM: Homo sapiens
<220> FEATURE:
<221> NAME/KEY: misc_feature
<223> OTHER INFORMATION: Human VEGF206

<400> SEQUENCE: 6

Met Thr Asp Arg Gln Thr Asp Thr Ala Pro Ser Pro Ser Tyr His Leu
1               5                   10                  15
Leu Pro Gly Arg Arg Thr Val Asp Ala Ala Ala Ser Arg Gly Gln
            20                  25                  30
Gly Pro Glu Pro Ala Pro Gly Gly Gly Val Glu Gly Val Gly Ala Arg
            35                  40                  45
Gly Val Ala Leu Lys Leu Phe Val Gln Leu Leu Gly Cys Ser Arg Phe
            50                  55                  60
Gly Gly Ala Val Val Arg Ala Gly Glu Ala Glu Pro Ser Gly Ala Ala
65                  70                  75                  80
Arg Ser Ala Ser Ser Gly Arg Glu Glu Pro Gln Pro Glu Glu Gly Glu
            85                  90                  95
Glu Glu Glu Glu Lys Glu Glu Glu Arg Gly Pro Gln Trp Arg Leu Gly
            100                 105                 110
Ala Arg Lys Pro Gly Ser Trp Thr Gly Glu Ala Ala Val Cys Ala Asp
            115                 120                 125
```

-continued

Ser Ala Pro Ala Ala Arg Ala Pro Gln Ala Leu Ala Arg Ala Ser Gly
    130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
                195                 200                 205

Met Ala Glu Gly Gly Gly Gln Asn His His Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
            340                 345                 350

Leu Met Pro Trp Ser Leu Pro Gly Pro His Pro Cys Gly Pro Cys Ser
        355                 360                 365

Glu Arg Arg Lys His Leu Phe Val Gln Asp Pro Gln Thr Cys Lys Cys
    370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410

<210> SEQ ID NO 7
<211> LENGTH: 71
<212> TYPE: PRT
<213> ORGANISM: Homo sapiens
<220> FEATURE:
<221> NAME/KEY: misc_feature
<223> OTHER INFORMATION: Human IGF-1

<400> SEQUENCE: 7

Met Gly Pro Glu Thr Leu Cys Gly Ala Glu Leu Val Asp Ala Leu Gln
1               5                   10                  15

Phe Val Cys Gly Asp Arg Gly Phe Tyr Phe Asn Lys Pro Thr Gly Tyr
            20                  25                  30

Gly Ser Ser Arg Arg Ala Pro Gln Thr Gly Met Val Asp Glu Cys
        35                  40                  45

Cys Phe Arg Ser Cys Asp Leu Arg Arg Leu Glu Met Tyr Cys Ala Pro
    50                  55                  60

Leu Lys Pro Ala Lys Ser Ala
65                  70

```
<210> SEQ ID NO 8
<211> LENGTH: 195
<212> TYPE: PRT
<213> ORGANISM: Homo sapiens
<220> FEATURE:
<221> NAME/KEY: misc_feature
<223> OTHER INFORMATION: Human IGF-1B isoform

<400> SEQUENCE: 8

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Tyr Gln Pro Pro Ser Thr Asn Lys Asn Thr
130                 135                 140

Lys Ser Gln Arg Arg Lys Gly Trp Pro Lys Thr His Pro Gly Gly Glu
145                 150                 155                 160

Gln Lys Glu Gly Thr Glu Ala Ser Leu Gln Ile Arg Gly Lys Lys Lys
                165                 170                 175

Glu Gln Arg Arg Glu Ile Gly Ser Arg Asn Ala Glu Cys Arg Gly Lys
            180                 185                 190

Lys Gly Lys
        195

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Gly Arg Gly Asp Ser Pro
1               5
```